United States Patent
Cheng

(10) Patent No.: US 11,246,694 B2
(45) Date of Patent: Feb. 15, 2022

(54) SYSTEM FOR INFORMATIONAL MAGNETIC FEEDBACK IN ADJUSTABLE IMPLANTS

(71) Applicant: NuVasive Specialized Orthopedics, Inc., San Diego, CA (US)

(72) Inventor: Shanbao Cheng, Irvine, CA (US)

(73) Assignee: NUVASIVE SPECIALIZED ORTHOPEDICS, INC., San Diego, CA (US)

(*) Notice: Subject to any disclaimer, the term of this patent is extended or adjusted under 35 U.S.C. 154(b) by 138 days.

(21) Appl. No.: 14/698,665

(22) Filed: Apr. 28, 2015

(65) Prior Publication Data

US 2015/0313745 A1 Nov. 5, 2015

Related U.S. Application Data

(60) Provisional application No. 61/985,406, filed on Apr. 28, 2014.

(51) Int. Cl.
*A61F 2/00* (2006.01)
*A61B 17/00* (2006.01)
(Continued)

(52) U.S. Cl.
CPC ........ *A61F 2/0036* (2013.01); *A61B 17/7016* (2013.01); *A61F 5/028* (2013.01);
(Continued)

(58) Field of Classification Search
CPC .............................................. A61F 2250/0001
See application file for complete search history.

(56) References Cited

U.S. PATENT DOCUMENTS

| 1,599,538 A | 9/1926 | Ludger |
| 2,702,031 A | 2/1955 | Wenger |

(Continued)

FOREIGN PATENT DOCUMENTS

| AU | 20068468 | 3/2001 |
| CN | 1697630 A | 11/2005 |

(Continued)

OTHER PUBLICATIONS

US 9,161,784 B2, 10/2015, Buttermann (withdrawn)
(Continued)

*Primary Examiner* — Jacqueline Woznicki
(74) *Attorney, Agent, or Firm* — Hoffman Warnick LLC

(57) ABSTRACT

According to some embodiments, systems and methods are provided for non-invasively detecting the force generated by a non-invasively adjustable implantable medical device and/or a change in dimension of a non-invasively adjustable implantable medical device. Some of the systems include a non-invasively adjustable implant, which includes a driven magnet, and an external adjustment device, which includes one or more driving magnets and one or more Hall effect sensors. The Hall effect sensors of the external adjustment device are configured to detect changes in the magnetic field between the driven magnet of the non-invasively adjustable implant and the driving magnet(s) of the external adjustment device. Changes in the magnetic fields may be used to calculate the force generated by and/or a change in dimension of the non-invasively adjustable implantable medical device.

18 Claims, 26 Drawing Sheets

(51) Int. Cl.
*A61F 5/02* (2006.01)
*G05B 15/02* (2006.01)
*A61B 17/70* (2006.01)
*A61B 90/00* (2016.01)
*A61B 17/04* (2006.01)

(52) U.S. Cl.
CPC .... *G05B 15/02* (2013.01); *A61B 2017/00039* (2013.01); *A61B 2017/00212* (2013.01); *A61B 2017/00411* (2013.01); *A61B 2017/00734* (2013.01); *A61B 2017/0453* (2013.01); *A61B 2090/061* (2016.02); *A61F 2250/0002* (2013.01)

(56) References Cited

U.S. PATENT DOCUMENTS

| | | |
|---|---|---|
| 3,111,945 A | 11/1963 | Von |
| 3,372,476 A | 3/1968 | Richard et al. |
| 3,377,576 A | 4/1968 | Edwin et al. |
| 3,397,928 A | 8/1968 | Galle |
| 3,512,901 A | 5/1970 | Law |
| 3,527,220 A | 9/1970 | Summers |
| 3,597,781 A | 8/1971 | Eibes et al. |
| 3,726,279 A | 4/1973 | Barefoot et al. |
| 3,749,098 A | 7/1973 | De Bennetot |
| 3,750,194 A | 8/1973 | Summers |
| 3,810,259 A | 5/1974 | Summers |
| 3,840,018 A | 10/1974 | Heifetz |
| 3,866,510 A | 2/1975 | Eibes et al. |
| 3,900,025 A | 8/1975 | Barnes, Jr. |
| 3,915,151 A | 10/1975 | Kraus |
| RE28,907 E | 7/1976 | Eibes et al. |
| 3,976,060 A | 8/1976 | Hildebrandt et al. |
| 4,010,758 A | 3/1977 | Rockland et al. |
| 4,056,743 A | 11/1977 | Clifford et al. |
| 4,068,821 A | 1/1978 | Morrison |
| 4,078,559 A | 3/1978 | Nissinen |
| 4,118,805 A | 10/1978 | Reimels |
| 4,204,541 A | 5/1980 | Kapitanov |
| 4,222,374 A | 9/1980 | Sampson et al. |
| 4,235,246 A | 11/1980 | Weiss |
| 4,256,094 A | 3/1981 | Kapp et al. |
| 4,286,584 A | 9/1981 | Sampson et al. |
| 4,300,223 A | 11/1981 | Maire |
| 4,357,946 A | 11/1982 | Dutcher et al. |
| 4,386,603 A | 6/1983 | Mayfield |
| 4,395,259 A | 7/1983 | Prestele et al. |
| 4,448,191 A | 5/1984 | Rodnyansky et al. |
| 4,486,176 A | 12/1984 | Tardieu et al. |
| 4,501,266 A | 2/1985 | McDaniel |
| 4,522,501 A | 6/1985 | Shannon |
| 4,537,520 A | 8/1985 | Ochiai et al. |
| 4,550,279 A | 10/1985 | Klein |
| 4,561,798 A | 12/1985 | Elcrin et al. |
| 4,573,454 A | 3/1986 | Hoffman |
| 4,592,339 A | 6/1986 | Kuzmak et al. |
| 4,592,355 A | 6/1986 | Antebi |
| 4,595,007 A | 6/1986 | Mericle |
| 4,608,992 A | 9/1986 | Hakim et al. |
| 4,642,257 A | 2/1987 | Chase |
| 4,658,809 A | 4/1987 | Ulrich et al. |
| 4,696,288 A | 9/1987 | Kuzmak et al. |
| 4,700,091 A | 10/1987 | Wuthrich |
| 4,747,832 A | 5/1988 | Buffet |
| 4,760,837 A | 8/1988 | Petit |
| 4,854,304 A | 8/1989 | Zielke |
| 4,872,515 A | 10/1989 | Lundell |
| 4,904,861 A | 2/1990 | Epstein et al. |
| 4,931,055 A | 6/1990 | Bumpus et al. |
| 4,940,467 A | 7/1990 | Tronzo |
| 4,957,495 A | 9/1990 | Kluger |
| 4,973,331 A | 11/1990 | Pursley et al. |
| 4,978,323 A | 12/1990 | Freedman |
| 4,998,013 A | 3/1991 | Epstein et al. |
| 5,010,879 A | 4/1991 | Moriya et al. |
| 5,030,235 A | 7/1991 | Campbell, Jr. |
| 5,041,112 A | 8/1991 | Mingozzi et al. |
| 5,053,047 A | 10/1991 | Yoon |
| 5,064,004 A | 11/1991 | Lundell |
| 5,074,868 A | 12/1991 | Kuzmak |
| 5,074,882 A | 12/1991 | Grammont et al. |
| 5,092,889 A | 3/1992 | Campbell, Jr. |
| 5,133,716 A | 7/1992 | Plaza |
| 5,142,407 A | 8/1992 | Varaprasad et al. |
| 5,152,770 A | 10/1992 | Bengmark et al. |
| 5,156,605 A | 10/1992 | Pursley et al. |
| 5,176,618 A | 1/1993 | Freedman |
| 5,180,380 A | 1/1993 | Pursley et al. |
| 5,222,976 A | 6/1993 | Yoon |
| 5,226,429 A | 7/1993 | Kuzmak |
| 5,261,908 A | 11/1993 | Campbell, Jr. |
| 5,263,955 A | 11/1993 | Baumgart et al. |
| 5,290,289 A | 3/1994 | Sanders et al. |
| 5,306,275 A | 4/1994 | Bryan |
| 5,330,503 A | 7/1994 | Yoon |
| 5,334,202 A | 8/1994 | Carter |
| 5,336,223 A | 8/1994 | Rogers |
| 5,356,411 A | 10/1994 | Spievack |
| 5,356,424 A | 10/1994 | Buzerak et al. |
| 5,360,407 A | 11/1994 | Leonard et al. |
| 5,364,396 A | 11/1994 | Robinson et al. |
| 5,381,943 A | 1/1995 | Allen et al. |
| 5,399,168 A | 3/1995 | Wadsworth, Jr. et al. |
| 5,403,322 A | 4/1995 | Herzenberg et al. |
| 5,429,638 A | 7/1995 | Muschler et al. |
| 5,433,721 A | 7/1995 | Hooven et al. |
| 5,437,266 A | 8/1995 | McPherson et al. |
| 5,438,990 A | 8/1995 | Wahlstrand et al. |
| 5,449,368 A | 9/1995 | Kuzmak |
| 5,466,261 A | 11/1995 | Richelsoph |
| 5,468,030 A | 11/1995 | Walling |
| 5,480,437 A | 1/1996 | Draenert |
| 5,498,262 A | 3/1996 | Bryan |
| 5,509,888 A | 4/1996 | Miller |
| 5,516,335 A | 5/1996 | Kummer et al. |
| 5,527,309 A | 6/1996 | Shelton |
| 5,536,269 A | 7/1996 | Spievack |
| 5,536,296 A | 7/1996 | Ten Eyck et al. |
| 5,549,610 A | 8/1996 | Russell et al. |
| 5,573,012 A | 11/1996 | McEwan |
| 5,573,496 A | 11/1996 | McPherson et al. |
| 5,575,790 A | 11/1996 | Chen et al. |
| 5,582,616 A | 12/1996 | Bolduc et al. |
| 5,601,224 A | 2/1997 | Bishop et al. |
| 5,620,445 A | 4/1997 | Brosnahan et al. |
| 5,620,449 A | 4/1997 | Faccioli et al. |
| 5,626,579 A | 5/1997 | Muschler et al. |
| 5,626,613 A | 5/1997 | Schmieding |
| 5,628,888 A | 5/1997 | Bakhir et al. |
| 5,632,744 A | 5/1997 | Campbell, Jr. |
| 5,659,217 A | 8/1997 | Petersen |
| 5,662,683 A | 9/1997 | Kay |
| 5,672,175 A | 9/1997 | Martin |
| 5,672,177 A | 9/1997 | Seldin |
| 5,676,162 A | 10/1997 | Larson, Jr. et al. |
| 5,693,091 A | 12/1997 | Larson, Jr. et al. |
| 5,700,263 A | 12/1997 | Schendel |
| 5,702,430 A | 12/1997 | Larson, Jr. et al. |
| 5,704,893 A | 1/1998 | Timm |
| 5,704,938 A | 1/1998 | Staehlin et al. |
| 5,704,939 A | 1/1998 | Justin |
| 5,720,746 A | 2/1998 | Soubeiran |
| 5,722,429 A | 3/1998 | Larson, Jr. et al. |
| 5,722,930 A | 3/1998 | Larson, Jr. et al. |
| 5,743,910 A | 4/1998 | Bays et al. |
| 5,758,666 A | 6/1998 | Larson, Jr. et al. |
| 5,762,599 A | 6/1998 | Sohn |
| 5,766,208 A | 6/1998 | McEwan |
| 5,771,903 A | 6/1998 | Jakobsson |
| 5,800,434 A | 9/1998 | Campbell, Jr. |
| 5,810,815 A | 9/1998 | Morales |
| 5,824,008 A | 10/1998 | Bolduc et al. |
| 5,827,286 A | 10/1998 | Incavo et al. |

(56) References Cited

U.S. PATENT DOCUMENTS

| | | |
|---|---|---|
| 5,829,662 A | 11/1998 | Allen et al. |
| 5,830,221 A | 11/1998 | Stein et al. |
| 5,843,129 A | 12/1998 | Larson, Jr. et al. |
| 5,874,796 A | 2/1999 | Petersen |
| 5,879,375 A | 3/1999 | Larson, Jr. et al. |
| 5,902,304 A | 5/1999 | Walker et al. |
| 5,935,127 A | 8/1999 | Border |
| 5,938,669 A | 8/1999 | Klaiber et al. |
| 5,945,762 A | 8/1999 | Chen et al. |
| 5,954,915 A | 9/1999 | Voorhees et al. |
| 5,961,553 A | 10/1999 | Coty et al. |
| 5,964,763 A | 10/1999 | Incavo et al. |
| 5,976,138 A | 11/1999 | Baumgart et al. |
| 5,979,456 A | 11/1999 | Magovern |
| 5,985,110 A | 11/1999 | Bakhir et al. |
| 5,997,490 A | 12/1999 | McLeod et al. |
| 6,009,837 A | 1/2000 | McClasky |
| 6,022,349 A | 2/2000 | McLeod et al. |
| 6,033,412 A | 3/2000 | Losken et al. |
| 6,034,296 A | 3/2000 | Elvin et al. |
| 6,067,991 A | 5/2000 | Forsell |
| 6,074,341 A | 6/2000 | Anderson et al. |
| 6,074,882 A | 6/2000 | Eckardt |
| 6,092,531 A | 7/2000 | Chen et al. |
| 6,102,922 A | 8/2000 | Jakobsson et al. |
| 6,106,525 A | 8/2000 | Sachse |
| 6,126,660 A | 10/2000 | Dietz |
| 6,126,661 A | 10/2000 | Faccioli et al. |
| 6,138,681 A | 10/2000 | Chen et al. |
| 6,139,316 A | 10/2000 | Sachdeva et al. |
| 6,162,223 A | 12/2000 | Orsak et al. |
| 6,183,476 B1 | 2/2001 | Gerhardt et al. |
| 6,200,317 B1 | 3/2001 | Aalsma et al. |
| 6,210,347 B1 | 4/2001 | Forsell |
| 6,217,847 B1 | 4/2001 | Contag et al. |
| 6,221,074 B1 | 4/2001 | Cole et al. |
| 6,234,299 B1 | 5/2001 | Voorhees et al. |
| 6,234,956 B1 | 5/2001 | He et al. |
| 6,241,730 B1 | 6/2001 | Alby |
| 6,245,075 B1 | 6/2001 | Betz et al. |
| 6,263,230 B1 | 7/2001 | Haynor et al. |
| 6,283,156 B1 | 9/2001 | Motley |
| 6,292,680 B1 | 9/2001 | Somogyi et al. |
| 6,296,643 B1 | 10/2001 | Hopf et al. |
| 6,296,656 B1 | 10/2001 | Bolduc et al. |
| 6,299,613 B1 | 10/2001 | Ogilvie et al. |
| 6,315,784 B1 | 11/2001 | Djurovic |
| 6,319,255 B1 | 11/2001 | Grundei et al. |
| 6,321,106 B1 | 11/2001 | Lemelson |
| 6,325,805 B1 | 12/2001 | Ogilvie et al. |
| 6,327,492 B1 | 12/2001 | Lemelson |
| 6,331,744 B1 | 12/2001 | Chen et al. |
| 6,336,929 B1 | 1/2002 | Justin |
| 6,343,568 B1 | 2/2002 | McClasky |
| 6,358,283 B1 | 3/2002 | Hogfors et al. |
| 6,375,682 B1 | 4/2002 | Fleischmann et al. |
| 6,386,083 B1 | 5/2002 | Hwang |
| 6,389,187 B1 | 5/2002 | Greenaway et al. |
| 6,400,980 B1 | 6/2002 | Lemelson |
| 6,402,753 B1 | 6/2002 | Cole et al. |
| 6,409,175 B1 | 6/2002 | Evans et al. |
| 6,416,516 B1 | 7/2002 | Stauch et al. |
| 6,417,750 B1 | 7/2002 | Sohn |
| 6,423,061 B1 | 7/2002 | Bryant |
| 6,432,040 B1 | 8/2002 | Meah |
| 6,450,173 B1 | 9/2002 | Forsell |
| 6,450,946 B1 | 9/2002 | Forsell |
| 6,453,907 B1 | 9/2002 | Forsell |
| 6,454,698 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,460,543 B1 | 10/2002 | Forsell |
| 6,461,292 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,470,892 B1 | 10/2002 | Forsell |
| 6,471,635 B1 | 10/2002 | Forsell |
| 6,475,136 B1 | 11/2002 | Forsell |
| 6,482,145 B1 | 11/2002 | Forsell |
| 6,494,879 B2 | 12/2002 | Lennox et al. |
| 6,499,907 B1 | 12/2002 | Baur |
| 6,500,110 B1 | 12/2002 | Davey et al. |
| 6,503,189 B1 | 1/2003 | Forsell |
| 6,508,820 B2 | 1/2003 | Bales |
| 6,510,345 B1 | 1/2003 | Van Bentem |
| 6,511,490 B2 | 1/2003 | Robert |
| 6,527,701 B1 | 3/2003 | Sayet et al. |
| 6,527,702 B2 | 3/2003 | Whalen et al. |
| 6,536,499 B2 | 3/2003 | Voorhees et al. |
| 6,537,196 B1 | 3/2003 | Creighton, IV et al. |
| 6,547,801 B1 | 4/2003 | Dargent et al. |
| 6,554,831 B1 | 4/2003 | Rivard et al. |
| 6,558,400 B2 | 5/2003 | Deem et al. |
| 6,562,051 B1 | 5/2003 | Bolduc et al. |
| 6,565,573 B1 | 5/2003 | Ferrante et al. |
| 6,565,576 B1 | 5/2003 | Stauch et al. |
| 6,573,706 B2 | 6/2003 | Mendes et al. |
| 6,582,313 B2 | 6/2003 | Perrow |
| 6,583,630 B2 | 6/2003 | Mendes et al. |
| 6,587,719 B1 | 7/2003 | Barrett et al. |
| 6,595,912 B2 | 7/2003 | Lau et al. |
| 6,602,184 B2 | 8/2003 | Lau et al. |
| 6,604,529 B2 | 8/2003 | Kim |
| 6,607,363 B1 | 8/2003 | Domroese |
| 6,609,025 B2 | 8/2003 | Barrett et al. |
| 6,612,978 B2 | 9/2003 | Lau et al. |
| 6,612,979 B2 | 9/2003 | Lau et al. |
| 6,616,669 B2 | 9/2003 | Ogilvie et al. |
| 6,621,956 B2 | 9/2003 | Greenaway et al. |
| 6,626,899 B2 | 9/2003 | Houser et al. |
| 6,626,917 B1 | 9/2003 | Craig |
| 6,627,206 B2 | 9/2003 | Lloyd |
| 6,649,143 B1 | 11/2003 | Contag et al. |
| 6,656,135 B2 | 12/2003 | Zogbi et al. |
| 6,656,194 B1 | 12/2003 | Gannoe et al. |
| 6,657,351 B2 | 12/2003 | Chen et al. |
| 6,667,725 B1 | 12/2003 | Simons et al. |
| 6,669,687 B1 | 12/2003 | Saadat |
| 6,673,079 B1 | 1/2004 | Kane |
| 6,676,674 B1 | 1/2004 | Dudai |
| 6,682,474 B2 | 1/2004 | Lau et al. |
| 6,689,046 B2 | 2/2004 | Sayet et al. |
| 6,702,732 B1 | 3/2004 | Lau et al. |
| 6,702,816 B2 | 3/2004 | Buhler |
| 6,706,042 B2 | 3/2004 | Taylor |
| 6,709,293 B2 | 3/2004 | Mori et al. |
| 6,709,385 B2 | 3/2004 | Forsell |
| 6,730,087 B1 | 5/2004 | Butsch |
| 6,749,556 B2 | 6/2004 | Banik |
| 6,752,754 B1 | 6/2004 | Feng et al. |
| 6,761,503 B2 | 7/2004 | Breese |
| 6,765,330 B2 | 7/2004 | Baur |
| 6,769,499 B2 | 8/2004 | Cargill et al. |
| 6,773,437 B2 | 8/2004 | Ogilvie et al. |
| 6,774,624 B2 | 8/2004 | Anderson et al. |
| 6,789,442 B2 | 9/2004 | Forch |
| 6,796,984 B2 | 9/2004 | Soubeiran |
| 6,802,844 B2 | 10/2004 | Ferree |
| 6,802,847 B1 | 10/2004 | Carson et al. |
| 6,809,434 B1 | 10/2004 | Duncan et al. |
| 6,835,183 B2 | 12/2004 | Lennox et al. |
| 6,835,207 B2 | 12/2004 | Zacouto et al. |
| 6,849,076 B2 | 2/2005 | Blunn et al. |
| 6,852,113 B2 | 2/2005 | Nathanson et al. |
| 6,864,647 B2 | 3/2005 | Duncan et al. |
| 6,884,248 B2 | 4/2005 | Bolduc et al. |
| 6,890,515 B2 | 5/2005 | Contag et al. |
| 6,908,605 B2 | 6/2005 | Contag et al. |
| 6,915,165 B2 | 7/2005 | Forsell |
| 6,916,326 B2 | 7/2005 | Benchetrit |
| 6,916,462 B2 | 7/2005 | Contag et al. |
| 6,918,838 B2 | 7/2005 | Schwarzler et al. |

(56) References Cited

U.S. PATENT DOCUMENTS

| | | |
|---|---|---|
| 6,918,910 B2 | 7/2005 | Smith et al. |
| 6,921,360 B2 | 7/2005 | Banik |
| 6,921,400 B2 | 7/2005 | Sohngen |
| 6,923,951 B2 | 8/2005 | Contag et al. |
| 6,926,719 B2 | 8/2005 | Sohngen et al. |
| 6,939,533 B2 | 9/2005 | Contag et al. |
| 6,953,429 B2 | 10/2005 | Forsell |
| 6,961,553 B2 | 11/2005 | Zhao et al. |
| 6,971,143 B2 | 12/2005 | Domroese |
| 6,980,921 B2 | 12/2005 | Anderson et al. |
| 6,997,952 B2 | 2/2006 | Furukawa et al. |
| 7,001,327 B2 | 2/2006 | Whalen et al. |
| 7,001,346 B2 | 2/2006 | White |
| 7,008,425 B2 | 3/2006 | Phillips |
| 7,009,386 B2 * | 3/2006 | Tromblee ............... B60N 2/002 324/207.2 |
| 7,011,621 B2 | 3/2006 | Sayet et al. |
| 7,011,658 B2 | 3/2006 | Young |
| 7,011,682 B2 | 3/2006 | Lashinski et al. |
| 7,018,380 B2 | 3/2006 | Cole |
| 7,029,472 B1 | 4/2006 | Fortin |
| 7,029,475 B2 | 4/2006 | Panjabi |
| 7,041,105 B2 | 5/2006 | Michelson |
| 7,060,075 B2 | 6/2006 | Govari et al. |
| 7,060,080 B2 | 6/2006 | Bachmann |
| 7,063,706 B2 | 6/2006 | Wittenstein |
| 7,077,802 B2 | 7/2006 | Lau et al. |
| 7,081,086 B2 | 7/2006 | Lau et al. |
| 7,083,629 B2 | 8/2006 | Weller et al. |
| 7,096,148 B2 | 8/2006 | Anderson et al. |
| 7,097,611 B2 | 8/2006 | Lau et al. |
| 7,105,029 B2 | 9/2006 | Doubler et al. |
| 7,105,968 B2 | 9/2006 | Nissen |
| 7,114,501 B2 | 10/2006 | Johnson et al. |
| 7,115,129 B2 | 10/2006 | Heggeness |
| 7,115,130 B2 | 10/2006 | Michelson |
| 7,124,493 B2 | 10/2006 | Lau et al. |
| 7,128,707 B2 | 10/2006 | Banik |
| 7,128,750 B1 | 10/2006 | Stergiopulos |
| 7,135,022 B2 | 11/2006 | Kosashvili et al. |
| 7,160,312 B2 | 1/2007 | Saadat |
| 7,163,538 B2 | 1/2007 | Altarac et al. |
| 7,172,607 B2 | 2/2007 | Hofle et al. |
| 7,175,589 B2 | 2/2007 | Deem et al. |
| 7,175,660 B2 | 2/2007 | Cartledge et al. |
| 7,186,262 B2 | 3/2007 | Saadat |
| 7,188,627 B2 | 3/2007 | Nelson et al. |
| 7,189,005 B2 | 3/2007 | Ward |
| 7,189,202 B2 | 3/2007 | Lau et al. |
| 7,189,251 B2 | 3/2007 | Kay |
| 7,191,007 B2 | 3/2007 | Desai et al. |
| 7,194,297 B2 | 3/2007 | Talpade et al. |
| 7,195,608 B2 | 3/2007 | Burnett |
| 7,198,774 B2 | 4/2007 | Contag et al. |
| 7,211,094 B2 | 5/2007 | Gannoe et al. |
| 7,216,648 B2 | 5/2007 | Nelson et al. |
| 7,217,284 B2 | 5/2007 | Houser et al. |
| 7,218,232 B2 | 5/2007 | DiSilvestro et al. |
| 7,232,449 B2 | 6/2007 | Sharkawy et al. |
| 7,234,468 B2 | 6/2007 | Johnson et al. |
| 7,234,544 B2 | 6/2007 | Kent |
| 7,238,152 B2 | 7/2007 | Lau et al. |
| 7,238,191 B2 | 7/2007 | Bachmann |
| 7,241,300 B2 | 7/2007 | Sharkawy et al. |
| 7,243,719 B2 | 7/2007 | Baron et al. |
| 7,255,682 B1 | 8/2007 | Bartol, Jr. et al. |
| 7,255,714 B2 | 8/2007 | Malek |
| 7,255,851 B2 | 8/2007 | Contag et al. |
| 7,276,022 B2 | 10/2007 | Lau et al. |
| 7,282,023 B2 | 10/2007 | Frering |
| 7,285,087 B2 | 10/2007 | Moaddeb et al. |
| 7,288,064 B2 | 10/2007 | Boustani et al. |
| 7,288,099 B2 | 10/2007 | Deem et al. |
| 7,288,101 B2 | 10/2007 | Deem et al. |
| 7,296,577 B2 | 11/2007 | Lashinski et al. |
| 7,297,150 B2 | 11/2007 | Cartledge et al. |
| 7,299,091 B2 | 11/2007 | Barrett et al. |
| 7,302,015 B2 | 11/2007 | Kim et al. |
| 7,302,858 B2 | 12/2007 | Walsh et al. |
| 7,306,614 B2 | 12/2007 | Weller et al. |
| 7,311,690 B2 | 12/2007 | Burnett |
| 7,314,372 B2 | 1/2008 | Belfor et al. |
| 7,314,443 B2 | 1/2008 | Jordan et al. |
| 7,320,706 B2 | 1/2008 | Al-Najjar |
| 7,331,995 B2 | 2/2008 | Eisermann et al. |
| 7,333,013 B2 | 2/2008 | Berger |
| 7,338,433 B2 | 3/2008 | Coe |
| 7,340,306 B2 | 3/2008 | Barrett et al. |
| 7,351,198 B2 | 4/2008 | Byrum et al. |
| 7,351,240 B2 | 4/2008 | Hassler, Jr. et al. |
| 7,353,747 B2 | 4/2008 | Swayze et al. |
| 7,357,037 B2 | 4/2008 | Hnat et al. |
| 7,357,635 B2 | 4/2008 | Belfor et al. |
| 7,360,542 B2 | 4/2008 | Nelson et al. |
| 7,361,192 B2 | 4/2008 | Doty |
| 7,364,542 B2 | 4/2008 | Jambor et al. |
| 7,364,589 B2 | 4/2008 | Eisermann |
| 7,367,340 B2 | 5/2008 | Nelson et al. |
| 7,367,937 B2 | 5/2008 | Jambor et al. |
| 7,367,938 B2 | 5/2008 | Forsell |
| 7,371,244 B2 | 5/2008 | Chatlynne et al. |
| 7,374,557 B2 | 5/2008 | Conlon et al. |
| 7,383,164 B2 | 6/2008 | Aram et al. |
| 7,390,007 B2 | 6/2008 | Helms et al. |
| 7,390,294 B2 | 6/2008 | Hassler, Jr. |
| 7,400,926 B2 | 7/2008 | Forsell |
| 7,402,134 B2 | 7/2008 | Moaddeb et al. |
| 7,402,176 B2 | 7/2008 | Malek |
| 7,410,461 B2 | 8/2008 | Lau et al. |
| 7,416,528 B2 | 8/2008 | Crawford et al. |
| 7,422,566 B2 | 9/2008 | Miethke |
| 7,429,259 B2 | 9/2008 | Cadeddu et al. |
| 7,431,692 B2 | 10/2008 | Zollinger et al. |
| 7,441,559 B2 | 10/2008 | Nelson et al. |
| 7,442,196 B2 | 10/2008 | Fisher et al. |
| 7,445,010 B2 | 11/2008 | Kugler et al. |
| 7,455,690 B2 | 11/2008 | Cartledge et al. |
| 7,458,981 B2 | 12/2008 | Fielding et al. |
| 7,468,060 B2 | 12/2008 | Utley et al. |
| 7,476,195 B2 | 1/2009 | Sayet et al. |
| 7,476,238 B2 | 1/2009 | Panjabi |
| 7,481,224 B2 | 1/2009 | Nelson et al. |
| 7,481,763 B2 | 1/2009 | Hassler, Jr. et al. |
| 7,481,841 B2 | 1/2009 | Hazebrouck et al. |
| 7,485,149 B1 | 2/2009 | White |
| 7,489,495 B2 | 2/2009 | Stevenson |
| 7,494,459 B2 | 2/2009 | Anstadt et al. |
| 7,500,484 B2 | 3/2009 | Nelson et al. |
| 7,503,922 B2 | 3/2009 | Deem et al. |
| 7,503,934 B2 | 3/2009 | Eisermann et al. |
| 7,507,252 B2 | 3/2009 | Lashinski et al. |
| 7,510,559 B2 | 3/2009 | Deem et al. |
| 7,525,309 B2 | 4/2009 | Sherman et al. |
| 7,530,981 B2 | 5/2009 | Kutsenko |
| 7,531,002 B2 | 5/2009 | Sutton et al. |
| 7,547,291 B2 | 6/2009 | Lennox et al. |
| 7,553,298 B2 | 6/2009 | Hunt et al. |
| 7,559,951 B2 | 7/2009 | DiSilvestro et al. |
| 7,561,916 B2 | 7/2009 | Hunt et al. |
| 7,562,660 B2 | 7/2009 | Saadat |
| 7,566,297 B2 | 7/2009 | Banik |
| 7,569,057 B2 | 8/2009 | Liu et al. |
| 7,578,821 B2 | 8/2009 | Fisher et al. |
| 7,584,788 B2 | 9/2009 | Baron et al. |
| 7,594,887 B2 | 9/2009 | Moaddeb et al. |
| 7,601,156 B2 | 10/2009 | Robinson |
| 7,601,162 B2 | 10/2009 | Hassler, Jr. et al. |
| 7,601,171 B2 | 10/2009 | Ainsworth et al. |
| 7,611,526 B2 | 11/2009 | Carl et al. |
| 7,615,001 B2 | 11/2009 | Jambor et al. |
| 7,615,068 B2 | 11/2009 | Timm et al. |
| 7,618,435 B2 | 11/2009 | Opolski |
| 7,621,886 B2 | 11/2009 | Burnett |
| 7,635,379 B2 | 12/2009 | Callahan et al. |

(56) References Cited

U.S. PATENT DOCUMENTS

| | | | |
|---|---|---|---|
| 7,651,483 B2 | 1/2010 | Byrum et al. |
| 7,658,753 B2 | 2/2010 | Carl et al. |
| 7,658,754 B2 | 2/2010 | Zhang et al. |
| 7,666,132 B2 | 2/2010 | Forsell |
| 7,666,184 B2 | 2/2010 | Stauch |
| 7,666,210 B2 | 2/2010 | Franck et al. |
| 7,678,136 B2 | 3/2010 | Doubler et al. |
| 7,678,139 B2 | 3/2010 | Garamszegi et al. |
| 7,691,103 B2 | 4/2010 | Fernandez et al. |
| 7,691,144 B2 | 4/2010 | Chang et al. |
| 7,695,512 B2 | 4/2010 | Lashinski et al. |
| 7,704,279 B2 | 4/2010 | Moskowitz et al. |
| 7,704,282 B2 | 4/2010 | Disilvestro et al. |
| 7,708,737 B2 | 5/2010 | Kraft et al. |
| 7,708,762 B2 | 5/2010 | McCarthy et al. |
| 7,708,765 B2 | 5/2010 | Carl et al. |
| 7,708,779 B2 | 5/2010 | Edie et al. |
| 7,713,287 B2 | 5/2010 | Timm et al. |
| 7,717,959 B2 | 5/2010 | William et al. |
| 7,727,141 B2 | 6/2010 | Hassler, Jr. et al. |
| 7,727,143 B2 | 6/2010 | Birk et al. |
| 7,749,224 B2 | 7/2010 | Cresina et al. |
| 7,753,913 B2 | 7/2010 | Szakelyhidi, Jr. et al. |
| 7,753,915 B1 | 7/2010 | Eksler et al. |
| 7,757,552 B2 | 7/2010 | Bogath et al. |
| 7,762,998 B2 | 7/2010 | Birk et al. |
| 7,763,053 B2 | 7/2010 | Gordon |
| 7,763,080 B2 | 7/2010 | Southworth |
| 7,766,815 B2 | 8/2010 | Ortiz |
| 7,766,855 B2 | 8/2010 | Miethke |
| 7,775,099 B2 | 8/2010 | Bogath et al. |
| 7,775,215 B2 | 8/2010 | Hassler, Jr. et al. |
| 7,776,061 B2 | 8/2010 | Garner et al. |
| 7,776,068 B2 | 8/2010 | Ainsworth et al. |
| 7,776,075 B2 | 8/2010 | Bruneau et al. |
| 7,776,091 B2 | 8/2010 | Mastrorio et al. |
| 7,780,590 B2 | 8/2010 | Birk et al. |
| 7,787,958 B2 | 8/2010 | Stevenson |
| 7,789,912 B2 | 9/2010 | Manzi et al. |
| 7,793,583 B2 | 9/2010 | Radinger et al. |
| 7,794,447 B2 | 9/2010 | Dann et al. |
| 7,794,476 B2 | 9/2010 | Wisnewski |
| 7,798,954 B2 | 9/2010 | Birk et al. |
| 7,799,080 B2 | 9/2010 | Doty |
| 7,803,106 B2 | 9/2010 | Whalen et al. |
| 7,803,157 B2 | 9/2010 | Michelson |
| 7,811,275 B2 | 10/2010 | Birk et al. |
| 7,811,298 B2 | 10/2010 | Birk |
| 7,811,328 B2 | 10/2010 | Molz, IV et al. |
| 7,815,643 B2 | 10/2010 | Johnson et al. |
| 7,828,714 B2 | 11/2010 | Feng et al. |
| 7,828,813 B2 | 11/2010 | Mouton |
| 7,833,228 B1 | 11/2010 | Hershberger |
| 7,835,779 B2 | 11/2010 | Anderson et al. |
| 7,837,669 B2 | 11/2010 | Dann et al. |
| 7,837,691 B2 | 11/2010 | Cordes et al. |
| 7,842,036 B2 | 11/2010 | Phillips |
| 7,845,356 B2 | 12/2010 | Paraschac et al. |
| 7,846,188 B2 | 12/2010 | Moskowitz et al. |
| 7,850,660 B2 | 12/2010 | Uth et al. |
| 7,850,735 B2 | 12/2010 | Eisermann et al. |
| 7,854,769 B2 | 12/2010 | Hershberger |
| 7,862,546 B2 | 1/2011 | Conlon et al. |
| 7,862,574 B2 | 1/2011 | Deem et al. |
| 7,862,586 B2 | 1/2011 | Malek |
| 7,867,235 B2 | 1/2011 | Fell et al. |
| 7,871,368 B2 | 1/2011 | Zollinger et al. |
| 7,875,033 B2 | 1/2011 | Richter et al. |
| 7,887,566 B2 | 2/2011 | Hynes |
| 7,901,381 B2 | 3/2011 | Birk et al. |
| 7,901,419 B2 | 3/2011 | Bachmann et al. |
| 7,909,790 B2 | 3/2011 | Burnett |
| 7,909,838 B2 | 3/2011 | Deem et al. |
| 7,909,839 B2 | 3/2011 | Fields |
| 7,909,852 B2 | 3/2011 | Boomer et al. |
| 7,918,844 B2 | 4/2011 | Byrum et al. |
| 7,921,850 B2 | 4/2011 | Nelson et al. |
| 7,922,765 B2 | 4/2011 | Reiley |
| 7,927,354 B2 | 4/2011 | Edidin et al. |
| 7,927,357 B2 | 4/2011 | Sacher et al. |
| 7,931,679 B2 | 4/2011 | Heggeness |
| 7,932,825 B2 | 4/2011 | Berger |
| 7,938,836 B2 | 5/2011 | Ainsworth et al. |
| 7,938,841 B2 | 5/2011 | Sharkawy et al. |
| 7,942,903 B2 | 5/2011 | Moskowitz et al. |
| 7,942,908 B2 | 5/2011 | Sacher et al. |
| 7,947,011 B2 | 5/2011 | Birk et al. |
| 7,948,231 B2 | 5/2011 | Takahashi et al. |
| 7,951,067 B2 | 5/2011 | Byrum et al. |
| 7,951,180 B2 | 5/2011 | Moskowitz et al. |
| 7,958,895 B2 | 6/2011 | Nelson et al. |
| 7,958,896 B2 | 6/2011 | Nelson et al. |
| 7,959,552 B2 | 6/2011 | Jordan et al. |
| 7,972,315 B2 | 7/2011 | Birk et al. |
| 7,972,346 B2 | 7/2011 | Bachmann et al. |
| 7,972,363 B2 | 7/2011 | Moskowitz et al. |
| 7,976,545 B2 | 7/2011 | Hershberger et al. |
| 7,983,763 B2 | 7/2011 | Stevenson et al. |
| 7,985,256 B2 | 7/2011 | Grotz et al. |
| 7,987,241 B2 | 7/2011 | St Jacques, Jr. et al. |
| 7,988,707 B2 | 8/2011 | Panjabi |
| 7,988,709 B2 | 8/2011 | Clark et al. |
| 7,993,342 B2 | 8/2011 | Malandain et al. |
| 7,993,397 B2 | 8/2011 | Lashinski et al. |
| 7,998,174 B2 | 8/2011 | Malandain et al. |
| 7,998,208 B2 | 8/2011 | Kohm et al. |
| 8,002,801 B2 | 8/2011 | Carl et al. |
| 8,002,809 B2 | 8/2011 | Baynham |
| 8,007,458 B2 | 8/2011 | Lennox et al. |
| 8,007,474 B2 | 8/2011 | Uth et al. |
| 8,007,479 B2 | 8/2011 | Birk et al. |
| 8,011,308 B2 | 9/2011 | Picchio |
| 8,012,162 B2 | 9/2011 | Bachmann |
| 8,016,745 B2 | 9/2011 | Hassler, Jr. et al. |
| 8,016,837 B2 | 9/2011 | Giger et al. |
| 8,016,860 B2 | 9/2011 | Carl et al. |
| 8,026,729 B2 | 9/2011 | Kroh et al. |
| 8,029,477 B2 | 10/2011 | Byrum et al. |
| 8,029,507 B2 | 10/2011 | Green et al. |
| 8,029,567 B2 | 10/2011 | Edidin et al. |
| 8,034,080 B2 | 10/2011 | Malandain et al. |
| 8,037,871 B2 | 10/2011 | McClendon |
| 8,038,680 B2 | 10/2011 | Ainsworth et al. |
| 8,038,698 B2 | 10/2011 | Edidin et al. |
| 8,043,206 B2 | 10/2011 | Birk |
| 8,043,290 B2 | 10/2011 | Harrison et al. |
| 8,043,299 B2 | 10/2011 | Conway |
| 8,043,338 B2 | 10/2011 | Dant |
| 8,043,345 B2 | 10/2011 | Carl et al. |
| 8,048,169 B2 | 11/2011 | Burnett et al. |
| 8,057,473 B2 | 11/2011 | Orsak et al. |
| 8,057,513 B2 | 11/2011 | Kohm et al. |
| 8,066,650 B2 | 11/2011 | Lee et al. |
| 8,070,670 B2 | 12/2011 | Deem et al. |
| 8,070,671 B2 | 12/2011 | Deem et al. |
| 8,070,695 B2 | 12/2011 | Gupta et al. |
| 8,070,813 B2 | 12/2011 | Grotz et al. |
| 8,074,654 B2 | 12/2011 | Paraschac et al. |
| 8,075,577 B2 | 12/2011 | Deem et al. |
| 8,079,974 B2 | 12/2011 | Stergiopulos |
| 8,079,989 B2 | 12/2011 | Birk et al. |
| 8,080,022 B2 | 12/2011 | Deem et al. |
| 8,080,025 B2 | 12/2011 | Deem et al. |
| 8,083,741 B2 | 12/2011 | Morgan et al. |
| 8,088,166 B2 | 1/2012 | Makower et al. |
| 8,092,459 B2 | 1/2012 | Malandain |
| 8,092,499 B1 | 1/2012 | Roth |
| 8,095,317 B2 | 1/2012 | Ekseth et al. |
| 8,096,302 B2 | 1/2012 | Nelson et al. |
| 8,096,938 B2 | 1/2012 | Forsell |
| 8,096,995 B2 | 1/2012 | Kohm et al. |
| 8,097,018 B2 | 1/2012 | Malandain et al. |
| 8,097,038 B2 | 1/2012 | Malek |
| 8,100,819 B2 | 1/2012 | Banik |

(56) References Cited

U.S. PATENT DOCUMENTS

| | | |
|---|---|---|
| 8,100,943 B2 | 1/2012 | Malandain et al. |
| 8,100,967 B2 | 1/2012 | Makower et al. |
| 8,105,360 B1 | 1/2012 | Connor |
| 8,105,363 B2 | 1/2012 | Fielding et al. |
| 8,105,364 B2 | 1/2012 | McCarthy et al. |
| 8,109,974 B2 | 2/2012 | Boomer et al. |
| 8,114,158 B2 | 2/2012 | Carl et al. |
| 8,123,765 B2 | 2/2012 | Deem et al. |
| 8,123,805 B2 | 2/2012 | Makower et al. |
| 8,128,628 B2 | 3/2012 | Freid et al. |
| 8,133,280 B2 | 3/2012 | Voellmicke et al. |
| 8,137,349 B2 | 3/2012 | Soubeiran |
| 8,137,366 B2 | 3/2012 | Deem et al. |
| 8,137,367 B2 | 3/2012 | Deem et al. |
| 8,142,454 B2 | 3/2012 | Harrison et al. |
| 8,142,494 B2 | 3/2012 | Randert et al. |
| 8,147,517 B2 | 4/2012 | Trieu et al. |
| 8,147,549 B2 | 4/2012 | Metcalf, Jr. et al. |
| 8,157,841 B2 | 4/2012 | Malandain et al. |
| 8,162,897 B2 | 4/2012 | Byrum |
| 8,162,979 B2 | 4/2012 | Sachs et al. |
| 8,163,013 B2 | 4/2012 | Machold et al. |
| 8,177,789 B2 | 5/2012 | Magill et al. |
| 8,182,411 B2 | 5/2012 | Dlugos |
| 8,187,324 B2 | 5/2012 | Webler et al. |
| 8,197,490 B2 | 6/2012 | Pool et al. |
| 8,197,544 B1 | 6/2012 | Manzi et al. |
| 8,202,305 B2 | 6/2012 | Reiley |
| 8,211,127 B2 | 7/2012 | Uth et al. |
| 8,211,149 B2 | 7/2012 | Justis |
| 8,211,151 B2 | 7/2012 | Schwab et al. |
| 8,211,179 B2 | 7/2012 | Molz, IV et al. |
| 8,216,275 B2 | 7/2012 | Fielding et al. |
| 8,221,420 B2 | 7/2012 | Keller |
| 8,226,690 B2 | 7/2012 | Altarac et al. |
| 8,236,002 B2 | 8/2012 | Fortin et al. |
| 8,241,292 B2 | 8/2012 | Collazo |
| 8,241,293 B2 | 8/2012 | Stone et al. |
| 8,241,331 B2 | 8/2012 | Arnin |
| 8,246,630 B2 | 8/2012 | Manzi et al. |
| 8,251,888 B2 | 8/2012 | Roslin et al. |
| 8,252,063 B2 | 8/2012 | Stauch |
| 8,257,370 B2 | 9/2012 | Moskowitz et al. |
| 8,257,442 B2 | 9/2012 | Edie et al. |
| 8,263,024 B2 | 9/2012 | Wan et al. |
| 8,267,969 B2 | 9/2012 | Altarac et al. |
| 8,273,112 B2 | 9/2012 | Garamszegi et al. |
| 8,278,941 B2 | 10/2012 | Kroh et al. |
| 8,282,671 B2 | 10/2012 | Connor |
| 8,287,540 B2 | 10/2012 | LeCronier et al. |
| 8,298,133 B2 | 10/2012 | Wiley et al. |
| 8,298,240 B2 | 10/2012 | Giger et al. |
| 8,308,779 B2 | 11/2012 | Reiley |
| 8,313,423 B2 | 11/2012 | Forsell |
| 8,316,856 B2 | 11/2012 | Nelson et al. |
| 8,317,761 B2 | 11/2012 | Birk et al. |
| 8,317,802 B1 | 11/2012 | Manzi et al. |
| 8,323,290 B2 | 12/2012 | Metzger et al. |
| 8,326,435 B2 | 12/2012 | Stevenson |
| 8,328,807 B2 | 12/2012 | Brigido |
| 8,328,854 B2 | 12/2012 | Baynham et al. |
| 8,333,204 B2 | 12/2012 | Saadat |
| 8,333,790 B2 | 12/2012 | Timm et al. |
| 8,353,913 B2 | 1/2013 | Moskowitz et al. |
| 8,357,169 B2 | 1/2013 | Henniges et al. |
| 8,357,182 B2 | 1/2013 | Seme |
| 8,357,183 B2 | 1/2013 | Seme et al. |
| 8,360,955 B2 | 1/2013 | Sayet et al. |
| 8,366,628 B2 | 2/2013 | Denker et al. |
| 8,372,078 B2 | 2/2013 | Collazo |
| 8,382,652 B2 | 2/2013 | Sayet et al. |
| 8,386,018 B2 | 2/2013 | Stauch et al. |
| 8,388,667 B2 | 3/2013 | Reiley et al. |
| 8,394,124 B2 | 3/2013 | Biyani |
| 8,394,143 B2 | 3/2013 | Grotz et al. |
| 8,403,958 B2 | 3/2013 | Schwab |
| 8,409,203 B2 | 4/2013 | Birk et al. |
| 8,409,281 B2 | 4/2013 | Makower et al. |
| 8,414,584 B2 | 4/2013 | Brigido |
| 8,414,648 B2 | 4/2013 | Reiley |
| 8,419,734 B2 | 4/2013 | Walker et al. |
| 8,419,755 B2 | 4/2013 | Deem et al. |
| 8,419,801 B2 | 4/2013 | DiSilvestro et al. |
| 8,425,570 B2 | 4/2013 | Reiley |
| 8,425,608 B2 | 4/2013 | Dewey et al. |
| 8,433,519 B2 | 4/2013 | Ekseth et al. |
| 8,435,268 B2 | 5/2013 | Thompson et al. |
| 8,439,915 B2 | 5/2013 | Harrison et al. |
| 8,439,926 B2 | 5/2013 | Bojarski et al. |
| 8,444,693 B2 | 5/2013 | Reiley |
| 8,449,553 B2 | 5/2013 | Kam et al. |
| 8,449,580 B2 | 5/2013 | Voellmicke et al. |
| 8,454,695 B2 | 6/2013 | Grotz et al. |
| 8,469,908 B2 | 6/2013 | Asfora |
| 8,469,978 B2 | 6/2013 | Fobi et al. |
| 8,470,003 B2 | 6/2013 | Voellmicke et al. |
| 8,470,004 B2 | 6/2013 | Reiley |
| 8,475,354 B2 | 7/2013 | Phillips et al. |
| 8,475,356 B2 | 7/2013 | Feng et al. |
| 8,475,499 B2 | 7/2013 | Cournoyer et al. |
| 8,480,554 B2 | 7/2013 | Phillips et al. |
| 8,480,668 B2 | 7/2013 | Fernandez et al. |
| 8,480,741 B2 | 7/2013 | Grotz et al. |
| 8,486,070 B2 | 7/2013 | Morgan et al. |
| 8,486,076 B2 | 7/2013 | Chavarria et al. |
| 8,486,110 B2 | 7/2013 | Fielding et al. |
| 8,486,113 B2 | 7/2013 | Malek |
| 8,486,147 B2 | 7/2013 | de Villiers et al. |
| 8,491,589 B2 | 7/2013 | Fisher et al. |
| 8,494,805 B2 | 7/2013 | Roche et al. |
| 8,496,662 B2 | 7/2013 | Novak et al. |
| 8,500,810 B2 | 8/2013 | Mastrorio et al. |
| 8,506,517 B2 | 8/2013 | Stergiopulos |
| 8,506,569 B2 | 8/2013 | Keefer et al. |
| 8,517,973 B2 | 8/2013 | Burnett |
| 8,518,062 B2 | 8/2013 | Cole et al. |
| 8,518,086 B2 | 8/2013 | Seme et al. |
| 8,522,790 B2 | 9/2013 | Nelson et al. |
| 8,523,865 B2 | 9/2013 | Reglos et al. |
| 8,523,866 B2 | 9/2013 | Sidebotham et al. |
| 8,523,883 B2 | 9/2013 | Saadat |
| 8,529,474 B2 | 9/2013 | Gupta et al. |
| 8,529,606 B2 | 9/2013 | Alamin et al. |
| 8,529,607 B2 | 9/2013 | Alamin et al. |
| 8,529,630 B2 | 9/2013 | Bojarski et al. |
| 8,545,384 B2 | 10/2013 | Forsell |
| 8,545,508 B2 | 10/2013 | Collazo |
| 8,545,814 B2 | 10/2013 | Contag et al. |
| 8,551,092 B2 | 10/2013 | Morgan et al. |
| 8,551,142 B2 | 10/2013 | Altarac et al. |
| 8,551,422 B2 | 10/2013 | Wan et al. |
| 8,556,901 B2 | 10/2013 | Anthony et al. |
| 8,556,911 B2 | 10/2013 | Mehta et al. |
| 8,556,975 B2 | 10/2013 | Ciupik et al. |
| 8,562,653 B2 | 10/2013 | Alamin et al. |
| 8,568,416 B2 | 10/2013 | Schmitz et al. |
| 8,568,457 B2 | 10/2013 | Hunziker |
| 8,574,267 B2 | 11/2013 | Linares |
| 8,579,919 B2 | 11/2013 | Bolduc et al. |
| 8,579,979 B2 | 11/2013 | Edie et al. |
| 8,585,595 B2 | 11/2013 | Heilman |
| 8,585,702 B2 | 11/2013 | Orsak et al. |
| 8,585,738 B2 | 11/2013 | Linares |
| 8,585,740 B1 | 11/2013 | Ross et al. |
| 8,591,549 B2 | 11/2013 | Lange |
| 8,591,553 B2 | 11/2013 | Eisermann et al. |
| 8,597,362 B2 | 12/2013 | Shenoy et al. |
| 8,613,749 B2 | 12/2013 | Deem et al. |
| 8,613,758 B2 | 12/2013 | Linares |
| 8,617,212 B2 | 12/2013 | Linares |
| 8,617,220 B2 | 12/2013 | Skaggs |
| 8,617,243 B2 | 12/2013 | Eisermann et al. |
| 8,622,936 B2 | 1/2014 | Schenberger et al. |
| 8,623,036 B2 | 1/2014 | Harrison et al. |

(56) References Cited

U.S. PATENT DOCUMENTS

| | | |
|---|---|---|
| 8,623,042 B2 | 1/2014 | Roslin et al. |
| 8,623,056 B2 | 1/2014 | Linares |
| 8,632,544 B2 | 1/2014 | Haaja et al. |
| 8,632,547 B2 | 1/2014 | Maxson et al. |
| 8,632,548 B2 | 1/2014 | Soubeiran |
| 8,632,563 B2 | 1/2014 | Nagase et al. |
| 8,632,594 B2 | 1/2014 | Williams et al. |
| 8,636,770 B2 | 1/2014 | Hestad et al. |
| 8,636,771 B2 | 1/2014 | Butler et al. |
| 8,636,802 B2 | 1/2014 | Serhan et al. |
| 8,641,719 B2 | 2/2014 | Gephart et al. |
| 8,641,723 B2 | 2/2014 | Connor |
| 8,652,175 B2 | 2/2014 | Timm et al. |
| 8,657,765 B2 | 2/2014 | Asfora |
| 8,657,856 B2 | 2/2014 | Gephart et al. |
| 8,657,885 B2 | 2/2014 | Burnett et al. |
| 8,663,139 B2 | 3/2014 | Asfora |
| 8,663,140 B2 | 3/2014 | Asfora |
| 8,663,285 B2 | 3/2014 | Dall et al. |
| 8,663,287 B2 | 3/2014 | Butler et al. |
| 8,663,338 B2 | 3/2014 | Burnett et al. |
| 8,668,719 B2 | 3/2014 | Alamin et al. |
| 8,673,001 B2 | 3/2014 | Cartledge et al. |
| 8,679,161 B2 | 3/2014 | Malandain et al. |
| 8,690,858 B2 | 4/2014 | Machold et al. |
| 8,707,959 B2 | 4/2014 | Paraschac et al. |
| 8,709,090 B2 | 4/2014 | Makower et al. |
| 8,715,243 B2 | 5/2014 | Uth et al. |
| 8,715,290 B2 | 5/2014 | Fisher et al. |
| 8,721,570 B2 | 5/2014 | Gupta et al. |
| 8,721,643 B2 | 5/2014 | Morgan et al. |
| 8,728,125 B2 | 5/2014 | Bruneau et al. |
| 8,734,318 B2 | 5/2014 | Forsell |
| 8,734,516 B2 | 5/2014 | Moskowitz et al. |
| 8,734,519 B2 | 5/2014 | de Villiers et al. |
| 8,747,444 B2 | 6/2014 | Moskowitz et al. |
| 8,752,552 B2 | 6/2014 | Nelson et al. |
| 8,758,303 B2 | 6/2014 | Uth et al. |
| 8,758,347 B2 | 6/2014 | Weiner et al. |
| 8,758,355 B2 | 6/2014 | Fisher et al. |
| 8,758,372 B2 | 6/2014 | Cartledge et al. |
| 8,762,308 B2 | 6/2014 | Najarian et al. |
| 8,764,713 B2 | 7/2014 | Uth et al. |
| 8,771,272 B2 | 7/2014 | LeCronier et al. |
| 8,777,947 B2 | 7/2014 | Zahrly et al. |
| 8,777,995 B2 | 7/2014 | McClintock et al. |
| 8,781,744 B2 | 7/2014 | Ekseth et al. |
| 8,784,482 B2 | 7/2014 | Rahdert et al. |
| 8,790,343 B2 | 7/2014 | McClellan et al. |
| 8,790,380 B2 | 7/2014 | Buttermann |
| 8,790,409 B2 | 7/2014 | Van den Heuvel et al. |
| 8,794,243 B2 | 8/2014 | Deem et al. |
| 8,795,339 B2 | 8/2014 | Boomer et al. |
| 8,801,795 B2 | 8/2014 | Makower et al. |
| 8,808,206 B2 | 8/2014 | Asfora |
| 8,813,727 B2 | 8/2014 | McClendon |
| 8,814,869 B2 | 8/2014 | Freid et al. |
| 8,828,058 B2 | 9/2014 | Elsebaie et al. |
| 8,828,087 B2 | 9/2014 | Stone et al. |
| 8,840,623 B2 | 9/2014 | Reiley |
| 8,840,651 B2 | 9/2014 | Reiley |
| 8,845,692 B2 | 9/2014 | Wisnewski |
| 8,845,724 B2 | 9/2014 | Shenoy et al. |
| 8,864,717 B2 | 10/2014 | Conlon et al. |
| 8,864,823 B2 | 10/2014 | Cartledge et al. |
| 8,870,881 B2 | 10/2014 | Rezach et al. |
| 8,870,918 B2 | 10/2014 | Boomer et al. |
| 8,870,959 B2 | 10/2014 | Arnin |
| 8,882,699 B2 | 11/2014 | Burnett |
| 8,882,830 B2 | 11/2014 | Cartledge et al. |
| 8,888,672 B2 | 11/2014 | Phillips et al. |
| 8,888,673 B2 | 11/2014 | Phillips et al. |
| 8,894,663 B2 | 11/2014 | Giger et al. |
| 8,915,915 B2 | 12/2014 | Harrison et al. |
| 8,915,917 B2 | 12/2014 | Doherty et al. |
| 8,920,422 B2 | 12/2014 | Homeier et al. |
| 8,932,247 B2 | 1/2015 | Stergiopulos |
| 8,945,188 B2 | 2/2015 | Rezach et al. |
| 8,945,210 B2 | 2/2015 | Cartledge et al. |
| 8,956,407 B2 | 2/2015 | Macoviak et al. |
| 8,961,386 B2 | 2/2015 | Phillips et al. |
| 8,961,521 B2 | 2/2015 | Keefer et al. |
| 8,961,567 B2 | 2/2015 | Hunziker |
| 8,968,402 B2 | 3/2015 | Myers et al. |
| 8,968,406 B2 | 3/2015 | Arnin |
| 8,974,463 B2 | 3/2015 | Pool et al. |
| 8,986,348 B2 | 3/2015 | Reiley |
| 8,992,527 B2 | 3/2015 | Guichet |
| 9,005,251 B2 | 4/2015 | Heggeness |
| 9,005,293 B2 | 4/2015 | Moskowitz et al. |
| 9,005,298 B2 | 4/2015 | Makower et al. |
| 9,011,491 B2 | 4/2015 | Carl et al. |
| 9,015,057 B2 | 4/2015 | Phillips et al. |
| 9,022,917 B2 | 5/2015 | Kasic et al. |
| 9,028,550 B2 | 5/2015 | Shulock et al. |
| 9,033,957 B2 | 5/2015 | Cadeddu et al. |
| 9,033,988 B2 | 5/2015 | Gephart et al. |
| 9,034,016 B2 | 5/2015 | Panjabi |
| 9,044,218 B2 | 6/2015 | Young |
| 9,060,810 B2 | 6/2015 | Kercher et al. |
| 9,060,844 B2 | 6/2015 | Kagan et al. |
| 9,072,530 B2 | 7/2015 | Mehta et al. |
| 9,072,606 B2 | 7/2015 | Lucas et al. |
| 9,078,703 B2 | 7/2015 | Arnin |
| 9,084,632 B2 | 7/2015 | Orsak et al. |
| 9,089,348 B2 | 7/2015 | Chavarria et al. |
| 9,095,436 B2 | 8/2015 | Boyden et al. |
| 9,095,437 B2 | 8/2015 | Boyden et al. |
| 9,101,422 B2 | 8/2015 | Freid et al. |
| 9,101,427 B2 | 8/2015 | Globerman et al. |
| 9,107,706 B2 | 8/2015 | Alamin et al. |
| 9,113,967 B2 | 8/2015 | Soubeiran |
| 9,114,016 B2 | 8/2015 | Shenoy et al. |
| 9,125,746 B2 | 9/2015 | Clifford et al. |
| 9,138,266 B2 | 9/2015 | Stauch |
| 9,144,482 B2 | 9/2015 | Sayet |
| 9,155,565 B2 | 10/2015 | Boomer et al. |
| 9,161,856 B2 | 10/2015 | Nelson et al. |
| 9,168,071 B2 | 10/2015 | Seme et al. |
| 9,168,076 B2 | 10/2015 | Patty et al. |
| 9,173,681 B2 | 11/2015 | Seme |
| 9,173,715 B2 | 11/2015 | Baumgartner |
| 9,186,158 B2 | 11/2015 | Anthony et al. |
| 9,186,185 B2 | 11/2015 | Hestad et al. |
| 9,198,771 B2 | 12/2015 | Ciupik |
| 9,204,899 B2 | 12/2015 | Buttermann |
| 9,204,908 B2 | 12/2015 | Buttermann |
| 9,220,536 B2 | 12/2015 | Skaggs |
| 9,226,783 B2 | 1/2016 | Brigido |
| 9,242,070 B2 | 1/2016 | Tieu |
| 9,259,243 B2 | 2/2016 | Giger et al. |
| 9,272,159 B2 | 3/2016 | Phillips et al. |
| 9,278,004 B2 | 3/2016 | Shenoy et al. |
| 9,278,046 B2 | 3/2016 | Asfora |
| 9,282,997 B2 | 3/2016 | Hunziker |
| 9,301,792 B2 | 4/2016 | Henniges et al. |
| 9,301,854 B2 | 4/2016 | Moskowitz et al. |
| 9,308,089 B2 | 4/2016 | Vicatos et al. |
| 9,308,387 B2 | 4/2016 | Phillips et al. |
| 9,320,618 B2 | 4/2016 | Schmitz et al. |
| 9,326,728 B2 | 5/2016 | Demir et al. |
| 9,333,009 B2 | 5/2016 | Kroll et al. |
| 9,339,197 B2 | 5/2016 | Griswold et al. |
| 9,339,300 B2 | 5/2016 | Kantelhardt |
| 9,339,307 B2 | 5/2016 | McClintock et al. |
| 9,339,312 B2 | 5/2016 | Doherty et al. |
| 9,358,044 B2 | 6/2016 | Seme et al. |
| 9,364,267 B2 | 6/2016 | Northcutt et al. |
| 9,370,388 B2 | 6/2016 | Globerman et al. |
| 9,393,123 B2 | 7/2016 | Lucas et al. |
| 9,408,644 B2 | 8/2016 | Zahrly et al. |
| 9,421,347 B2 | 8/2016 | Burnett |
| 9,427,267 B2 | 8/2016 | Homeier et al. |
| 9,439,744 B2 | 9/2016 | Forsell |

(56) References Cited

U.S. PATENT DOCUMENTS

| | | |
|---|---|---|
| 9,439,797 B2 | 9/2016 | Baym et al. |
| 9,445,848 B2 | 9/2016 | Anderson et al. |
| 9,451,997 B2 | 9/2016 | Carl et al. |
| 9,456,953 B2 | 10/2016 | Asfora |
| 9,474,612 B2 | 10/2016 | Haaja et al. |
| 9,492,199 B2 | 11/2016 | Orsak et al. |
| 9,492,276 B2 | 11/2016 | Lee et al. |
| 9,498,258 B2 | 11/2016 | Boomer et al. |
| 9,498,366 B2 | 11/2016 | Burnett et al. |
| 9,510,834 B2 | 12/2016 | Burnett et al. |
| 9,532,804 B2 | 1/2017 | Clifford et al. |
| 9,561,062 B2 | 2/2017 | Hayes et al. |
| 9,561,063 B2 | 2/2017 | Reiley |
| 9,572,588 B2 | 2/2017 | Fisher et al. |
| 9,572,746 B2 | 2/2017 | Asfora |
| 9,572,910 B2 | 2/2017 | Messersmith et al. |
| 9,579,110 B2 | 2/2017 | Bojarski et al. |
| 9,579,203 B2 | 2/2017 | Soubeiran |
| 9,603,605 B2 | 3/2017 | Collazo |
| 9,603,713 B2 | 3/2017 | Moskowitz et al. |
| 9,610,161 B2 | 4/2017 | Macoviak et al. |
| 9,622,875 B2 | 4/2017 | Moskowitz et al. |
| 9,642,735 B2 | 5/2017 | Burnett |
| 9,655,651 B2 | 5/2017 | Panjabi |
| 9,668,868 B2 | 6/2017 | Shenoy et al. |
| 9,687,243 B2 | 6/2017 | Burnett et al. |
| 9,687,414 B2 | 6/2017 | Asfora |
| 9,693,867 B2 | 7/2017 | Lucas et al. |
| 9,700,419 B2 | 7/2017 | Clifford et al. |
| 9,700,450 B2 | 7/2017 | Burnett |
| 9,717,537 B2 | 8/2017 | Gordon |
| 9,724,135 B2 | 8/2017 | Koch et al. |
| 9,724,265 B2 | 8/2017 | Asfora |
| 9,730,738 B2 | 8/2017 | Gephart et al. |
| 9,743,969 B2 | 8/2017 | Reiley |
| 9,782,206 B2 | 10/2017 | Mueckter et al. |
| 9,795,410 B2 | 10/2017 | Shenoy et al. |
| 9,814,600 B2 | 11/2017 | Shulock et al. |
| 9,820,789 B2 | 11/2017 | Reiley |
| 9,826,987 B2 | 11/2017 | Keefer et al. |
| 9,833,291 B2 | 12/2017 | Baumgartner |
| 9,848,894 B2 | 12/2017 | Burley et al. |
| 9,848,993 B2 | 12/2017 | Moskowitz et al. |
| 9,861,376 B2 | 1/2018 | Chavarria et al. |
| 9,861,390 B2 | 1/2018 | Hunziker |
| 9,861,404 B2 | 1/2018 | Reiley |
| 9,867,719 B2 | 1/2018 | Moskowitz et al. |
| 2001/0011543 A1 | 8/2001 | Forsell |
| 2002/0019580 A1 | 2/2002 | Lau et al. |
| 2002/0050112 A1 | 5/2002 | Koch et al. |
| 2002/0072758 A1 | 6/2002 | Reo et al. |
| 2002/0164905 A1 | 11/2002 | Bryant |
| 2003/0019498 A1 | 1/2003 | Forsell |
| 2003/0032857 A1 | 2/2003 | Forsell |
| 2003/0040671 A1 | 2/2003 | Somogyi et al. |
| 2003/0066536 A1 | 4/2003 | Forsell |
| 2003/0114731 A1 | 6/2003 | Cadeddu et al. |
| 2003/0144669 A1 | 7/2003 | Robinson |
| 2003/0187447 A1 | 10/2003 | Ferrante et al. |
| 2003/0208212 A1 | 11/2003 | Cigaina |
| 2003/0220643 A1 | 11/2003 | Ferree |
| 2003/0220644 A1 | 11/2003 | Thelen et al. |
| 2004/0006342 A1 | 1/2004 | Altarac et al. |
| 2004/0011137 A1 | 1/2004 | Hnat et al. |
| 2004/0011365 A1 | 1/2004 | Govari et al. |
| 2004/0019353 A1 | 1/2004 | Freid et al. |
| 2004/0023623 A1 | 2/2004 | Stauch et al. |
| 2004/0055610 A1 | 3/2004 | Forsell |
| 2004/0064030 A1 | 4/2004 | Forsell |
| 2004/0068205 A1 | 4/2004 | Zogbi et al. |
| 2004/0092939 A1 | 5/2004 | Freid et al. |
| 2004/0098121 A1 | 5/2004 | Opolski |
| 2004/0116773 A1 | 6/2004 | Furness et al. |
| 2004/0133219 A1 | 7/2004 | Forsell |
| 2004/0138725 A1 | 7/2004 | Forsell |
| 2004/0153106 A1 | 8/2004 | Dudai |
| 2004/0158254 A1 | 8/2004 | Eisermann |
| 2004/0172040 A1 | 9/2004 | Heggeness |
| 2004/0173222 A1 | 9/2004 | Kim |
| 2004/0193266 A1 | 9/2004 | Meyer |
| 2004/0220567 A1 | 11/2004 | Eisermann et al. |
| 2004/0220668 A1 | 11/2004 | Eisermann et al. |
| 2004/0230307 A1 | 11/2004 | Eisermann |
| 2004/0250820 A1 | 12/2004 | Forsell |
| 2004/0260287 A1 | 12/2004 | Ferree |
| 2004/0260319 A1 | 12/2004 | Egle |
| 2005/0002984 A1 | 1/2005 | Byrum et al. |
| 2005/0010301 A1* | 1/2005 | Disilvestro ............ A61B 5/076 623/18.12 |
| 2005/0043802 A1 | 2/2005 | Eisermann et al. |
| 2005/0049617 A1 | 3/2005 | Chatlynne et al. |
| 2005/0055025 A1 | 3/2005 | Zacouto et al. |
| 2005/0055039 A1 | 3/2005 | Burnett et al. |
| 2005/0065529 A1 | 3/2005 | Liu et al. |
| 2005/0070937 A1 | 3/2005 | Jambor et al. |
| 2005/0080427 A1 | 4/2005 | Govari et al. |
| 2005/0080439 A1 | 4/2005 | Carson et al. |
| 2005/0090823 A1 | 4/2005 | Bartimus |
| 2005/0096750 A1 | 5/2005 | Kagan et al. |
| 2005/0119672 A1 | 6/2005 | Benchetrit |
| 2005/0131352 A1 | 6/2005 | Conlon et al. |
| 2005/0159637 A9 | 7/2005 | Nelson et al. |
| 2005/0159754 A1 | 7/2005 | Odrich |
| 2005/0159755 A1 | 7/2005 | Odrich |
| 2005/0165440 A1 | 7/2005 | Cancel et al. |
| 2005/0171543 A1 | 8/2005 | Timm et al. |
| 2005/0177164 A1 | 8/2005 | Walters et al. |
| 2005/0182400 A1 | 8/2005 | White |
| 2005/0182401 A1 | 8/2005 | Timm et al. |
| 2005/0182412 A1 | 8/2005 | Johnson et al. |
| 2005/0192629 A1 | 9/2005 | Saadat et al. |
| 2005/0222489 A1 | 10/2005 | Rahdert et al. |
| 2005/0234289 A1 | 10/2005 | Anstadt et al. |
| 2005/0234448 A1 | 10/2005 | McCarthy |
| 2005/0234462 A1 | 10/2005 | Hershberger |
| 2005/0246034 A1 | 11/2005 | Soubeiran |
| 2005/0251109 A1 | 11/2005 | Soubeiran |
| 2005/0261779 A1 | 11/2005 | Meyer |
| 2005/0272976 A1 | 12/2005 | Tanaka et al. |
| 2005/0288672 A1 | 12/2005 | Ferree |
| 2006/0004447 A1 | 1/2006 | Mastrorio |
| 2006/0004458 A1 | 1/2006 | Hazebrouck |
| 2006/0004459 A1 | 1/2006 | Hazebrouck et al. |
| 2006/0009767 A1 | 1/2006 | Kiester |
| 2006/0020278 A1 | 1/2006 | Burnett et al. |
| 2006/0036251 A1 | 2/2006 | Reiley |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0047282 A1 | 3/2006 | Gordon |
| 2006/0052782 A1 | 3/2006 | Morgan et al. |
| 2006/0058792 A1 | 3/2006 | Hynes |
| 2006/0069447 A1 | 3/2006 | DiSilvestro et al. |
| 2006/0074448 A1 | 4/2006 | Harrison et al. |
| 2006/0079897 A1 | 4/2006 | Harrison et al. |
| 2006/0084043 A1 | 4/2006 | Stevenson |
| 2006/0116757 A1 | 6/2006 | Lashinski et al. |
| 2006/0124140 A1 | 6/2006 | Forsell |
| 2006/0136062 A1 | 6/2006 | DiNello et al. |
| 2006/0142634 A1 | 6/2006 | Anstadt et al. |
| 2006/0142767 A1 | 6/2006 | Green et al. |
| 2006/0155279 A1 | 7/2006 | Ogilvie |
| 2006/0155347 A1 | 7/2006 | Forsell |
| 2006/0184240 A1 | 8/2006 | Jimenez et al. |
| 2006/0184248 A1 | 8/2006 | Edidin et al. |
| 2006/0195087 A1 | 8/2006 | Sacher et al. |
| 2006/0195088 A1 | 8/2006 | Sacher et al. |
| 2006/0195102 A1 | 8/2006 | Malandain |
| 2006/0200134 A1 | 9/2006 | Freid et al. |
| 2006/0204156 A1 | 9/2006 | Takehara et al. |
| 2006/0211909 A1 | 9/2006 | Anstadt et al. |
| 2006/0235299 A1 | 10/2006 | Martinelli |
| 2006/0235424 A1 | 10/2006 | Vitale et al. |
| 2006/0241746 A1 | 10/2006 | Shaoulian et al. |

(56) References Cited

U.S. PATENT DOCUMENTS

| | | |
|---|---|---|
| 2006/0241748 A1 | 10/2006 | Lee et al. |
| 2006/0241767 A1 | 10/2006 | Doty |
| 2006/0249914 A1 | 11/2006 | Dulin |
| 2006/0252983 A1 | 11/2006 | Lembo et al. |
| 2006/0271107 A1 | 11/2006 | Harrison et al. |
| 2006/0276812 A1 | 12/2006 | Hill et al. |
| 2006/0282073 A1 | 12/2006 | Simanovsky |
| 2006/0289014 A1 | 12/2006 | Purdy et al. |
| 2006/0293671 A1 | 12/2006 | Heggeness |
| 2006/0293683 A1 | 12/2006 | Stauch |
| 2007/0010814 A1 | 1/2007 | Stauch |
| 2007/0010887 A1 | 1/2007 | Williams et al. |
| 2007/0015955 A1 | 1/2007 | Tsonton |
| 2007/0021644 A1 | 1/2007 | Woolson et al. |
| 2007/0031131 A1 | 2/2007 | Griffitts |
| 2007/0043376 A1 | 2/2007 | Leatherbury |
| 2007/0050030 A1 | 3/2007 | Kim |
| 2007/0055237 A1 | 3/2007 | Edidin et al. |
| 2007/0055368 A1 | 3/2007 | Rhee et al. |
| 2007/0118215 A1 | 5/2007 | Moaddeb |
| 2007/0135913 A1 | 6/2007 | Moaddeb et al. |
| 2007/0161984 A1 | 7/2007 | Cresina et al. |
| 2007/0162032 A1 | 7/2007 | Johnson et al. |
| 2007/0173837 A1 | 7/2007 | Chan et al. |
| 2007/0173869 A1 | 7/2007 | Gannoe et al. |
| 2007/0179493 A1 | 8/2007 | Kim |
| 2007/0185374 A1 | 8/2007 | Kick et al. |
| 2007/0213751 A1 | 9/2007 | Scirica et al. |
| 2007/0233098 A1 | 10/2007 | Mastrorio et al. |
| 2007/0239159 A1 | 10/2007 | Altarac et al. |
| 2007/0239161 A1 | 10/2007 | Giger et al. |
| 2007/0244488 A1 | 10/2007 | Metzger |
| 2007/0250084 A1 | 10/2007 | Sharkawy et al. |
| 2007/0255088 A1 | 11/2007 | Jacobson et al. |
| 2007/0256693 A1 | 11/2007 | Paraschac et al. |
| 2007/0260270 A1 | 11/2007 | Assell et al. |
| 2007/0264605 A1 | 11/2007 | Belfor et al. |
| 2007/0265646 A1 | 11/2007 | McCoy et al. |
| 2007/0270631 A1 | 11/2007 | Nelson et al. |
| 2007/0270803 A1 | 11/2007 | Giger et al. |
| 2007/0276368 A1 | 11/2007 | Trieu et al. |
| 2007/0276369 A1 | 11/2007 | Allard et al. |
| 2007/0276372 A1 | 11/2007 | Malandain et al. |
| 2007/0276373 A1 | 11/2007 | Malandain |
| 2007/0276378 A1 | 11/2007 | Harrison et al. |
| 2007/0276493 A1 | 11/2007 | Malandain et al. |
| 2007/0288024 A1 | 12/2007 | Gollogly |
| 2007/0288183 A1 | 12/2007 | Bulkes et al. |
| 2008/0009792 A1 | 1/2008 | Henniges et al. |
| 2008/0015577 A1 | 1/2008 | Loeb |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0027436 A1 | 1/2008 | Cournoyer et al. |
| 2008/0033431 A1 | 2/2008 | Jung et al. |
| 2008/0033436 A1 | 2/2008 | Song et al. |
| 2008/0048855 A1 | 2/2008 | Berger |
| 2008/0051784 A1 | 2/2008 | Gollogly |
| 2008/0051895 A1 | 2/2008 | Malandain et al. |
| 2008/0058936 A1 | 3/2008 | Malandain et al. |
| 2008/0058937 A1 | 3/2008 | Malandain et al. |
| 2008/0065077 A1 | 3/2008 | Ferree |
| 2008/0065215 A1 | 3/2008 | Reiley |
| 2008/0066764 A1 | 3/2008 | Paraschac et al. |
| 2008/0071275 A1 | 3/2008 | Ferree |
| 2008/0071276 A1 | 3/2008 | Ferree |
| 2008/0082118 A1 | 4/2008 | Edidin et al. |
| 2008/0082167 A1 | 4/2008 | Edidin et al. |
| 2008/0083413 A1 | 4/2008 | Forsell |
| 2008/0086128 A1 | 4/2008 | Lewis |
| 2008/0091059 A1 | 4/2008 | Machold et al. |
| 2008/0097188 A1 | 4/2008 | Pool et al. |
| 2008/0097249 A1 | 4/2008 | Pool et al. |
| 2008/0097487 A1 | 4/2008 | Pool et al. |
| 2008/0097496 A1 | 4/2008 | Chang et al. |
| 2008/0097523 A1 | 4/2008 | Bolduc et al. |
| 2008/0108995 A1 | 5/2008 | Conway et al. |
| 2008/0140188 A1 | 6/2008 | Randert et al. |
| 2008/0147139 A1 | 6/2008 | Barrett et al. |
| 2008/0147192 A1 | 6/2008 | Edidin et al. |
| 2008/0161933 A1 | 7/2008 | Grotz et al. |
| 2008/0167685 A1 | 7/2008 | Allard et al. |
| 2008/0172063 A1 | 7/2008 | Taylor |
| 2008/0172072 A1 | 7/2008 | Pool et al. |
| 2008/0177319 A1 | 7/2008 | Schwab |
| 2008/0177326 A1 | 7/2008 | Thompson |
| 2008/0190237 A1 | 8/2008 | Radinger et al. |
| 2008/0195156 A1 | 8/2008 | Ainsworth et al. |
| 2008/0226563 A1 | 9/2008 | Contag et al. |
| 2008/0228186 A1 | 9/2008 | Gall et al. |
| 2008/0255615 A1 | 10/2008 | Vittur et al. |
| 2008/0272928 A1 | 11/2008 | Shuster |
| 2008/0275552 A1 | 11/2008 | Makower et al. |
| 2008/0275555 A1 | 11/2008 | Makower et al. |
| 2008/0275557 A1 | 11/2008 | Makower et al. |
| 2008/0275567 A1 | 11/2008 | Makower et al. |
| 2008/0293995 A1 | 11/2008 | Moaddeb et al. |
| 2009/0030462 A1 | 1/2009 | Buttermann |
| 2009/0062825 A1 | 3/2009 | Pool et al. |
| 2009/0076597 A1 | 3/2009 | Dahlgren et al. |
| 2009/0082815 A1 | 3/2009 | Zylber et al. |
| 2009/0088803 A1 | 4/2009 | Justis et al. |
| 2009/0093820 A1 | 4/2009 | Trieu et al. |
| 2009/0093890 A1 | 4/2009 | Gelbart |
| 2009/0112207 A1* | 4/2009 | Walker ............... A61B 17/7016 606/57 |
| 2009/0112262 A1 | 4/2009 | Pool et al. |
| 2009/0112263 A1 | 4/2009 | Pool et al. |
| 2009/0118699 A1 | 5/2009 | Utley et al. |
| 2009/0163780 A1 | 6/2009 | Tieu |
| 2009/0171356 A1 | 7/2009 | Klett |
| 2009/0177203 A1 | 7/2009 | Reiley |
| 2009/0182356 A1 | 7/2009 | Coe |
| 2009/0192514 A1 | 7/2009 | Feinberg et al. |
| 2009/0198144 A1 | 8/2009 | Phillips et al. |
| 2009/0204055 A1 | 8/2009 | Lennox et al. |
| 2009/0206827 A1* | 8/2009 | Aimuta ................. G01D 5/145 324/207.25 |
| 2009/0216113 A1 | 8/2009 | Meier et al. |
| 2009/0216262 A1 | 8/2009 | Burnett et al. |
| 2009/0240173 A1 | 9/2009 | Hsia et al. |
| 2009/0259236 A2 | 10/2009 | Burnett et al. |
| 2009/0270871 A1 | 10/2009 | Liu et al. |
| 2009/0275984 A1 | 11/2009 | Kim |
| 2009/0318919 A1 | 12/2009 | Robinson |
| 2010/0004654 A1 | 1/2010 | Schmitz et al. |
| 2010/0030281 A1 | 2/2010 | Gollogly |
| 2010/0057127 A1 | 3/2010 | McGuire et al. |
| 2010/0081868 A1 | 4/2010 | Moaddeb et al. |
| 2010/0094302 A1 | 4/2010 | Pool |
| 2010/0094303 A1 | 4/2010 | Chang et al. |
| 2010/0094304 A1 | 4/2010 | Pool |
| 2010/0094305 A1 | 4/2010 | Chang et al. |
| 2010/0094306 A1 | 4/2010 | Chang et al. |
| 2010/0100185 A1 | 4/2010 | Trieu et al. |
| 2010/0106192 A1 | 4/2010 | Barry |
| 2010/0106193 A1 | 4/2010 | Barry |
| 2010/0114103 A1 | 5/2010 | Harrison et al. |
| 2010/0114322 A1 | 5/2010 | Clifford et al. |
| 2010/0121323 A1* | 5/2010 | Pool .................... A61B 17/7004 606/54 |
| 2010/0121457 A1 | 5/2010 | Clifford et al. |
| 2010/0130941 A1 | 5/2010 | Conlon et al. |
| 2010/0137872 A1 | 6/2010 | Kam et al. |
| 2010/0145449 A1 | 6/2010 | Makower et al. |
| 2010/0145462 A1 | 6/2010 | Ainsworth et al. |
| 2010/0168751 A1 | 7/2010 | Anderson et al. |
| 2010/0179601 A1 | 7/2010 | Jung et al. |
| 2010/0198261 A1 | 8/2010 | Trieu et al. |
| 2010/0228167 A1 | 9/2010 | Ilovich et al. |
| 2010/0241168 A1 | 9/2010 | Franck et al. |
| 2010/0249782 A1 | 9/2010 | Durham |
| 2010/0249839 A1 | 9/2010 | Alamin et al. |
| 2010/0249847 A1 | 9/2010 | Jung et al. |

(56) References Cited

U.S. PATENT DOCUMENTS

| | | |
|---|---|---|
| 2010/0256626 A1 | 10/2010 | Muller et al. |
| 2010/0262160 A1 | 10/2010 | Boyden et al. |
| 2010/0262239 A1* | 10/2010 | Boyden .................. A61B 17/68 623/16.11 |
| 2010/0274290 A1 | 10/2010 | Jung et al. |
| 2010/0286730 A1 | 11/2010 | Gordon |
| 2010/0286791 A1 | 11/2010 | Goldsmith |
| 2010/0318129 A1 | 12/2010 | Seme et al. |
| 2010/0324684 A1 | 12/2010 | Eisermann et al. |
| 2010/0331883 A1 | 12/2010 | Schmitz et al. |
| 2011/0004076 A1 | 1/2011 | Janna et al. |
| 2011/0057756 A1 | 3/2011 | Marinescu et al. |
| 2011/0060421 A1* | 3/2011 | Martin ...................... A61F 2/68 623/34 |
| 2011/0060422 A1 | 3/2011 | Makower et al. |
| 2011/0066188 A1 | 3/2011 | Seme et al. |
| 2011/0098748 A1 | 4/2011 | Jangra |
| 2011/0130702 A1 | 6/2011 | Stergiopulos |
| 2011/0137415 A1 | 6/2011 | Clifford et al. |
| 2011/0152725 A1 | 6/2011 | Demir et al. |
| 2011/0184505 A1 | 7/2011 | Sharkawy et al. |
| 2011/0196371 A1 | 8/2011 | Forsell |
| 2011/0196435 A1 | 8/2011 | Forsell |
| 2011/0202138 A1 | 8/2011 | Shenoy et al. |
| 2011/0237861 A1 | 9/2011 | Pool et al. |
| 2011/0238126 A1 | 9/2011 | Soubeiran |
| 2011/0257655 A1 | 10/2011 | Copf, Jr. |
| 2011/0275879 A1 | 11/2011 | Nelson et al. |
| 2011/0284014 A1 | 11/2011 | Cadeddu et al. |
| 2012/0004494 A1* | 1/2012 | Payne ...................... A61F 5/02 600/9 |
| 2012/0019341 A1 | 1/2012 | Gabay et al. |
| 2012/0019342 A1 | 1/2012 | Gabay et al. |
| 2012/0053633 A1 | 3/2012 | Stauch |
| 2012/0088953 A1 | 4/2012 | King |
| 2012/0089186 A1 | 4/2012 | Carl et al. |
| 2012/0089191 A1 | 4/2012 | Altarac et al. |
| 2012/0109207 A1 | 5/2012 | Trieu |
| 2012/0116522 A1 | 5/2012 | Makower et al. |
| 2012/0116535 A1 | 5/2012 | Ratron et al. |
| 2012/0130426 A1 | 5/2012 | Thompson |
| 2012/0136449 A1 | 5/2012 | Makower et al. |
| 2012/0157996 A1 | 6/2012 | Walker et al. |
| 2012/0158061 A1 | 6/2012 | Koch et al. |
| 2012/0172883 A1 | 7/2012 | Sayago |
| 2012/0179215 A1 | 7/2012 | Soubeiran |
| 2012/0179273 A1 | 7/2012 | Clifford et al. |
| 2012/0185040 A1 | 7/2012 | Rahdert et al. |
| 2012/0203282 A1 | 8/2012 | Sachs et al. |
| 2012/0221101 A1 | 8/2012 | Moaddeb et al. |
| 2012/0221106 A1 | 8/2012 | Makower et al. |
| 2012/0271353 A1 | 10/2012 | Barry |
| 2012/0277747 A1 | 11/2012 | Keller |
| 2012/0283781 A1 | 11/2012 | Arnin |
| 2012/0296234 A1 | 11/2012 | Wilhelm et al. |
| 2012/0312307 A1 | 12/2012 | Paraschac et al. |
| 2012/0329882 A1 | 12/2012 | Messersmith et al. |
| 2013/0013066 A1 | 1/2013 | Landry et al. |
| 2013/0018468 A1 | 1/2013 | Moskowitz et al. |
| 2013/0018469 A1 | 1/2013 | Moskowitz et al. |
| 2013/0023991 A1 | 1/2013 | Moskowitz et al. |
| 2013/0072932 A1 | 3/2013 | Stauch |
| 2013/0079830 A1 | 3/2013 | Garamszegi et al. |
| 2013/0085408 A1 | 4/2013 | Pool |
| 2013/0123847 A1 | 5/2013 | Anderson et al. |
| 2013/0138017 A1 | 5/2013 | Jundt et al. |
| 2013/0138154 A1 | 5/2013 | Reiley |
| 2013/0150709 A1 | 6/2013 | Baumgartner |
| 2013/0150863 A1 | 6/2013 | Baumgartner |
| 2013/0150889 A1 | 6/2013 | Fening et al. |
| 2013/0178903 A1 | 7/2013 | Abdou |
| 2013/0197639 A1 | 8/2013 | Clifford et al. |
| 2013/0204266 A1 | 8/2013 | Heilman |
| 2013/0204376 A1 | 8/2013 | DiSilvestro et al. |
| 2013/0211521 A1 | 8/2013 | Shenoy et al. |
| 2013/0238094 A1 | 9/2013 | Voellmicke et al. |
| 2013/0245692 A1 | 9/2013 | Hayes et al. |
| 2013/0253344 A1 | 9/2013 | Griswold et al. |
| 2013/0253587 A1 | 9/2013 | Carls et al. |
| 2013/0261623 A1 | 10/2013 | Voellmicke et al. |
| 2013/0261672 A1 | 10/2013 | Horvath |
| 2013/0296863 A1 | 11/2013 | Globerman et al. |
| 2013/0296864 A1 | 11/2013 | Burley et al. |
| 2013/0296940 A1 | 11/2013 | Northcutt et al. |
| 2013/0325006 A1 | 12/2013 | Michelinie et al. |
| 2013/0325071 A1 | 12/2013 | Niemiec et al. |
| 2013/0331889 A1 | 12/2013 | Alamin et al. |
| 2013/0345802 A1 | 12/2013 | Cartledge et al. |
| 2014/0005788 A1 | 1/2014 | Haaja et al. |
| 2014/0018913 A1 | 1/2014 | Cartledge et al. |
| 2014/0025172 A1 | 1/2014 | Lucas et al. |
| 2014/0031826 A1 | 1/2014 | Bojarski et al. |
| 2014/0031929 A1 | 1/2014 | Cartledge et al. |
| 2014/0039558 A1 | 2/2014 | Alamin et al. |
| 2014/0051914 A1 | 2/2014 | Fobi et al. |
| 2014/0052134 A1 | 2/2014 | Orisek |
| 2014/0058392 A1 | 2/2014 | Mueckter et al. |
| 2014/0058450 A1 | 2/2014 | Arlet |
| 2014/0066987 A1 | 3/2014 | Hestad et al. |
| 2014/0067075 A1 | 3/2014 | Makower et al. |
| 2014/0080203 A1 | 3/2014 | Wan et al. |
| 2014/0088715 A1 | 3/2014 | Ciupik |
| 2014/0107704 A1 | 4/2014 | Serhan et al. |
| 2014/0128920 A1 | 5/2014 | Kantelhardt |
| 2014/0135838 A1 | 5/2014 | Alamin et al. |
| 2014/0142631 A1 | 5/2014 | Hunziker |
| 2014/0142698 A1 | 5/2014 | Landry et al. |
| 2014/0156004 A1 | 6/2014 | Shenoy et al. |
| 2014/0163664 A1 | 6/2014 | Goldsmith |
| 2014/0172097 A1 | 6/2014 | Clifford et al. |
| 2014/0194932 A1 | 7/2014 | Bruneau et al. |
| 2014/0222138 A1 | 8/2014 | Machold et al. |
| 2014/0236234 A1 | 8/2014 | Kroll et al. |
| 2014/0236311 A1 | 8/2014 | Vicatos et al. |
| 2014/0257412 A1 | 9/2014 | Patty et al. |
| 2014/0263552 A1* | 9/2014 | Hall .................. A61B 17/07207 227/176.1 |
| 2014/0277446 A1 | 9/2014 | Clifford et al. |
| 2014/0296918 A1 | 10/2014 | Fening et al. |
| 2014/0303538 A1 | 10/2014 | Baym et al. |
| 2014/0303539 A1 | 10/2014 | Baym et al. |
| 2014/0303540 A1 | 10/2014 | Baym et al. |
| 2014/0324047 A1 | 10/2014 | Zahrly et al. |
| 2014/0336756 A1 | 11/2014 | Lee et al. |
| 2014/0358150 A1 | 12/2014 | Kaufman et al. |
| 2015/0013687 A1 | 1/2015 | Paraschac et al. |
| 2015/0057490 A1 | 2/2015 | Forsell |
| 2015/0073565 A1 | 3/2015 | Nelson et al. |
| 2015/0105782 A1 | 4/2015 | D'Lima et al. |
| 2015/0105824 A1 | 4/2015 | Moskowitz et al. |
| 2015/0132174 A1 | 5/2015 | Marinescu et al. |
| 2015/0134007 A1 | 5/2015 | Alamin et al. |
| 2015/0142110 A1 | 5/2015 | Myers et al. |
| 2015/0150561 A1 | 6/2015 | Burnett et al. |
| 2015/0157364 A1 | 6/2015 | Hunziker |
| 2015/0272600 A1 | 10/2015 | Mehta et al. |
| 2015/0313649 A1 | 11/2015 | Alamin et al. |
| 2015/0313745 A1 | 11/2015 | Cheng |

FOREIGN PATENT DOCUMENTS

| | | |
|---|---|---|
| CN | 101040807 | 9/2007 |
| DE | 1541262 | 6/1969 |
| DE | 1541262 A1 | 6/1969 |
| DE | 1541262 B2 | 2/1976 |
| DE | 8515687 U1 | 10/1985 |
| DE | 8515687 | 12/1985 |
| DE | 68515687.6 | 12/1985 |
| DE | 19626230 | 1/1998 |
| DE | 19751733 | 12/1998 |
| DE | 19745654 | 4/1999 |
| DE | 102005045070 | 4/2007 |
| DE | 102007053362 | 5/2009 |
| EP | 0663184 | 7/1995 |

(56) References Cited

FOREIGN PATENT DOCUMENTS

| | | |
|---|---|---|
| EP | 1547549 | 6/2005 |
| EP | 1547549 A2 | 6/2005 |
| EP | 1547549 A3 | 8/2005 |
| EP | 1745765 | 1/2007 |
| EP | 1745765 A2 | 1/2007 |
| EP | 1905388 | 4/2008 |
| EP | 1905388 A1 | 4/2008 |
| EP | 1745765 A3 | 6/2008 |
| EP | 1547549 B1 | 8/2009 |
| EP | 1905388 B1 | 1/2012 |
| FR | 2802406 | 6/2001 |
| FR | 2823663 | 10/2002 |
| FR | 2827756 | 1/2003 |
| FR | 2892617 | 5/2007 |
| FR | 2900563 | 11/2007 |
| FR | 2901991 | 12/2007 |
| FR | 2916622 | 12/2008 |
| FR | 2961386 | 12/2011 |
| GB | 1174814 | 12/1969 |
| HU | 223454 | 4/2002 |
| JP | 05-104022 | 4/1993 |
| JP | 09-056736 | 3/1997 |
| JP | 2001-507608 | 6/2001 |
| JP | 2002500063 A | 1/2002 |
| JP | 2003-172372 | 6/2003 |
| JP | 2003-530195 | 10/2003 |
| JP | 2007-050339 | 3/2007 |
| JP | 2011502003 A | 1/2011 |
| WO | WO8604498 | 8/1986 |
| WO | WO8707134 | 12/1987 |
| WO | WO8906940 | 8/1989 |
| WO | WO9601597 | 1/1996 |
| WO | WO9808454 | 3/1998 |
| WO | WO9830163 | 7/1998 |
| WO | WO1998044858 | 10/1998 |
| WO | WO9850309 | 11/1998 |
| WO | WO9903348 | 1/1999 |
| WO | WO9923744 | 5/1999 |
| WO | 99/34746 | 7/1999 |
| WO | WO9951160 | 10/1999 |
| WO | WO1999051160 | 10/1999 |
| WO | WO9963907 | 12/1999 |
| WO | WO0000108 | 1/2000 |
| WO | WO0072768 | 12/2000 |
| WO | WO0105463 | 1/2001 |
| WO | WO0112108 | 2/2001 |
| WO | WO0124742 | 4/2001 |
| WO | WO2001024697 | 4/2001 |
| WO | WO0141671 | 6/2001 |
| WO | WO0145485 | 6/2001 |
| WO | WO0145487 | 6/2001 |
| WO | WO0145597 | 6/2001 |
| WO | WO0158390 | 8/2001 |
| WO | WO0167973 | 9/2001 |
| WO | WO0178614 | 10/2001 |
| WO | WO0236975 | 5/2002 |
| WO | WO03059215 | 7/2003 |
| WO | WO2004014245 | 2/2004 |
| WO | 2004017705 A2 | 3/2004 |
| WO | WO2004019796 | 3/2004 |
| WO | WO2004021870 | 3/2004 |
| WO | WO2004043280 | 5/2004 |
| WO | WO2005023090 | 3/2005 |
| WO | WO2005072195 | 8/2005 |
| WO | WO2005072664 | 8/2005 |
| WO | WO2005105001 | 11/2005 |
| WO | WO2006019520 | 2/2006 |
| WO | WO2006019521 | 2/2006 |
| WO | WO2006089085 | 8/2006 |
| WO | WO2006090380 | 8/2006 |
| WO | WO2006103071 | 10/2006 |
| WO | WO2006103074 | 10/2006 |
| WO | WO2006105084 | 10/2006 |
| WO | WO2007013059 | 2/2007 |
| WO | WO2007015239 | 2/2007 |
| WO | WO2007025191 | 3/2007 |
| WO | WO2007048012 | 4/2007 |
| WO | WO2007081304 | 7/2007 |
| WO | WO2007118179 | 10/2007 |
| WO | WO2007140180 | 12/2007 |
| WO | WO2007149555 | 12/2007 |
| WO | WO20071144489 | 12/2007 |
| WO | WO2008003952 | 1/2008 |
| WO | WO2008013623 | 1/2008 |
| WO | WO2008015679 | 2/2008 |
| WO | WO2008040880 | 4/2008 |
| WO | WO2008140756 | 11/2008 |
| WO | 2009058546 A1 | 7/2009 |
| WO | WO2010017649 | 2/2010 |
| WO | WO2010050891 | 5/2010 |
| WO | WO2010056650 | 5/2010 |
| WO | WO2011018778 | 2/2011 |
| WO | WO2011116158 | 9/2011 |
| WO | WO2013119528 | 8/2013 |
| WO | WO2013181329 | 12/2013 |
| WO | WO2014040013 | 3/2014 |
| WO | 2014070681 A1 | 5/2014 |
| WO | 2014070681 A1 | 8/2014 |
| WO | WO2011041398 | 4/2015 |

OTHER PUBLICATIONS

PCT Search Report and Written Opinion in PCT Application No. PCT/US2015/028079 dated Jul. 28, 2015 in 16 pages.

Abe, Jun, Kensei Nagata, Mamoru Ariyoshi, and Akio Inoue. "Experimental external fixation combined with percutaneous discectomy in the management of scoliosis." Spine 24, No. 7 (1999): 646-653.

Amer, A. R. A. L., and Ashraf A. Khanfour. "Evaluation of treatment of late-onset tibia vara using gradual angulationtranslation high tibial osteotomy." Acta orthopaedica Belgica 76, No. 3 (2010): 360.

Angrisani, L., F. Favretti, F. Furbetta, S. Gennai, G. Segato, V. Borrelli, A. Sergio, T. Lafullarde, G. Vander Velpen, and M Lorenzo. "Lap-Band ((R)) Rapid Port (TM) System: Preliminary results in 21 patients." In Obesity Surgery, vol. 15, No. 7,pp. 936-936.

Baumgart, Rainer, Stefan Hinterwimmer, Michael Krammer, Oliver Muensterer, and Wolf Mutschler. "The bioexpandable prosthesis: a new perspective after resection of malignant bone tumors in children." Journal of pediatric hematology/oncology 27, No. 8 (2005): 452-455.

Baumgart, R., P. Thaller, S. Hinterwimmer, M. Krammer, T. Hierl, and W. Mutschler. "A fully implantable, programmable distraction nail (Fitbone)—new perspectives for corrective and reconstructive limb surgery." In Practice of Intramedullary Locked Nails, pp. 189-198. Springer Berlin Heidelberg, 2006.

Bodó, László, László Hangody, Balázs Borsitzky, György Béres, Gabriella Arató, Péter Nagy, and Gábor K. Ráthonyi. "Development of a tension-adjustable implant for anterior cruciate ligament reconstruction." Eklem Hast Cerrahisi 19, No. 1 (2008): 27-32.

Boudjemline, Younes, Emmanuelle Pineau, Caroline Bonnet, Alix Mollet, Sylvia Abadir, Damien Bonnet, Daniel Sidi, and Gabriella Agnoletti. "Off-label use of an adjustable gastric banding system for pulmonary artery banding." The Journal of thoracic and cardiovascular surgery 131, No. 5 (2006): 1130-1135.

Brochure-VEPTR II Technique Guide Apr. 2008.

Brochure-VEPTR Patient Guide dated Feb. 2005.

Brown, S. "Single Port Surgery and the Dundee Endocone." SAGES Annual Scientific Sessions, Poster Abstracts (2007): 323-324.

Buchowski, Jacob M., Rishi Bhatnagar, David L. Skaggs, and Paul D. Sponseller. "Temporary internal distraction as an aid to correction of severe scoliosis." The Journal of Bone & Joint Surgery 88, No. 9 (2006): 2035-2041.

Burghardt, R. D., J. E. Herzenberg, S. C. Specht, and D. Paley. "Mechanical failure of the Intramedullary Skeletal Kinetic Distractor in limb lengthening." Journal of Bone & Joint Surgery, British vol. 93, No. 5 (2011): 639-643.

Burke, John Gerard. "Design of a minimally invasive non fusion device for the surgical management of scoliosis in the skeletally immature." Studies in health technology and informatics 123 (2005): 378-384.

(56) References Cited

OTHER PUBLICATIONS

Carter, D. R., and W. E. Caler. "A cumulative damage model for bone fracture." Journal of Orthopaedic Research 3, No. 1 (1985): 84-90.
Chapman, Andrew E., George Kiroff, Philip Game, Bruce Foster, Paul O'Brien, John Ham, and Guy J. Maddern. "Laparoscopic adjustable gastric banding in the treatment of obesity: a systematic literature review." Surgery 135, No. 3 (2004): 326-351.
Cole, J. Dean, Daniel Justin, Tagus Kasparis, Derk DeVlught, and Carl Knobloch. "The intramedullary skeletal distractor (ISKD): first clinical results of a new intramedullary nail for lengthening of the femur and tibia." Injury 32 (2001):129-139.
Cole, J., D. Paley, and M. Dahl. "Operative Technique. ISKD. Intramedullary Skeletal Kinetic Distractor. Tibial Surgical Technique." IS-0508 (A)-OPT-US © Orthofix Inc 28 (2005).
Dailey, Hannah L., Charles J. Daly, John G. Galbraith, Michael Cronin, and James A. Harty. "A novel intramedullary nail for micromotion stimulation of tibial fractures." Clinical Biomechanics 27, No. 2 (2012): 182-188.
Daniels, A. U., Patrick Gemperline, Allen R. Grahn, and Harold K. Dunn. "A new method for continuous intraoperative measurement of Harrington rod loading patterns." Annals of biomedical engineering 12, No. 3 (1984): 233-246.
De Giorgi, G., G. Stella, S. Becchetti, G. Martucci, and D. Miscioscia. "Cotrel-Dubousset instrumentation for the treatment of severe scoliosis." European Spine Journal 8, No. 1 (1999): 8-15.
Dorsey, W. O., Bruce S. Miller, Jared P. Tadje, and Cari R. Bryant. "The stability of three commercially available implants used in medial opening wedge high tibial osteotomy." The journal of knee surgery 19, No. 2 (2006): 95-98.
Edeland, H. G., G. Eriksson, and E. Dahlberg. "Instrumentation for distraction by limited surgery in scoliosis treatment." Journal of biomedical engineering 3, No. 2 (1981): 143-146.
Ember, T., and H. Noordeen. "Distraction forces required during growth rod lengthening." Journal of Bone & Joint Surgery, British vol. 88, No. SUPP II (2006): 229-229.
Fabry, Hans, Robrecht Van Hee, Leo Hendrickx, and Eric Totté. "A technique for prevention of port adjustable silicone gastric banding." Obesity surgery 12, No. 2 (2002): 285-288.
Fried, M., W. Lechner, and K. Kormanova. "In vivo measurements of different gastric band pressures towards the gastric wall at the stoma region." In Obesity Surgery, vol. 14, No. 7, pp. 914-914. 3100 Bayview Ave, Unit 4, Toronto, Ontario M2N 5L3, Canada: F D-Communications Inc, 2004.
Gao, Xiaochong, Derek Gordon, Dongping Zhang, Richard Browne, Cynthia Helms, Joseph Gillum, Samuel Weber et al. "CHD7 gene polymorphisms are associated with susceptibility to idiopathic scoliosis." The American Journal of Human Genetics 80, No. 5 (2007): 957-965.
Gebhart, M., M. Neel, A. Soubeiran, and J. Dubousset. "Early clinical experience with a custom made growing endoprosthesis in children with malignant bone tumors of the lower extremity actioned by an external permanent magnet: the Phenix M system." In International Society of Limb Salvage 14th International Symposium on Limb Salvage.2007.
Gillespie, R., and J. Obrien. "Harrington instrumentation without fusion." In Journal of Bone and Joint Surgerybritish Volume, vol. 63, No. 3, pp. 461-461. 22 Buckingham Street, London, England WC2N 6ET: British Editorial Soc Bone Joint Surgery, 1981.
Goodship, Allen E., James L. Cunningham, and John Kenwright. "Strain rate and timing of stimulation in mechanical modulation of fracture healing." Clinical orthopaedics and related research 355 (1998): S105-S115.
Grass, P. Jose, A. Valentin Soto, and H. Paula Araya. "Intermittent distracting rod for correction of high neurologic risk congenital scoliosis." Spine 22, No. 16 (1997): 1922-1927.
Gray's Anatomy, http://education.yahoo.com/reference/gray/subjects/subject/128, published Jul. 1, 2007.
Grimer, R., S. Carter, R. Tillman, A. Abudu, and L. Jeys. "Non-Invasive Extendable Endoprostheses for Children—Expensive But Worth It!." Journal of Bone & Joint Surgery, British vol. 93, No. SUPP I (2011): 5-5.
Grünert, R. D. "[The development of a totally implantable electronic sphincter]." Langenbecks Archiv fur Chirurgie 325 (1968): 1170-1174.
Guichet, Jean-Marc, Barbara Deromedis, Leo T. Donnan, Giovanni Peretti, Pierre Lascombes, and Flavio Bado. "Gradual femoral lengthening with the Albizzia intramedullary nail." The Journal of Bone & Joint Surgery 85, No. 5 (2003): 838-848.
Gupta, A., J. Meswania, R. Pollock, S. R. Cannon, T. W. R. Briggs, S. Taylor, and G. Blunn. "Non-invasive distal femoral expandable endoprosthesis for limb-salvage surgery in paediatric tumours." Journal of Bone & Joint Surgery, British vol. 88, No. 5 (2006): 649-654.
Hankemeier S, Gösling T, Pape HC, et al. Limb lengthening with the Intramedullary Skeletal Kinetic Distractor (ISKD) Oper Orthop Traumatol. 2005;17:79-101.
Harrington PR (1962) Treatment of scoliosis. Correction and internal fixation by spine instrumentation. J Bone Joint Surg Am 44-A:591-610.
Hazem Elsebaie, M. D. "Single Growing Rods." Changing the Foundations: Does it affect the Results., J Child Orthop. (2007) 1:258.
Hennig, Alex C.; Incavo, Stephen J.; Beynnon, Bruce D.; Abate, Joseph A.; Urse, John S.; Kelly, Stephen / The safety and efficacy of a new adjustable plate used for proximal tibial opening wedge osteotomy in the treatment of unicompartmental knee osteoarthrosis. In: The journal of knee surgery, vol. 20, No. 1, Jan. 1, 2007, p. 6-14.
Hofmeister, M., C. Hierholzer, and V. Bühren. "Callus Distraction with the Albizzia Nail." In Practice of Intramedullary Locked Nails, pp. 211-215. Springer Berlin Heidelberg, 2006.
Horbach, T., D. Herzog, and I. Knerr. "First experiences with the routine use of the Rapid Port (TM) system with the Lap-Band (R)." In Obesity Surgery, vol. 16, No. 4, pp. 418-418. 3100 Bayview Ave, Unit 4, Toronto, Ontario M2N 5L3, Canada: F D-Communications Inc, 2006.
Hyodo, Akira, Helmuth Kotschi, Helen Kambic, and George Muschler. "Bone transport using intramedullary fixation and a single flexible traction cable." Clinical orthopaedics and related research 325 (1996): 256-268.
Ahlbom, A., U. Bergqvist, J. H. Bernhardt, J. P. Cesarini, M. Grandolfo, M. Hietanen, A. F. Mckinlay et al. "Guidelines for limiting exposure to time-varying electric, magnetic, and electromagnetic fields (up to 300 GHz). International Commission on Non-Ionizing Radiation Protection." Health Phys 74, No. 4 (1998): 494-522.
International Commission on Non-Ionizing Radiation Protection. "Guidelines on limits of exposure to static magnetic fields." Health Physics 96, No. 4 (2009): 504-514.
INVIS®/Lamello Catalog, 2006, Article No. 68906A001 GB.
Kasliwal, Manish K., Justin S. Smith, Adam Kanter, Ching-Jen Chen, Praveen V. Mummaneni, Robert A. Hart, and Christopher I. Shaffrey. "Management of high-grade spondylolisthesis." Neurosurgery Clinics of North America 24, No. 2 (2013): 275-291.
Kenawey, Mohamed, Christian Krettek, Emmanouil Liodakis, Ulrich Wiebking, and Stefan Hankemeier. "Leg lengthening using intramedullay skeletal kinetic distractor: results of 57 consecutive applications." Injury 42, No. 2 (2011): 150-155.
Kent, Matthew E., Arvind Arora, P. Julian Owen, and Vikas Khanduja. "Assessment and correction of femoral malrotation following intramedullary nailing of the femur." Acta Orthop Belg 76, No. 5 (2010): 580-4.
Klemme, William R., Francis Denis, Robert B. Winter, John W. Lonstein, and Steven E. Koop. "Spinal instrumentation without fusion for progressive scoliosis in young children." Journal of Pediatric Orthopaedics 17, No. 6 (1997): 734-742.
Korenkov, M., S. Sauerland, N. Yücel, L. Köhler, P. Goh, J. Schierholz, and H. Troidl. "Port function after laparoscopic adjustable gastric banding for morbid obesity." Surgical Endoscopy and Other Interventional Techniques 17, No. 7 (2003): 1068-1071.

(56) References Cited

OTHER PUBLICATIONS

Krieg, Andreas H., Bernhard M. Speth, and Bruce K. Foster. "Leg lengthening with a motorized nail in adolescents." Clinical orthopaedics and related research 466, No. 1 (2008): 189-197.
Kucukkaya, Metin, Raffi Armagan, and Unal Kuzgun. "The new intramedullary cable bone transport technique." Journal of orthopaedic trauma 23, No. 7 (2009): 531-536.
Lechner, W. L., W. Kirchmayr, and G. Schwab. "In vivo band manometry: a new method in band adjustment." In Obesity Surgery, vol. 15, No. 7, pp. 935-935. 3100 Bayview Ave, Unit 4, Toronto, Ontario M2N 5L3, Canada: F DCOMMUNICATIONSINC, 2005.
Lechner, W., M. Gadenstatter, R. Ciovica, W. Kirchmayer, and G. Schwab. "Intra-band manometry for band adjustments: The basics." In Obesity Surgery, vol. 16, No. 4, pp. 417-418. 3100 Bayview Ave, Unit 4, Toronto, Ontario M2N 5L3, Canada: F D-Communications Inc, 2006.
Li, G., S. Berven, N. A. Athanasou, and A. H. R. W. Simpson. "Bone transport over an intramedullary nail: A case report with histologic examination of the regenerated segment." Injury 30, No. 8 (1999): 525-534.
Lonner, Baron S. "Emerging minimally invasive technologies for the management of scoliosis." Orthopedic Clinics of North America 38, No. 3 (2007): 431-440.
Teli, Marco MD. "Measurement of Forces Generated During Distraction of Growing Rods, J." Marco Teli. Journal of Child Orthop 1 (2007): 257-258.
Matthews, Michael Wayne, Harry Conrad Eggleston, Steven D. Pekarek, and Greg Eugene Hilmas. "Magnetically adjustable intraocular lens." Journal of Cataract & Refractive Surgery 29, No. 11 (2003): 2211-2216.
Micromotion "Micro Drive Engineering•General catalogue" pp. 14•24; Jun. 2009.
Mineiro, Jorge, and Stuart L. Weinstein. "Subcutaneous rodding for progressive spinal curvatures: early results." Journal of Pediatric Orthopaedics 22, No. 3 (2002): 290-295.
Moe, John H., Khalil Kharrat, Robert B. Winter, and John L. Cummine. "Harrington instrumentation without fusion plus external orthotic support for the treatment of difficult curvature problems in young children." Clinical orthopaedics and related research 185 (1984): 35-45.
Montague, R. G., C. M. Bingham, and K. Atallah. "Magnetic gear dynamics for servo control." in Melecon 2010-2010 15th IEEE Mediterranean Electrotechnical Conference, pp. 1192-1197. IEEE, 2010.
Montague, Ryan, Chris Bingham, and Kais Atallah. "Servo control of magnetic gears." Mechatronics, IEEE/ASME Transactions on 17, No. 2 (2012): 269-278.
Nachemson, Alf, and Gösta Elfström. "Intravital wireless telemetry of axial forces in Harrington distraction rods in patients with idiopathic scoliosis." The Journal of Bone & Joint Surgery 53, No. 3 (1971): 445-465.
Nachlas, I. William, and Jesse N. Borden. "The cure of experimental scoliosis by directed growth control." The Journal of Bone & Joint Surgery 33, No. 1 (1951): 24-34.
Newton, P. "Fusionless Scoliosis Correction by Anterolateral Tethering . . . Can it Work?." In 39th Annual Scoliosis Research Society Meeting. 2004.
Observations by a third party under Article 115 EPC issued by the European Patent Office dated Feb. 15, 2010 in European Patent Application No. 08805612.2, Applicant: Soubeiran, Arnaud (7 pages).
Oh, Chang-Wug, Hae-Ryong Song, Jae-Young Roh, Jong-Keon Oh, Woo-Kie Min, Hee-Soo Kyung, Joon-Woo Kim, Poong-Taek Kim, and Joo-Chul Ihn. "Bone transport over an intramedullary nail for reconstruction of long bone defects in tibia." Archives of orthopaedic and trauma surgery 128, No. 8 (2008): 801-808.
Ozcivici, Engin, Yen Kim Luu, Ben Adler, Yi-Xian Qin, Janet Rubin, Stefan Judex, and Clinton T. Rubin. "Mechanical signals as anabolic agents in bone." Nature Reviews Rheumatology 6, No. 1 (2010): 50-59.

Patient Guide, VEPTR Vertical Expandable Prosthetic Titanium Rib, Synthes Spine (2005) (23pages).
Piorkowski, James R., Scott J. Ellner, Arun A. Mavanur, and Carlos A. Barba. "Preventing port site inversion in laparoscopic adjustable gastric banding." Surgery for Obesity and Related Diseases 3, No. 2 (2007): 159-161.
Prontes, Isabel, http://wwwehow.com/about_4795793_longest-bone-body.html, published Jun. 12, 2012.
Rathjen, Karl, Megan Wood, Anna McClung, and Zachary Vest. "Clinical and radiographic results after implant removal in idiopathic scoliosis." Spine 32, No. 20 (2007): 2184-2188.
Ren, Christine J., and George A. Fielding. "Laparoscopic adjustable gastric banding: surgical technique." Journal of Laparoendoscopic & Advanced Surgical Techniques 13, No. 4 (2003): 257-263.
Reyes-Sánchez, Alejandro, Luis Miguel Rosales, and Víctor Miramontes. "External fixation for dynamic correction of severe scoliosis." The Spine Journal 5, No. 4 (2005): 418-426.
Rinsky, Lawrence A., James G. Gamble, and Eugene E. Bleck. "Segmental Instrumentation Without Fusion in Children With Progressive Scoliosis." Journal of Pediatric Orthopedics 5, No. 6 (1985): 687-690.
Rode, V., F. Gay, A. J. Baraza, and J. Dargent. "A simple way to adjust bands under radiologic control." In Obesity Surgery, vol. 16, No. 4, pp. 418-418. 3100 Bayview Ave, Unit 4, Toronto, Ontario M2N 5L3, Canada: F DCOMMUNICATIONS Inc, 2006.
Schmerling, M. A., M. A. Wilkov, A. E. Sanders, and J. E. Woosley. "Using the shape recovery of nitinol in the Harrington rod treatment of scoliosis." Journal of biomedical materials research 10, No. 6 (1976): 879-892.
Scott, D. J., S. J. Tang, R. Fernandez, R. Bergs, and J. A. Cadeddu. "Transgastric, transcolonic, and transvaginal cholecystectomy using magnetically anchored instruments." In SAGES Meeting, p. P511. 2007.
Sharke, Paul. "The machinery of life." Mechanical Engineering 126, No. 2 (2004): 30.
Shiha, Anis, Mohamed Alam El-Deen, Abdel Rahman Khalifa, and Mohamed Kenawey. "Ilizarov gradual correction of genu varum deformity in adults." Acta Orthop Belg 75 (2009): 784-91.
Simpson, A. H. W. R., H. Shalaby, and G. Keenan. "Femoral lengthening with the intramedullary skeletal kinetic distractor." Journal of Bone & Joint Surgery, British vol. 91, No. 7 (2009): 955-961.
Smith, John T. "The use of growth-sparing instrumentation in pediatric spinal deformity." Orthopedic Clinics of North America 38, No. 4 (2007): 547-552.
Soubeiran, A., M. Gebhart, L. Miladi, J. Griffet, M. Neel, and J. Dubousset. "The Phenix M System. A Mechanical Fully Implanted Lengthening Device Externally Controllable Through the Skin with a Palm Size Permanent Magnet; Applications to Pediatric Orthopaedics." In 6th European Research Conference in Pediatric Orthopaedics. 2006.
Stokes, Oliver M., Elizabeth J. O'Donovan, Dino Samartzis, Cora H. Bow, Keith DK Luk, and Kenneth MC Cheung. Reducing radiation exposure in early-onset scoliosis surgery patients: novel use of ultrasonography to measure lengthening in magnet.
Sun, Zongyang, Katherine L. Rafferty, Mark A. Egbert, and Susan W. Herring. "Masticatory mechanics of a mandibular distraction osteogenesis site: interfragmentary micromovement." Bone 41, No. 2 (2007): 188-196.
Takaso, Masashi, Hideshige Moriya, Hiroshi Kitahara, Shohei Minami, Kazuhisa Takahashi, Keijiro Isobe, Masatsune Yamagata, Yoshinori Otsuka, Yoshinori Nakata, and Masatoshi Inoue. "New remote-controlled growing-rod spinal instrumentation possibly applicable for scoliosis in young children." Journal of orthopaedic science 3, No. 6 (1998): 336-340.
Tello, Carlos A. "Harrington instrumentation without arthrodesis and consecutive distraction program for young children with severe spinal deformities. Experience and technical details." The Orthopedic clinics of North America 25, No. 2 (1994): 333-351.
Thaller, Peter Helmut, Julian Fürmetz, Florian Wolf, Thorsten Eilers, and Wolf Mutschler. "Limb lengthening with fully implantable magnetically actuated mechanical nails (PHENIX®)—Preliminary results." Injury 45 (2014): S60-S65.

(56) References Cited

OTHER PUBLICATIONS

Thompson, George H., Lawrence G. Lenke, Behrooz A. Akbarnia, Richard E. McCarthy, and Robert M. Campbell. "Early onset scoliosis: future directions." The Journal of Bone & Joint Surgery 89, No. suppl 1 (2007): 163-166.

Thonse, Raghuram, John E. Herzenberg, Shawn C. Standard, and Dror Paley. "Limb lengthening with a fully implantable, telescopic, intramedullary nail." Operative Techniques in Orthopedics 15, No. 4 (2005): 355-362.

Trias, A., P. Bourassa, and M. Massoud. "Dynamic loads experienced in correction of idiopathic scoliosis using two types of Harrington rods." Spine 4, No. 3 (1978): 228-235.

Veptr II. Vertical Expandable Prosthetic Titanium Rib II, Technique Guide, Systhes Spine (2008) (40 pages).

Verkerke, G. J., Koops H. Schraffordt, R. P. Veth, H. J. Grootenboer, L. J. De Boer, J. Oldhoff, and A. Postma. "Development and test of an extendable endoprosthesis for bone reconstruction in the leg." The International journal of artificial organs 17, No. 3 (1994): 155-162.

Verkerke, G. J., H. Schraffordt Koops, R. P. H. Veth, J. Oldhoff, H. K. L. Nielsen, H. H. Van den Kroonenberg, H. J. Grootenboer, and F. M. Van Krieken. "Design of a lengthening element for a modular femur endoprosthetic system." Proceedings of the Institution of Mechanical Engineers, Part H: Journal of Engineering in Medicine 203, No. 2 (1989): 97-102.

Verkerke, G. J., H. Schraffordt Koops, R. P. H. Veth, H. H. van den Kroonenberg, H. J. Grootenboer, H. K. L. Nielsen, J. Oldhoff, and A. Postma. "An extendable modular endoprosthetic system for bone tumour management in the leg." Journal of biomedical engineering 12, No. 2 (1990): 91-96.

Weiner, Rudolph A., Michael Korenkov, Esther Matzig, Sylvia Weiner, and Woiteck K. Karcz. "Initial clinical experience with telemetrically adjustable gastric banding." Surgical technology international 15 (2005): 63-69.

Wenger, H. L. "Spine Jack Operation in the Correction of Scoliotic Deformity: A Direct Intrathoracic Attack to Straighten the Laterally Bent Spine: Preliminary Report." Archives of Surgery 83, No. 6 (1961): 901-910.

White III, Augustus A., and Manohar M. Panjabi. "The clinical biomechanics of scoliosis." Clinical orthopaedics and related research 118 (1976): 100-112.

Yonnet, Jean-Paul. "Passive magnetic bearings with permanent magnets." Magnetics, IEEE Transactions on 14, No. 5 (1978): 803-805.

Yonnet, Jean-Paul. "A new type of permanent magnet coupling." Magnetics, IEEE Transactions on 17, No. 6 (1981): 2991-2993.

Zheng, Pan, Yousef Haik, Mohammad Kilani, and Ching-Jen Chen. "Force and torque characteristics for magnetically driven blood pump." Journal of Magnetism and Magnetic Materials 241, No. 2 (2002): 292-302.

L. Angrisani et al., Abstract, "27 Lap-Band(R) Rapid Pod(TM) System: Preliminary Results in 21 Patients," Obesity Surgery, 15:936, 2005 (1 page).

Stokes et al., Abstract, "23. Reducing Radiation Exposure in Early-Onset Scoliosis Patients: Novel use of Ultrasonography to Measure Lengthening in Magnetically-Controlled Growing Rods Prospective Validation Study and Assessment of Clinical Algorithm," Final Program, 20th International Meeting on Advanced Spine Techniques, pp. 80-81, Jul. 10-13, 2013 (4 pages).

* cited by examiner

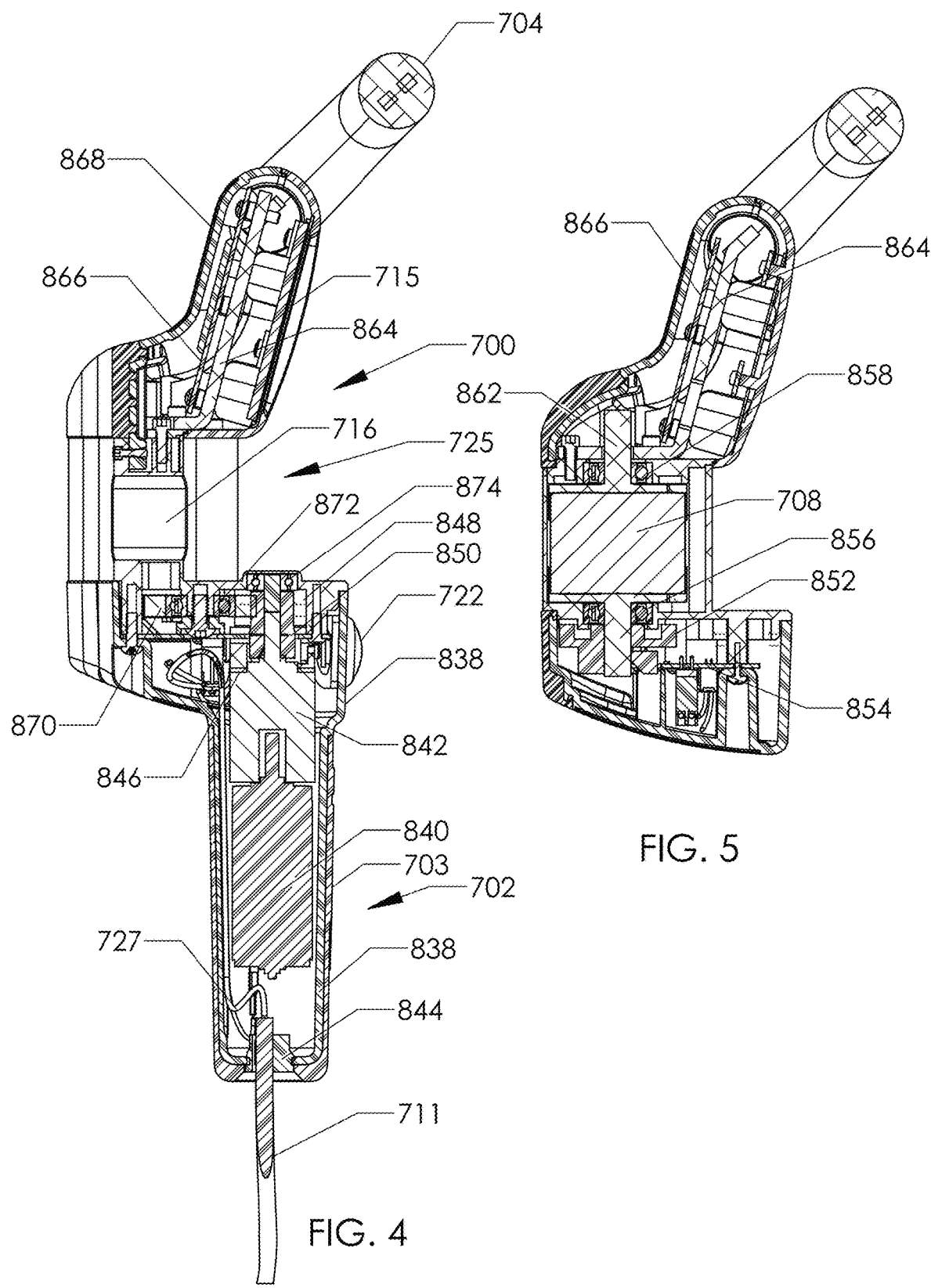

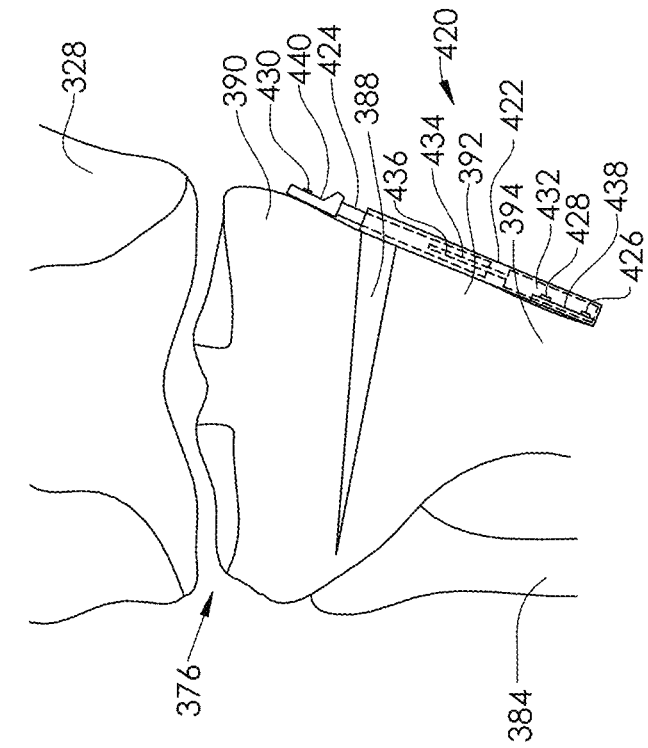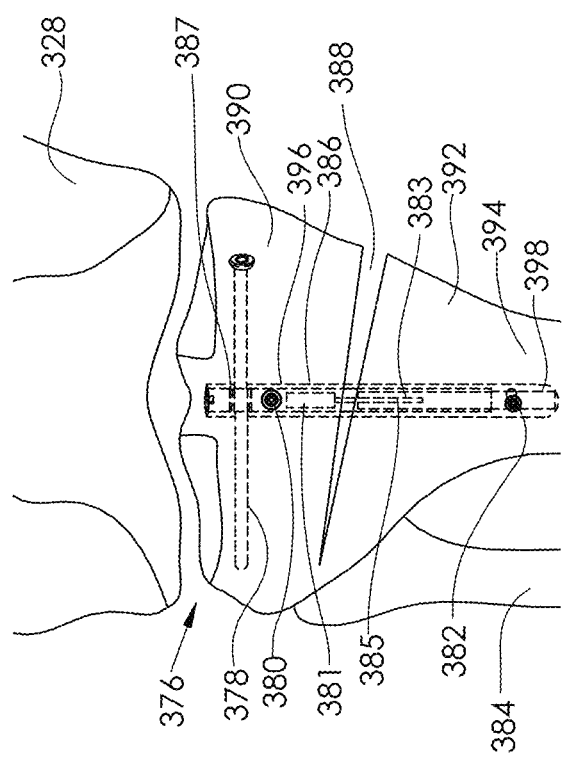

SYSTEM FOR INFORMATIONAL MAGNETIC FEEDBACK IN ADJUSTABLE IMPLANTS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Scoliosis is a general term for the sideways (lateral) curving of the spine, usually in the thoracic or thoracolumbar region. Scoliosis is commonly broken up into different treatment groups, Adolescent Idiopathic Scoliosis, Early Onset Scoliosis and Adult Scoliosis.

Adolescent Idiopathic Scoliosis (AIS) typically affects children between ages 10 and 16, and becomes most severe during growth spurts that occur as the body is developing. One to two percent of children between ages 10 and 16 have some amount of scoliosis. Of every 1000 children, two to five develop curves that are serious enough to require treatment. The degree of scoliosis is typically described by the Cobb angle, which is determined, usually from x-ray images, by taking the most tilted vertebrae above and below the apex of the curved portion and measuring the angle between intersecting lines drawn perpendicular to the top of the top vertebra and the bottom of the bottom vertebra. The term idiopathic refers to the fact that the exact cause of this curvature is unknown. Some have speculated that scoliosis occurs during rapid growth phases when the ligamentum flavum of the spine is too tight and hinders symmetric growth of the spine. For example, as the anterior portion of the spine elongates faster than the posterior portion, the thoracic spine begins to straighten, until it curves laterally, often with an accompanying rotation. In more severe cases, this rotation actually creates a noticeable deformity, in which one shoulder is lower than the other. Currently, many school districts perform external visual assessment of spines, for example in all fifth grade students. For those students in whom an "S" shape or "C" shape is identified, instead of an "I" shape, a recommendation is given to have the spine examined by a physician, and commonly followed-up with periodic spinal x-rays.

Typically, patients with a Cobb angle of 20° or less are not treated, but are periodically monitored, often with subsequent x-rays. Patients with a Cobb angle of 40° or greater are usually recommended for fusion surgery. It should be noted that many patients do not receive this spinal assessment, for numerous reasons. Many school districts do not perform this assessment, and many children do not regularly visit a physician. So, the curve often progresses rapidly and severely. There is a large population of grown adults with untreated scoliosis, in extreme cases with a Cobb angle as high as or greater than 90°. Many of these adults, though, do not experience pain associated with this deformity, and live relatively normal lives, though oftentimes with restricted mobility and motion, In AIS, the ratio of females to males for curves under 10° is about one to one. However, at angles above 30°, females outnumber males by as much as eight to one. Fusion surgery can be performed on AIS patients or on adult scoliosis patients. In a typical posterior fusion surgery, an incision is made down the length of the back and Titanium or stainless steel straightening rods are placed along the curved portion of the spine. These rods are typically secured to the vertebral bodies, for example with hooks or bone screws (e.g., pedicle screws) in a manner that allows the spine to be straightened. Usually the intervertebral disks are removed and bone graft material is placed to create the fusion. If this is autologous material, the bone graft material is harvested from the patient's hip via a separate incision.

Alternatively, the fusion surgery may be performed anteriorly. Lateral and anterior incisions are made for access. Usually, one of the lungs is deflated in order to allow access to the spine. In a less-invasive version of the anterior procedure, instead of a single long incision, approximately five incisions, each about three to four cm long, are made in the intercostal spaces (between the ribs) on one side of the patient. In one version of this minimally invasive surgery, tethers and bone screws are placed and secured to the vertebra on the anterior convex portion of the curve. Clinical trials are being performed that use staples in place of the tether/screw combination. One advantage of this surgery, by comparison to the posterior approach is that the scars from the incisions are not as dramatic, though they are still located in a frequently visible area, (for example when a bathing suit is worn). Staples have experienced difficulty in clinical trials as they tend to pull out of the bone when a critical stress level is reached.

In some cases, after surgery, the patient will wear a protective brace for a few months as the fusing process occurs. Once the patient reaches spinal maturity, it is difficult to remove the rods and associated hardware in a subsequent surgery as the fusion of the vertebra usually incorporates the rods themselves. Standard practice is to leave the implants in for life. With either of these two surgical methods, after fusion, the patient's spine is straight, but depending on how many vertebrae were fused, there are often limitations in the degree of spinal flexibility, both in bending and twisting. As fused patients mature, the fused section can impart large stresses on the adjacent non-fused vertebra, and often other problems, including pain, can occur in these areas, sometimes necessitating further surgery. This tends to be in the lumbar portion of the spine that is prone to problems in aging patients. Many physicians are now interested in fusionless surgery for scoliosis, which may be able to eliminate some of the drawbacks of fusion.

One group of patients in which the spine is especially dynamic is the subset known as Early Onset Scoliosis (EOS), which typically occurs in children before the age of five, and more often in boys than in girls. While this is a comparatively uncommon condition, occurring in only about one or two out of 10,000 children, it can be severe, affecting the normal development of internal organs. Because of the fact that the spines of these children will still grow a large amount after treatment, non-fusion distraction devices known as growing rods and a device known as the VEPTR—Vertical Expandable Prosthetic Titanium Rib ("Titanium Rib") have been developed. These devices are typically adjusted approximately every six months, to match the child's growth, until the child is at least eight years old, sometimes until they are 15 years old. Each adjustment requires a surgical incision to access the adjustable portion of the device. Because the patients may receive the device at an age as young as six months, this treatment may require a large number of surgeries thereby increasing the likelihood of infection for these patients.

The treatment methodology for AIS patients with a Cobb angle between 20° and 40° is controversial. Many physicians prescribe a brace (for example, the Boston Brace), that the patient must wear on their body and under their clothes 18 to 23 hours a day until they become skeletally mature, for example until age 16. Because these patients are all passing through their socially demanding adolescent years, it may be a serious prospect to be forced with the choice of: 1) either wearing a somewhat bulky brace that covers most of the upper body; 2) having fusion surgery that may leave large scars and also limit motion; 3) or doing nothing and running the risk of becoming disfigured and and/or disabled. It is commonly known that patients have hidden their braces, (in order to escape any related embarrassment) for example, in a bush outside of school. Patient compliance with braces has been so problematic that special braces have been designed to sense the body of the patient, and monitor the amount of time per day that the brace is worn. Even so, patients have been known to place objects into unworn braces of this type in order to fool the sensor. In addition with inconsistent patient compliance, many physicians believe that, even when used properly, braces are not effective in curing scoliosis. These physicians may agree that bracing can possibly slow, or even temporarily stop, curve (Cobb angle) progression, but they have noted that the scoliosis progresses rapidly, to a Cobb angle more severe than it was at the beginning of treatment, as soon as the treatment period ends and the brace is no longer worn. Some believe braces to be ineffective because they work only on a portion of the torso, rather than on the entire spine. A prospective, randomized 500 patient clinical trial known as BrAIST (Bracing in Adolescent Idiopathic Scoliosis Trial) is currently enrolling patients. 50% of the patients will be treated using a brace and 50% will simply be monitored. The Cobb angle data will be measured continually up until skeletal maturity, or until a Cobb angle of 50° is reached. Patients who reach a Cobb angle of 50° will likely undergo corrective surgery. Many physicians believe that the BrAIST trial will establish that braces are ineffective. If this is the case, uncertainty regarding how to treat AIS patients having a Cobb angle between 20° and 40° will only become more pronounced. It should be noted that the "20° to 40° " patient population is as much as ten times larger than the "40° and greater" patient population.

Distraction osteogenesis, also known as distraction callotasis and osteodistraction has been used successfully to lengthen long bones of the body. Typically, the bone, if not already fractured, is purposely fractured by means of a corticotomy, and the two segments of bone are gradually distracted apart, thereby allowing new bone to form in the gap. If the distraction rate is too high, there is a risk of nonunion, if the rate is too low, there is a risk that the two segments will completely fuse to each other before the distraction is complete. When the desired length of the bone is achieved using this process, the bone is allowed to consolidate. Distraction osteogenesis applications are mainly focused on the growth of the femur or tibia, but may also osteogenesis is mainly applied to growth of the femur or tibia, but may also include the humerus, the jaw bone (micrognathia), or other bones. Reasons for lengthening or growing bones are multifold and include, but are not limited to: post osteosarcoma bone cancer; cosmetic lengthening (both legs-femur and/or tibia) in short stature or dwarfism/ achondroplasia; lengthening of one limb to match the other (congenital, post-trauma, post-skeletal disorder, prosthetic knee joint); and nonunions.

Distraction osteogenesis using external fixators has been done for many years, but the external fixator can be unwieldy for the patient. It can also be painful, and the patient is subject to the risk of pin track infections, joint stiffness, loss of appetite, depression, cartilage damage and other side effects. Haying the external fixator in place also delays the beginning of rehabilitation.

In response to the shortcomings of external fixator distraction, intramedullary distraction nails have been surgically implanted which are contained entirely within the bone. Some are automatically lengthened via repeated rotation of the patient's limb, which can sometimes be painful to the patient and can often proceed in an uncontrolled fashion. This therefore makes it difficult to follow a strict daily or weekly lengthening regime that avoids nonunion (if too fast) or early consolidation (if too slow). Lower limb distraction may be about one mm per day. Other intramedullary nails have been developed which have an implanted motor that is remotely controlled by an antenna. These devices are designed to be lengthened in a controlled manner, but due to their complexity may not be manufacturable as an affordable commercial product. Others have proposed intramedullary distractors containing an implanted magnet that allows the distraction to be driven electromagnetically by an external stator. Because of the complexity and size of the external stator, this technology has not been reduced to a simple, cost-effective device that can be taken home, to allow patients to do daily lengthenings. Non-invasively (magnetically) adjustable implantable distraction devices have been developed and use clinically in both scoliosis patients and in limb lengthening patients.

Knee osteoarthritis is a degenerative disease of the knee joint that affects a large number of patients, particularly over the age of 40. The prevalence of this disease has increased significantly over the last several decades, attributed partially, but not completely, to the rising age of the population and the increase in obesity. The increase may also be due partially to an increasing number of highly active people within the population. Knee osteoarthritis is caused mainly by long term stresses on the knee that degrade the cartilage covering the articulating surfaces of the bones in the knee joint. Oftentimes, the problem becomes worse after a particular trauma event, but it can also be a hereditary process. Symptoms may include pain, stiffness, reduced range of motion, swelling, deformity, muscle weakness, and several others. Osteoarthritis may include one or more of the three compartments of the knee: the medial compartment of the tibiofemoral joint, the lateral compartment of the tibiofemoral joint, and the patellofemoral joint. In severe cases, partial or total replacement of the knee is performed in order to replace the degraded/diseased portions with new weight bearing surfaces for the knee. These implants are typically made from implant grade plastics, metals, or ceramics. Replacement operations may involve significant post-operative pain and require substantial physical therapy. The recovery period may last weeks or months. Several potential complications of this surgery exist, including deep venous thrombosis, loss of motion, infection and bone fracture. After recovery, surgical patients who have received unicompartmental or total knee replacement must significantly reduce their activity, removing running and high energy sports completely from their lifestyle.

For these reasons, surgeons may attempt to intervene early in order to delay or even preclude knee replacement surgery. Osteotomy surgeries may be performed on the femur or tibia to change the angle between the femur and tibia, thereby adjusting the stresses on the different portions of the knee joint. In closed wedge and closing wedge osteotomy, an angled wedge of bone is removed and the remaining surfaces are fused together to create a new, improved bone angle. In open wedge osteotomy, a cut is made in the bone and the edges of the cut are opened, creating a new angle. Bone graft is often used to fill in the new opened wedge-shaped space, and, often, a plate is attached to the bone with bone screws. Obtaining the correct angle during either of these types of osteotomy is almost always difficult, and even if the result is close to what was desired, there can be a subsequent loss of the correction angle. Other complications experienced with this technique may include nonunion and material failure.

In addition to the many different types of implantable distraction devices that are configured to be non-invasively adjusted, implantable non-invasively adjustable non-distraction devices have also been envisioned, for example, adjustable restriction devices for gastrointestinal disorders such as GERD, obesity, or sphincter laxity (such as in fecal incontinence), or other disorders such as sphincter laxity in urinary incontinence. These devices too may incorporate magnets to enable the non-invasive adjustment.

SUMMARY

In some embodiments, a remote control for adjusting a medical implant includes a driver, at least one sensor, and an output. The driver is configured to transmit a wireless drive signal to adjust an implanted medical implant. Adjustment of the medical implant includes one or more of generating a force with the medical implant and changing a dimension of the medical implant. The at least one sensor is configured to sense a response of the implant to the drive signal. The output is configured to report one or more of a force generated by the medical implant and a change in dimension of the medical implant, in response to the drive signal. In some embodiments, the output is a visual output (e.g., a display), an audio output (e.g., a speaker, alarm), a USB output, a Bluetooth output, a solid state memory output (e.g., any removable or readable solid state memory), etc, In some embodiments, a medical implant for wireless adjustment of a dimension within a body includes a first portion that is configured for coupling to a first location in the body, a second portion that is configured for coupling to a second location in the body, and a magnetic drive that is configured to adjust a relative distance between the first portion and the second portion. The magnetic drive includes at least one driven magnet and is configured to revolve about an axis in response to a magnetic field imposed by a rotatable driver magnet outside of the body. The implant is configured to transmit a signal indicative of the responsiveness of the driven magnet to movement of the driver magnet, wherein a change in the responsiveness is indicative of a change in a force applied by the body to the first and second connectors.

BRIEF DESCRIPTION OF THE DRAWINGS

FIG. 4 illustrates a sectional view of the external adjustment device of FIG. 3 taken along line 4-4 of FIG. 3.

FIG. 5 illustrates a sectional view of the external adjustment device of FIG. 3 taken along line 5-5 of FIG. 3.

FIG. 29 is an embodiment of an adjustable implant for adjusting an angle or force between sections of bone.

FIG. 30 is an embodiment of an adjustable implant for adjusting an angle or force between sections of bone.

DETAILED DESCRIPTION

Figure 1:
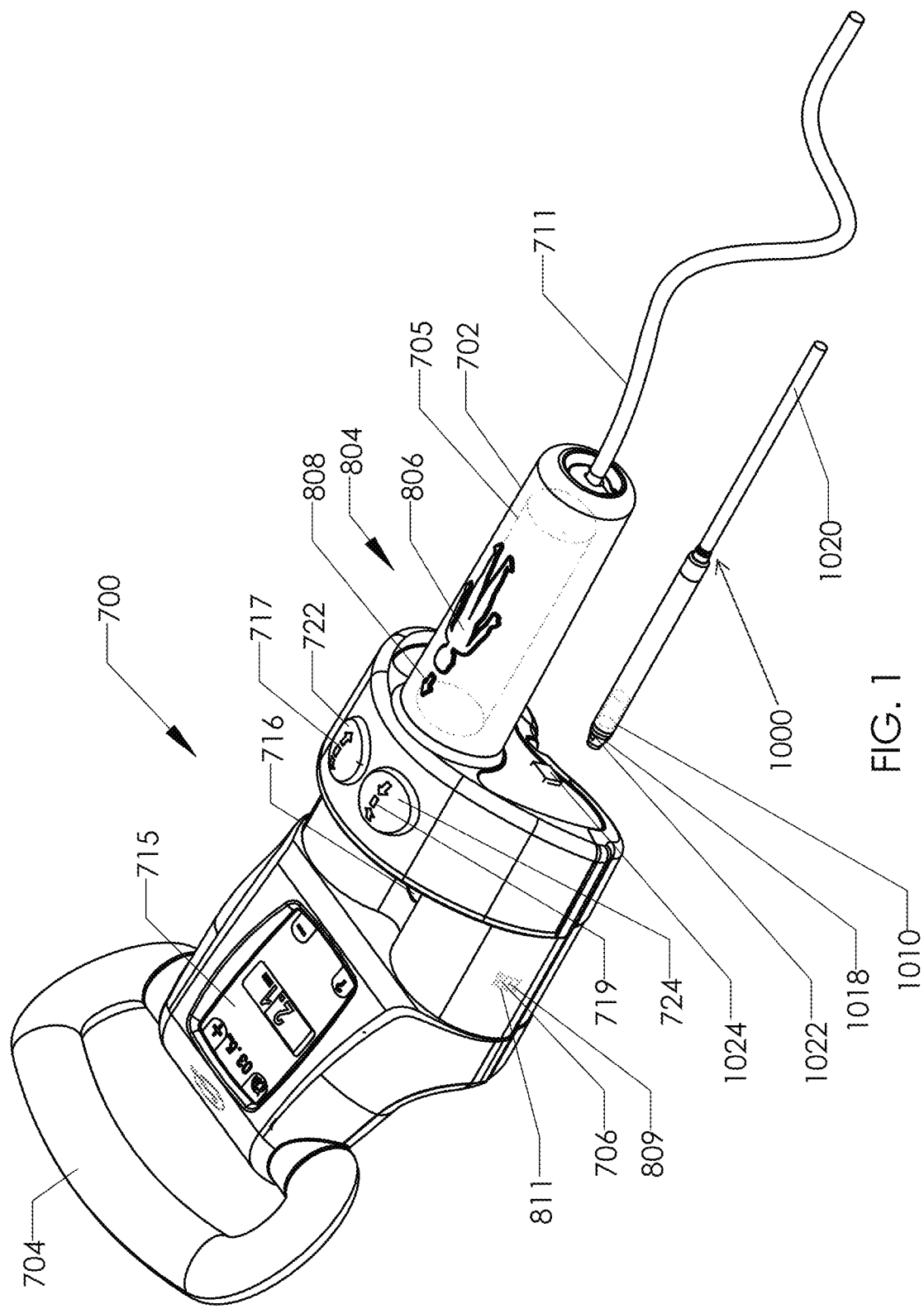
FIG. 1 illustrates one embodiment of an external adjustment device.
Figure 2:
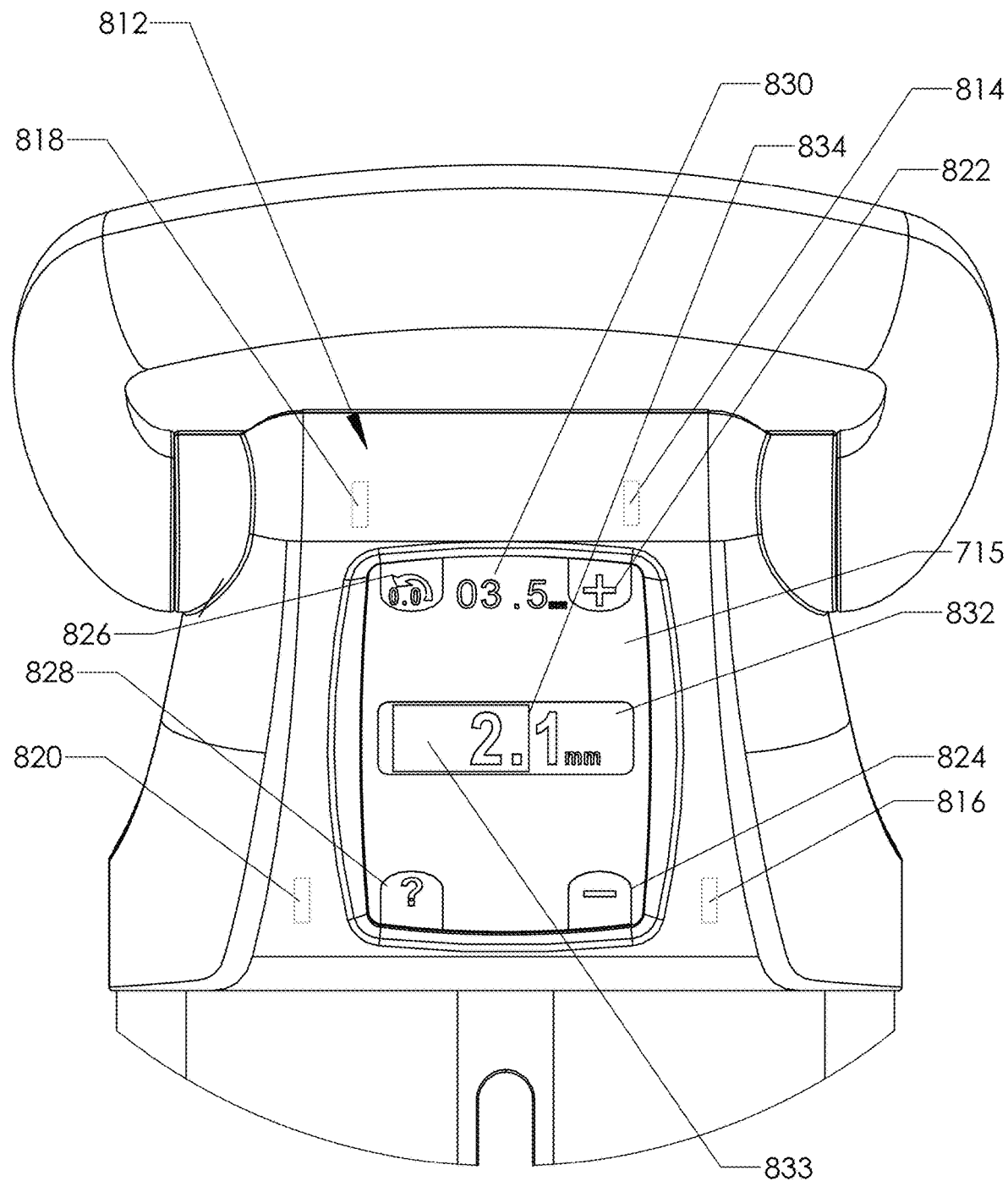
FIG. 2 illustrates a detailed view of the display and control panel of the external adjustment device of FIG. 1.
Figure 3:
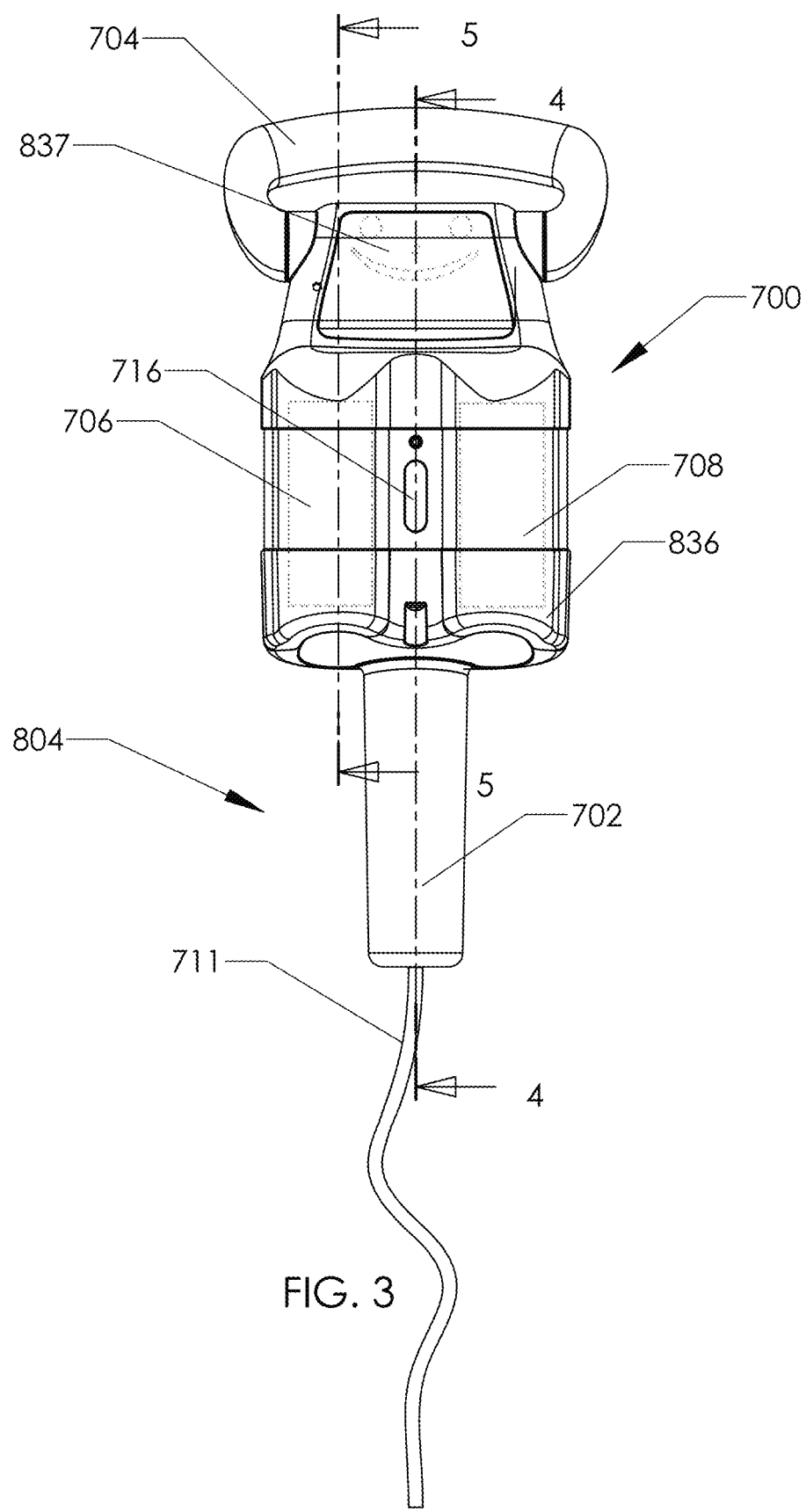
FIG. 3 illustrates the lower or underside surfaces of the external adjustment device of FIG. 1.

FIGS. 1-3 illustrate an external adjustment device 700 that is configured for adjusting an adjustable implant, such as a force-applying device, more specifically represented by (though not limited to) a distraction device 1000. The distraction device 1000 may include any number of distraction, or generally, adjustable force-applying devices such as those described in U.S. Pat. Nos. 7,862,502, 7,955,357, 8,197,490, 8,449,543, and 8,852,187, the disclosures of which are hereby incorporated by reference in their entirety, and/or U.S. patent application Ser. Nos. 12/121,355, 12/411,107, 12/250,442, 12/761,141, 13/198,571 13/655,246, 14/065,342, 13/791,430, 14/355,202, 14/447,391, and 14/511,084, the disclosures of which are hereby incorporated by reference in their entirety. The distraction device 1000 generally includes a rotationally mounted, internal permanent magnet 1010 that rotates in response to a magnetic field applied by the external adjustment device 700. Rotation of the magnet 1010 in one direction causes distraction of the device 1000 while rotation of the magnet 1010 in the opposite direction causes retraction of the device 1000. Retraction of the device 1000 may generate compressive force while distraction of the device 1000 may generate tensile forces. The external adjustment device 700 may be powered by a rechargeable battery or by a power cord 711. The external adjustment device 700 includes a first handle 702 and a second handle 704. The second handle 704 is in a looped shape, and can be used to carry the external adjustment device 700 and/or steady the external adjustment device 700 during use. The first handle 702 extends linearly from a first end of the external adjustment device 700 while the second handle 704 is located at a second end of the external adjustment device 700 and extends substantially off axis or is angled with respect to the first handle 702. In one embodiment, the second handle 704 may be oriented substantially perpendicular relative to the first handle 702, although other arrangements are possible.

The first handle 702 contains a motor 705 that drives a first external magnet 706 and a second external magnet 708, best seen in FIG. 3, via gearing, belts or the like. On the first handle 702 is an optional orientation image 804 comprising a body outline 806 and an optional orientation arrow 808 that shows the correct direction to place the external adjustment device 700 on the patient's body, so that the distraction device is operated in the correct direction. While holding the first handle 702, the operator presses with his thumb the distraction button 722, which has a distraction symbol 717 and is a first color (e.g., green). This distracts the distraction device 1000. If the distraction device 1000 is over-distracted and it is desired to retract, or to lessen the distraction of the device 1000, the operator presses with his thumb the retraction button 724 which has a retraction symbol 719.

Distraction turns the magnets 706, 708 in one direction while retraction turns the magnets 706, 708 in the opposite direction. Magnets 706, 708 have stripes 809 that can be seen in window 811. This allows easy identification of whether the magnets 706, 708 are stationary or turning, and in which direction they are turning, as well as quick trouble shooting by the operator of the device. The operator can determine the point on the patient where the magnet of the distraction device 1000 is implanted, and then place the external adjustment device 700 in a correct location with respect to the distraction device 1000 by marking the corresponding portion of the skin of the patient, and then viewing this spot through an alignment window 716 of the external adjustment device 700.

FIG. 2 illustrates a control panel 812 that includes several buttons 814, 816, 818, 820 and a display 715. The buttons 814, 816, 818, 820 are soft keys, and able to be programmed for an array of different functions. In some embodiments, the buttons 814, 816, 818, 820 have corresponding legends which appear in the display. To set the length of distraction to be performed on the distraction device 1000, the target distraction length 830 is adjusted using an increase button 814 and/or a decrease button 816. The legend with a green plus sign graphic 822 corresponds to the increase button 814 and the legend with a red negative sign graphic 824 corresponds to the decrease button 816. It should be understood that mention herein to a specific color used for a particular feature should be viewed as illustrative. Colors other than those specifically recited herein may be used in connection with the inventive concepts described herein. Each time the increase button 814 is depressed, it causes the target distraction length 830 to increase by 0.1 mm. In the same way each time the decrease button 816 is depressed, it causes the target distraction length 830 to decrease by 0.1 mm Decrements/increments other than 0.1 mm could also be used. When the desired target distraction length 830 is displayed, and the external adjustment device 700 is placed on the patient, the operator holds down the distraction button 722, and the External Distraction Device 700 turns magnets 706, 708 until the target distraction length 830 is achieved (at which point the external adjustment device 700 stops). During the distraction process, the actual distraction length 832 is displayed, starting at 0.0 mm and increasing/decreasing until the target distraction length 830 is achieved. As the actual distraction length 832 increases/decreases, a distraction progress graphic 834 is displayed. For example a light colored box 833 that fills with a dark color from the left to the right. In FIG. 2, the target distraction length 830 is 3.5 mm, 2.1 mm of distraction has occurred, and 60% of the box 833 of the distraction progress graphic 834 is displayed. A reset button 818 corresponding to a reset graphic 826 can be pressed to reset one or both of the numbers back to zero. An additional button 820 can be assigned for other functions (e.g., help, data, etc.). This button can have its own corresponding graphic 828 (shown in FIG. 2 as "?"). Alternatively, a touch screen can be used, for example capacitive or resistive touch keys. In this embodiment, the graphics/legends 822, 824, 826, 828 may also be touch keys, replacing or augmenting the buttons 814, 816, 818, 820. In one particular embodiment, touch keys at 822, 824, 826, 828 perform the functions of buttons 814, 816, 818, 820 respectively, and the buttons 814, 816, 818, 820 are eliminated. In some embodiments, outputs other than a display may be used, including, for example, an audio output, a USB output, a Bluetooth output, or any other data output that can effectively report data resulting from use of the external adjustment device 700 to a user.

Handles 702, 704 can be held in several ways. For example the first handle 702 can be held with palm facing up while trying to find the location on the patient of the implanted magnet of the distraction device 1000. The fingers are wrapped around the handle 702 and the fingertips or mid-points of the four fingers press up slightly on the handle 702, balancing it somewhat. This allows a very sensitive feel that allows the magnetic field between the magnet in the distraction device 1000 and the magnets 706, 708 of the external adjustment device 700 to be more apparent. During the distraction, the first handle 702 may be held with the palm facing down, allowing the operator to push the device 700 down firmly onto the patient, to minimize the distance between the magnets 706, 708 of the external adjustment device 700 and the magnet 1010 of the distraction device 1000, and thus maximizing the torque coupling. This is especially appropriate if the patient is large or overweight. The second handle 704 may be held with the palm up or the palm down during the magnet sensing operation and the distraction operation, depending on the preference of the operator.

FIG. 3 illustrates the underside, or lower surface, of the external adjustment device 700. At the bottom of the external adjustment device 700, the contact surface 836 may be made of material of a soft durometer, such as an elastomeric material, for example PEBAX® (Arkema, Inc., Torrance, Calif., USA) or Polyurethane. This allows for anti-shock to protect the device 700 if it is dropped. Also, if placing the device on patient's bare skin, materials of this nature do not pull heat away from patient as quickly as some other materials; hence, they "don't feel as cold" as hard plastic or metal. The handles 702, 704 may also have similar material covering them, in order to serve as non-slip grips.

FIG. 3 also illustrates child-friendly graphics 837, including the option of a smiley face. Alternatively this could be an animal face, such as a teddy bear, a horsey, or a bunny rabbit. A set of multiple faces can be removable and interchangeable to match the likes of various young patients. In addition, the location of the faces on the underside of the device allows the operator to show the faces to a younger child, but keep it hidden from an older child, who may not be so amused. Alternatively, sock puppets or decorative covers featuring human, animal, or other characters may be produced so that the device may be thinly covered with them, without affecting the operation of the device, but additionally, the puppets or covers may be given to the young patient after a distraction procedure is performed. It is expected that this can help keep a young child more interested in returning to future procedures.

FIGS. 4 and 5 are sectional views of the external adjustment device 700 shown in FIG. 3, which illustrate the internal components of the external adjustment device 700 taken along various centerlines. FIG. 4 is a sectional view of the external adjustment device 700 taken along the line 4-4 of FIG. 3. FIG. 5 is a sectional view of the external adjustment device 700 taken along the line 5-5 of FIG. 3. The external adjustment device 700 comprises a first housing 868, a second housing 838 and a central magnet section 725. First handle 702 and second handle 704 include grip 703 (shown on first handle 702). Grip 703 may be made of an elastomeric material and may have a soft feel when gripped by the hand. The material may also have a tacky feel, in order to aid firm gripping. Power is supplied via power cord 711, which is held to second housing 838 with a strain relief 844. Wires 727 connect various electronic components including motor 840, which rotates magnets 706, 708 via gear box 842, output gear 848, and center gear 870 respectively. Center gear 870 rotates two magnet gears 852, one on each magnet 706, 708 (one such gear 852 is illustrated in FIG. 5). Output gear 848 is attached to motor output via coupling 850, and both motor 840 and output gear 848 are secured to second housing 838 via mount 846. Magnets 706, 708 are held within magnet cups 862. Magnets and gears are attached to bearings 872, 874, 856, 858, which aid in low friction rotation. Motor 840 is controlled by motor printed circuit board (PCB) 854, while the display is controlled by display PCB 866, which is attached to frame 864.

Figure 6:
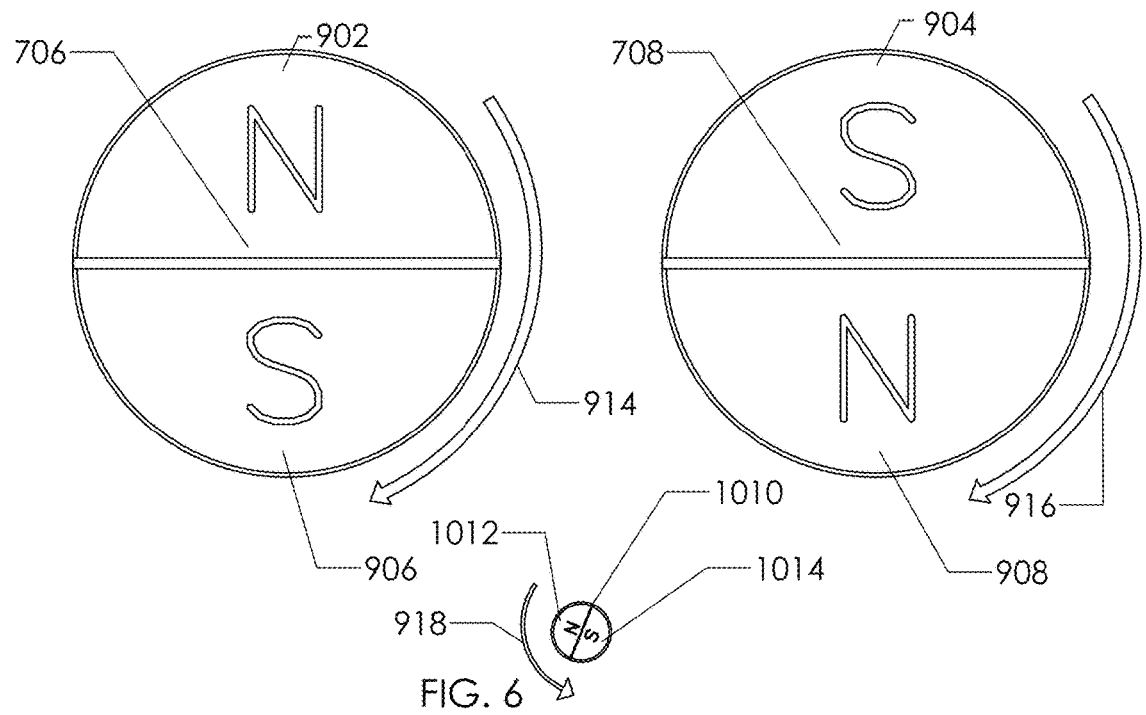
FIG. 6 illustrates an orientation of magnets of one embodiment of an external adjustment device in relation to a magnet of a distraction device.

FIG. 6 illustrates the orientation of poles of the first and second external magnets 706, 708 and the implanted magnet 1010 of the distraction device 1000 during a distraction procedure. For the sake of description, the orientations will be described in relation to the numbers on a clock. First external magnet 706 is turned (by gearing, belts, etc.) synchronously with second external magnet 708 so that north pole 902 of first external magnet 706 is pointing in the twelve o'clock position when the south pole 904 of the second external magnet 708 is pointing in the twelve o'clock position. At this orientation, therefore, the south pole 906 of the first external magnet 706 is pointing is pointing in the six o'clock position while the north pole 908 of the second external magnet 708 is pointing in the six o'clock position. Both first external magnet 706 and second external magnet 708 are turned in a first direction as illustrated by respective arrows 914, 916. The rotating magnetic fields apply a torque on the implanted magnet 1010, causing it to rotate in a second direction as illustrated by arrow 918. Exemplary orientation of the north pole 1012 and south pole 1014 of the implanted magnet 1010 during torque delivery are shown in FIG. 6. When the first and second external magnets 706, 708 are turned in the opposite direction from that shown, the implanted magnet 1010 will be turned in the opposite direction from that shown. The orientation of the first external magnet 706 and the second external magnet 708 in relation to each other serves to optimize the torque delivery to the implanted magnet 1010. During operation of the external adjustment device 700, it is often difficult to confirm that the two external magnets 706, 708 are being synchronously driven as desired.

Figure 7:
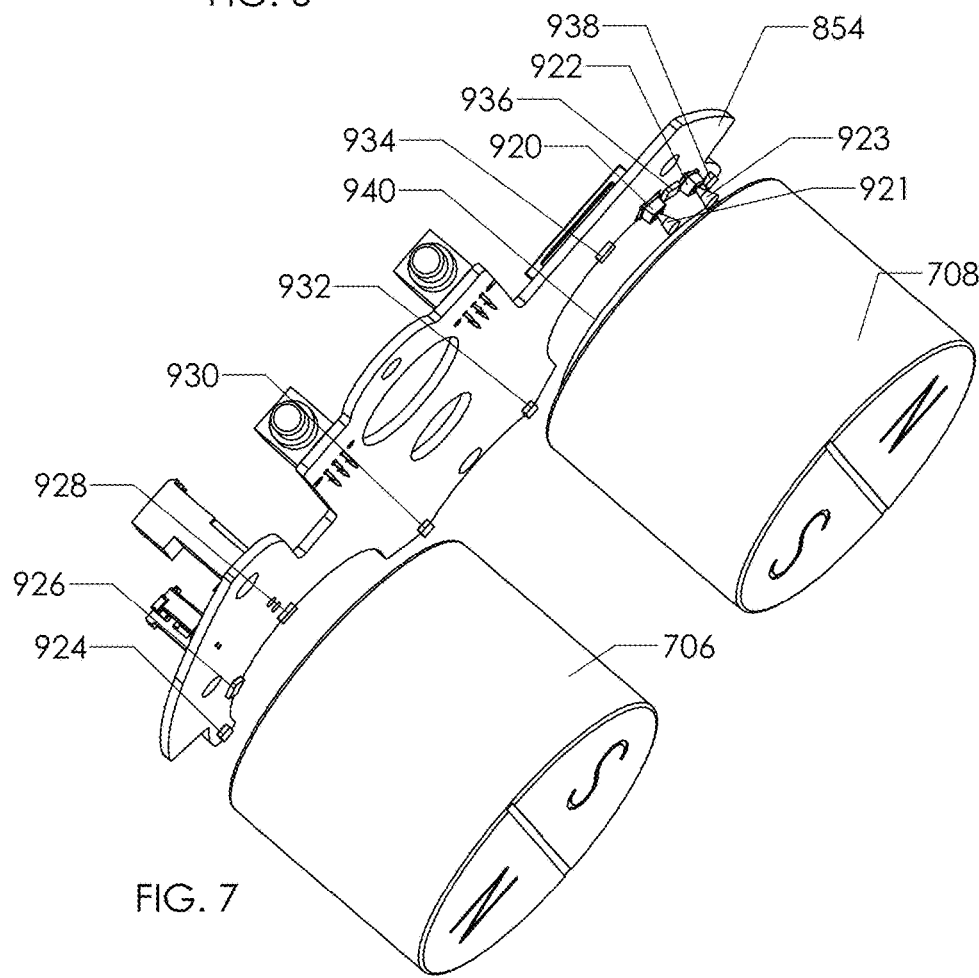
FIG. 7 illustrates various sensors on a circuit board of one embodiment of the external adjustment device.
Figure 8:
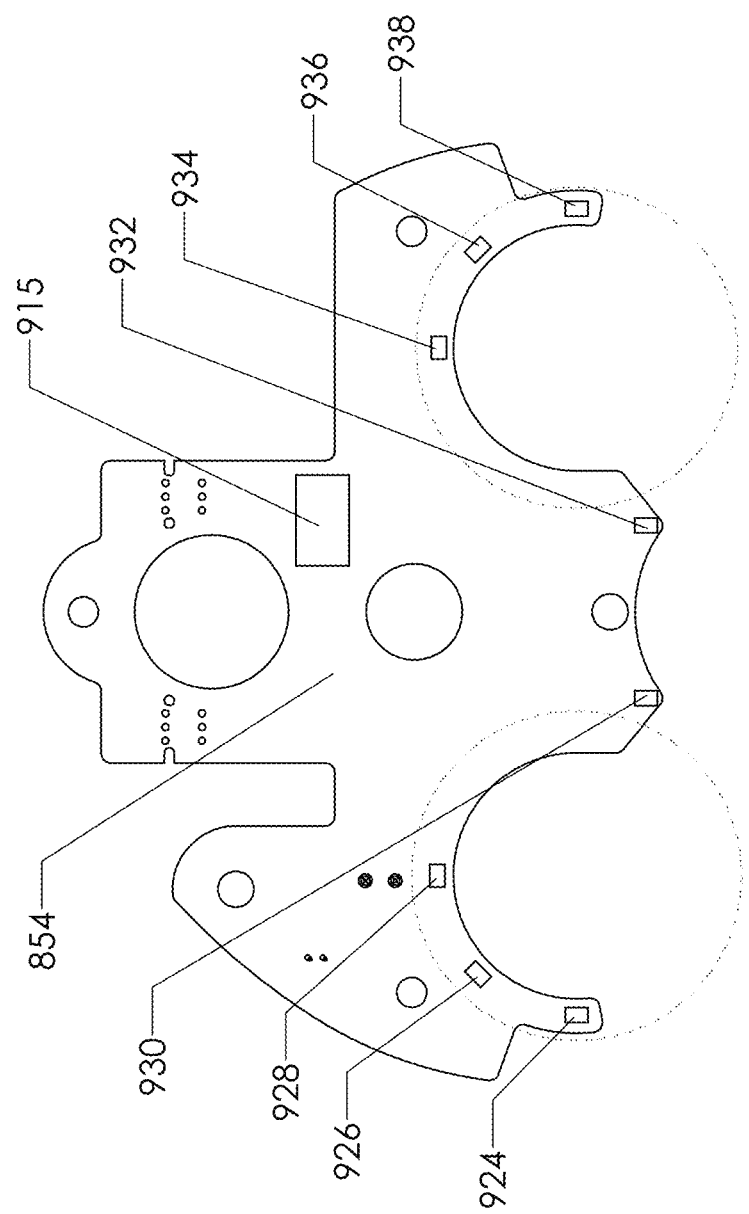
FIG. 8 illustrates various Hall effect sensors on a circuit board of one embodiment of the external adjustment device.

Turning to FIGS. 7 and 8, in order to ensure that the external adjustment device 700 is working properly, the motor printed circuit board 854 comprises one or more encoder systems, for example photointerrupters 920, 922 and/or Hall effect sensors 924, 926, 928, 930, 932, 934, 936, 938. Photointerrupters 920, 922 each comprise an emitter and a detector. A radially striped ring 940 may be attached to one or both of the external magnets 706, 708 allowing the photointerrupters to optically encode angular motion. Light 921, 923 is schematically illustrated between the radially striped ring 940 and photointerrupters 920, 922.

Figure 9A:
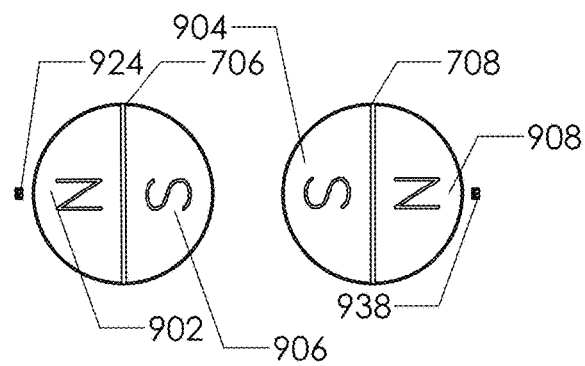
FIG. 9A illustrates a particular configuration of Hall effect sensors relating to the magnets of one embodiment of an external adjustment device.
Figure 9B:
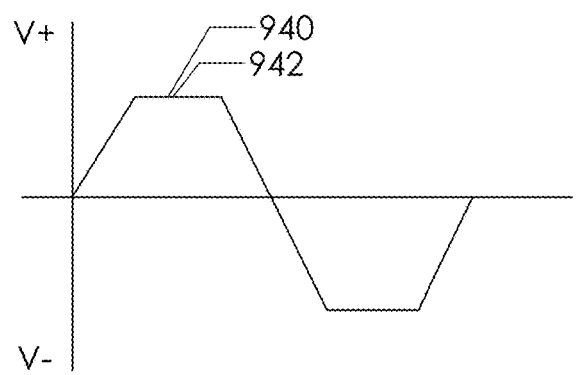
FIG. 9B illustrates output voltage of the Hall effect sensors of FIG. 9A.
Figure 9C:
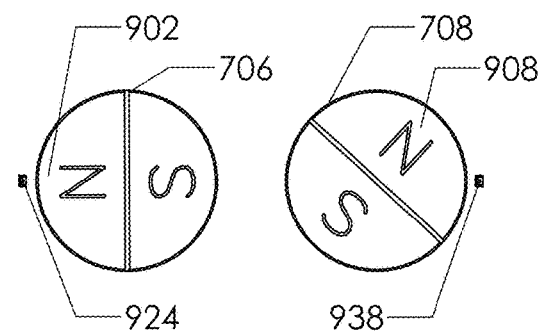
FIG. 9C illustrates the Hall effect sensors of FIG. 9A, with the magnets in a nonsynchronous condition.
Figure 9D:
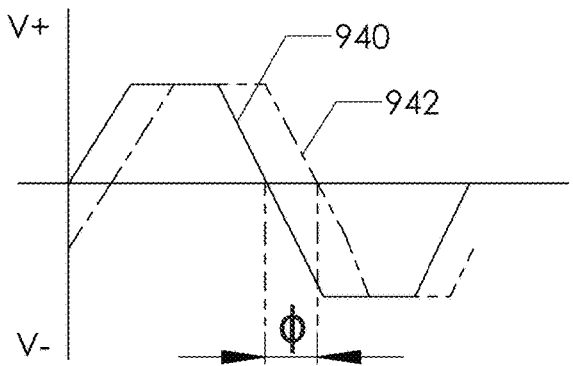
FIG. 9D illustrates the output voltage of the Hall effect sensors of FIG. 9C.

Independently, Hall effect sensors 924, 926, 928, 930, 932, 934, 936, 938 may be used as non-optical encoders to track rotation of one or both of the external magnets 706, 708. While eight (8) such Hall effect sensors are illustrated in FIG. 7, it should be understood that fewer or more such sensors may be employed. The Hall effect sensors are connected to the motor printed circuit board 854 at locations that allow the Hall effect sensors to sense the magnetic field changes as the external magnets 706, 708 rotate. Each Hall effect sensor 924, 926, 928, 930, 932, 934, 936, 938 outputs a voltage that corresponds to increases or decreases in the magnetic field strength. FIG. 9A indicates one basic arrangement of Hall effect sensors relative to sensors 924. 938. A first Hall effect sensor 924 is located at nine o'clock in relation to first external magnet 706. A second Hall effect sensor 938 is located at three o'clock in relation to second external magnet 708, As the magnets 706, 708 rotate in synchronous motion, the first voltage output 940 of first Hall effect sensor 924 and second voltage output 942 of second Hall effect sensor 938 have the same pattern, as seen in FIG. 9B, which graphs voltage for a full rotation cycle of the external magnets 706, 708. The graph indicates a sinusoidal variance of the output voltage, but the clipped peaks are due to saturation of the signal. Even if Hall effect sensors used in the design cause this effect, there is still enough signal to compare the first voltage output 940 and the second voltage output 942 over time. If either of the two Hall effect sensors 924, 938 does not output a sinusoidal signal during the operation or the external adjustment device 700, this demonstrates that the corresponding external magnet has stopped rotating. FIG. 9C illustrates a condition in which both the external magnets 706, 708 are rotating at the same approximate angular speed, but the north poles 902, 908 are not correctly synchronized. Because of this, the first voltage output 940 and second voltage output 942 are out-of-phase, and exhibit a phase shift (φ). These signals are processed by a processor 915 (shown in FIG. 8) and an error warning is displayed on the display 715 of the external adjustment device 700 so that the device may be resynchronized.

Figure 10A:
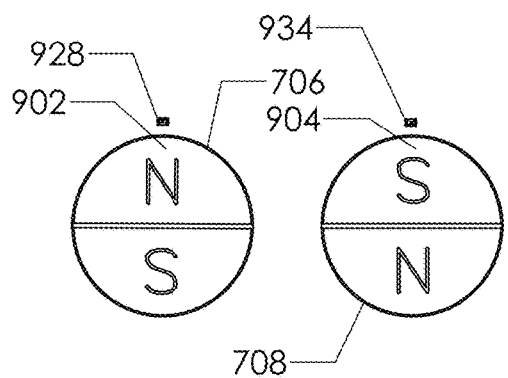
FIG. 10A illustrates a configuration of Hall effect sensors relating to the magnets of one embodiment.
Figure 10B:
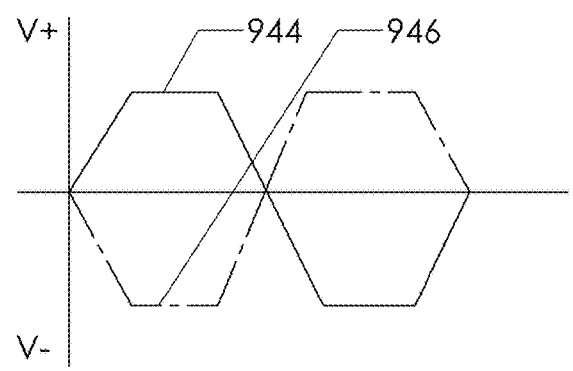
FIG. 10B illustrates the output voltage of the Hall effect sensors of FIG. 10A.

If independent stepper motors are used, the resynchronization process may simply be one of reprogramming, but if the two external magnets 706, 708 are coupled together, by gearing or a belt for example, a mechanical rework may be required. An alternative to the Hall effect sensor configuration of FIG. 9A is illustrated in FIG. 10A. In this embodiment, Hall effect sensor 928 is located at twelve o'clock in relation to external magnet 706 and Hall effect sensor 934 is located at twelve o'clock in relation to external magnet 708. With this configuration, the north pole 902 of external magnet 706 should be pointing towards Hall effect sensor 928 when the south pole 904 of external magnet 708 is pointing towards Hall effect sensor 934. With this arrangement, Hall effect sensor 928 outputs output voltage 944 and Hall effect sensor 934 outputs output voltage 946 (FIG. 10B). Output voltage 944 is, by design, out of phase with output voltage 946. An advantage of the Hall effect sensor configuration of FIG. 9A is that the each sensor has a larger distance between it and the opposite magnet (e.g., Hall effect sensor 924 in comparison to external magnet 708) so that there is less possibility of interference. An advantage to the Hall effect sensor configuration of FIG. 10A is that it may be possible to make a more compact external adjustment device 700 (less width). The out-of-phase pattern of FIG. 10B can also be analyzed to confirm magnet synchronicity.

Returning to FIGS. 7 and 8, additional Hall effect sensors 926, 930, 932, 936 are shown. These additional sensors allow additional precision to the rotation angle feedback of the external magnets 706, 708 of the external adjustment device 700. Again, the particular number and orientation of Hall effect sensors may vary. In place of the Hall effect sensors, magnetoresistive encoders may also be used.

In still another embodiment, additional information may be processed by processor 915 and may be displayed on display 715. For example, distractions using the external adjustment device 700 may be performed in a doctor's office by medical personnel, or by patients or members of patient's family in the home. In either case, it may be desirable to store information from each distraction session to be accessed later. For example, the date and time of each distraction, the amount of distraction attempted, and the amount of distraction obtained. This information may be stored in the processor 915 or in one or more memory modules (not shown) associated with the processor 915. In addition, the physician may be able to input distraction length limits, for example the maximum amount that can be distracted in each session, the maximum amount that can be distracted per day, the maximum amount that can be distracted per week, etc. The physician may input these limits by using a secure entry using the keys or buttons of the device, which the patient will not be able to access.

Returning to FIG. 1, in some patients, it may be desired to place a first end 1018 of the distraction device 1000 towards the head of the patient, and second end 1020 of the distraction device 1000 towards the feet of the patient. This orientation of the distraction device 1000 may be termed antegrade. In other patients, it may be desired to orient the distraction device 1000 with the second end 1020 of the distraction device 1000 towards the head of the patient, and the first end 1018 of the distraction device 1000 towards the feet of the patient. This orientation of the distraction device 1000 may be termed retrograde. In a distraction device 1000 in which the magnet 1010 rotates in order to turn a screw within a nut, the orientation of the distraction device 1000 being either antegrade or retrograde in patient could mean that the external adjustment device 700 would have to be placed in accordance with the orientation image 804 when the distraction device 1000 is placed antegrade, but placed the opposite of the orientation image 804 when the distraction device 1000 is placed retrograde. Software may be programmed so that the processor 915 recognizes whether the distraction device 1000 has been implanted antegrade or retrograde, and then turns the magnets 706, 708 in the appropriate direction when the distraction button 722 is placed.

For example, the motor 705 could be commanded to rotate the magnets 706, 708 in a first direction when distracting an antegrade placed distraction device 1000, and in a second, opposite direction when distracting a retrograde placed distraction device 1000. The physician may, for example, be prompted by the display 715 to input using the control panel 812 whether the distraction device 1000 was placed antegrade or retrograde. The patient may then continue to use the same external adjustment device 700 to assure that the motor 705 turns the magnets 706, 708 in the proper directions for both distraction and refraction. Alternatively, the distraction device may incorporate an RFID chip 1022 (shown in FIG. 1), which can be read and written to by an antenna 1024 on the external adjustment device 700. The position of the distraction device 1000 in the patient (antegrade or retrograde) can be written to the RFID chip 1022, and can thus be read by the antenna 1024 of any external adjustment device 700, allowing the patient to receive correct distractions and/or retractions, regardless of which external adjustment device 700 is used.

Figure 11:
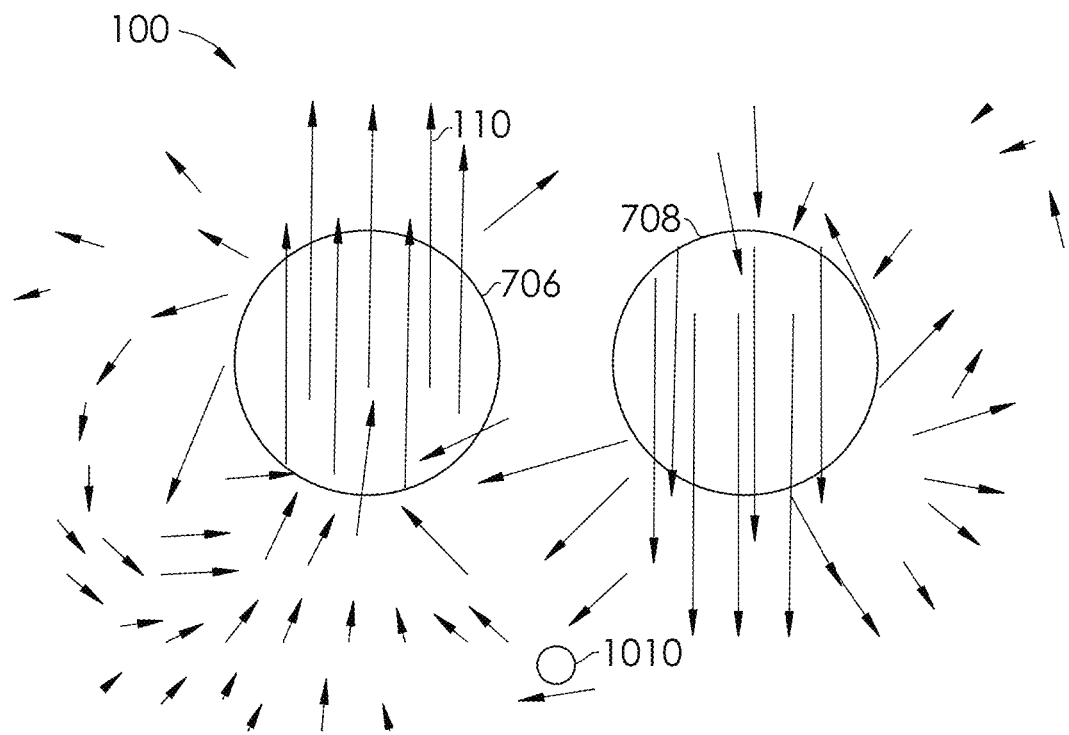
FIG. 11 illustrates a magnetic flux density plot of external magnets of one embodiment of an external adjustment device and the internal permanent magnet.

FIG. 11 is a magnetic flux density plot 100 of the magnetic field characteristics in the region surrounding the two external magnets 706, 708 of the external adjustment device 700, and the internal permanent magnet 1010 of the distraction device 1000. For the purposes of this disclosure, any type of adjustable force-applying (or torque-applying) implant incorporating a rotatable magnet is contemplated as an alternative. In the flux density plot 100, a series of flux lines 110 are drawn as vectors, having orientation and magnitude, the magnitude represented by the length of the arrows. As the external magnets 706, 708 magnetically couple with the internal permanent magnet 1010 and are turned by the motor 840 (FIG. 4) causing the internal permanent magnet 1010 to turn (as described in relation to FIG. 6), the flux lines 110 change considerably in magnitudes and orientation. Embodiments of the present invention use an array of magnetic sensors, such as Hall effect sensors, to receive information about the changing magnetic field characteristics and determine parameters which aid the use and function of the external adjustment device 700, and more importantly, of the distraction device 1000 itself. The first parameter is the general proximity of the external magnets 706, 708 of the external adjustment device 700 to the internal permanent magnet 1010 of the distraction device 1000. It is desired that the external magnets 706, 708 of the external adjustment device 700 be placed close enough to the internal permanent magnet 1010 of the distraction device 1000 so that it will function. A goal of the system may be to maximize the torque that the external magnets 706, 708 impart on the internal permanent magnet, and thus to maximize the distraction force delivered by the distraction device 1000. The second parameter is an estimation of the distance between the external adjustment device 700 and the distraction device 1000, particularly the distance between the external magnets 706, 708 of the external adjustment device 700 and the internal permanent magnet 1010 of the distraction device 1000. This distance estimation, as will be explained in greater detail, can be used in estimating the subsequent parameters. The third parameter is the estimated variable dimension of the distraction device 1000, such as distraction length. On some types of adjustable implants, the variable dimension may be length. On other types of adjustable implants (for example, in a restriction device), the adjustable parameter may be diameter or circumference. The fourth parameter is distraction force. Distraction force may be a useful parameter in scoliosis, in particular because in growing patients increased tensile loads on the skeletal system can accelerate growth. This is known as the Heuter-Volkmann principle. Distraction force is also useful in clinical applications concerned with increasing the length of a bone, or changing the angle or rotational orientation of a bone. Again, depending on the implant, the fourth parameter may incorporate other forces, for example, compression force in an adjustable compression implant, for example in trauma applications, such as those disclosed in U.S. Pat. No. 8,852,187. In other medical applications using an adjustable medical implant, it may be useful to know the moment applied on a body part instead of, or as well as, the force applied. For example, in a scoliosis curve, an "un-bending moment" describes the moment placed by a distraction device on the curve to cause it to straighten. For a particular force value, this moment will vary, depending on how far the distraction device is located laterally from the apex of the scoliosis curve. If the lateral distance is known, for example via an X-ray image, the un-bending moment may be calculated from determining the force applied.

Figure 12A:
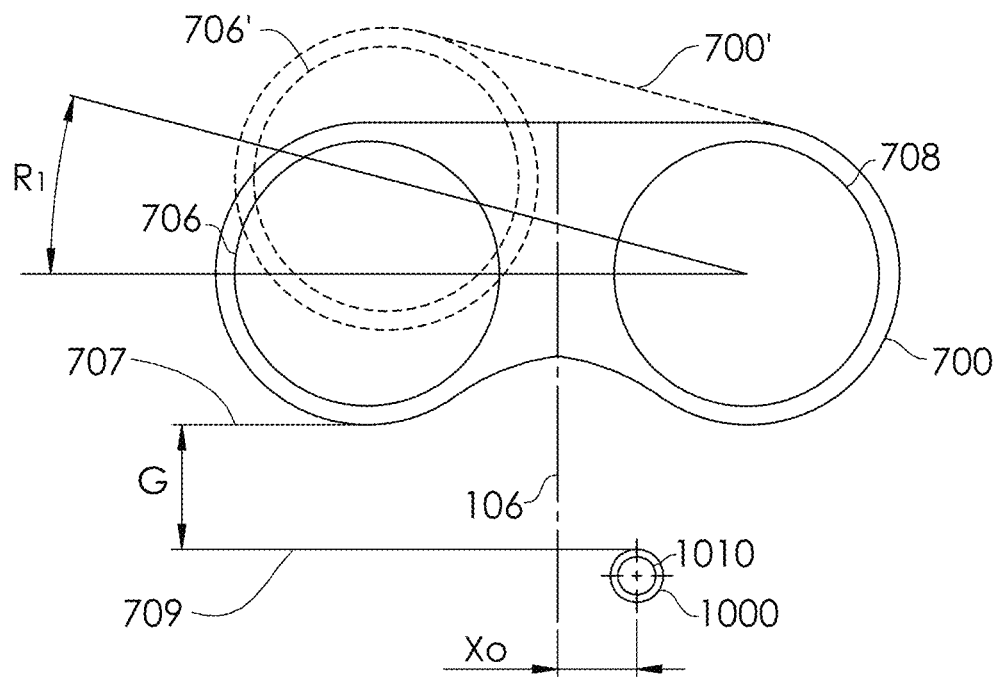
FIG. 12A illustrates a section view of external magnets of one embodiment of an external adjustment device and the internal permanent magnet during positioning of the external adjustment device.

Determining the optimal positioning of the external adjustment device 700 is not always possible. Of course, the implanted distraction device 1000 is not visible to the operator of the external adjustment device 700, and using x-ray imaging to determine its exact location may be difficult, and undesirable due to the additional radiation. Even with an x-ray image that defines a location for the implanted distraction device 1000, the placement of the external adjustment device 700 in a desired location adjacent the skin of the patient may be complicated by extreme curvature of the surface of the patient's body (for example, in scoliosis patients with significant deformity in the torso), or by varying thickness of muscle and fat around the skeletal system (for example circumferentially around the femur in a limb-lengthening patient). FIG. 12A shows, in Cartesian form, the centerline 106 of the external adjustment device 700 aligned with the Y-axis and a gap G between a tangent 707 with the outer surface of the external adjustment device 700 and a tangent 709 with the outer surface of the distraction device 1000. The distance between external magnets 706, 708 and internal permanent magnet 1010 may be slightly larger than the gap G because of their locations within the external adjustment device 700 and the distraction device 1000, respectively (i.e., the housings add slightly to gap G). As the external magnets 706, 708 are placed closer to the internal permanent magnet 1010 of the distraction device 1000, the distraction force that can be generated increases. A lateral offset in alignment is represented by $X_O$ along the x-axis, between the centerline 106 of the external adjustment device 700 and the center of the internal permanent magnet 1010. In an embodiment wherein the external adjustment device 700 has only one external magnet, the lateral offset would be represented by the distance between the center of the external magnet and the center of the internal permanent magnet 1010, along the x-axis. In many cases, a smaller $X_O$, allows a higher maximum possible distraction force. Also shown in dashed lines is an external adjustment device 700' which has been tipped by an angle $R_1$, causing the external magnet 706' to be farther from the internal permanent magnet 1010, than if $R_1$ was close to zero.

Figure 12B:
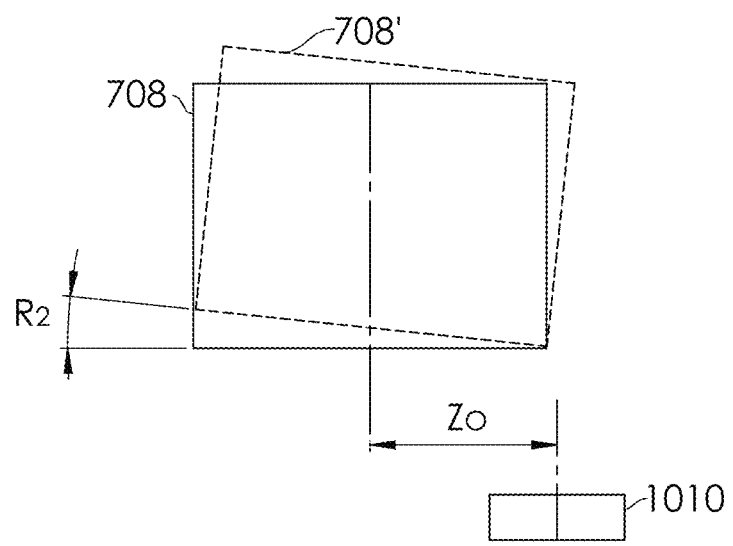
FIG. 12B illustrates a side view of external magnets of one embodiment of an external adjustment device and the internal permanent magnet during positioning of the external adjustment device.
Figure 12C:
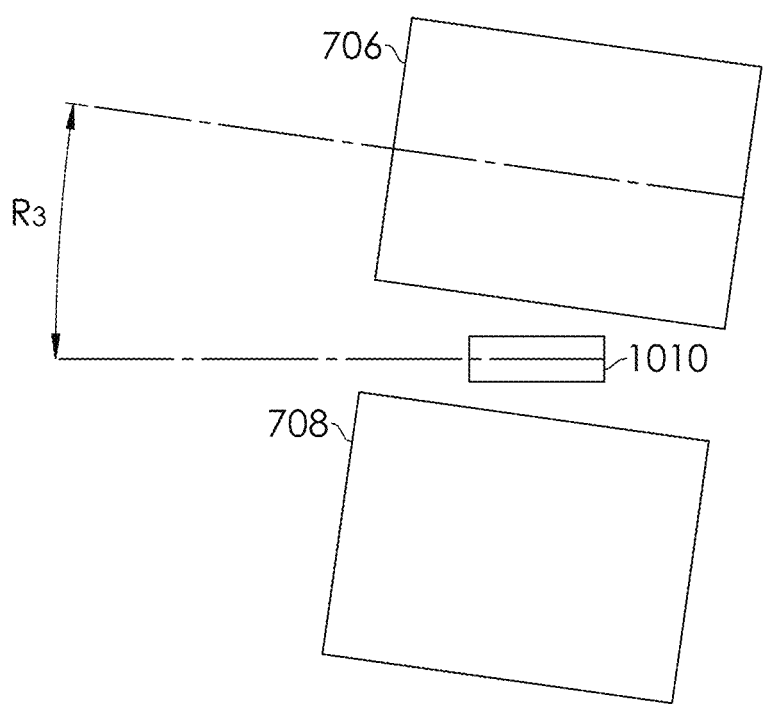
FIG. 12C illustrates a top view of external magnets of one embodiment of an external adjustment device and the internal permanent magnet during positioning of the external adjustment device.

FIG. 12B is similar to FIG. 12A, but FIG. 12B shows a side view of the external adjustment device 700 and internal permanent magnet 1010, with the z-axis left to right and the y-axis up and down. An axial offset $Z_O$ is drawn between the axial center of the external magnet 708 and the axial center of the internal permanent magnet 1010. Also shown is an alternative configuration, with external magnet 708' tipped at an angle $R_2$. The axial offset $Z_O$ would tend to lower the maximum possible distraction force. FIG. 12C is a top view that shows a third tipped angle $R_3$, between the external magnet 706 and the internal permanent magnet 1010. Though in clinical use, $R_2$ and $R_3$ are almost always a non-zero magnitude, the larger they are, the lower the potential coupling torque, and therefore the lower the potential distraction force.

Figure 13A:
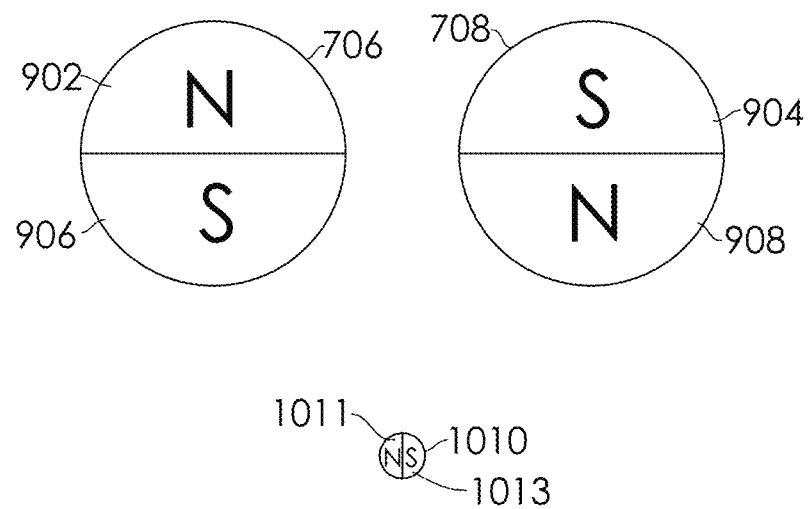
FIG. 13A illustrates a zero torque condition between external magnets of one embodiment of an external adjustment device and the internal permanent magnet.
Figure 13B:
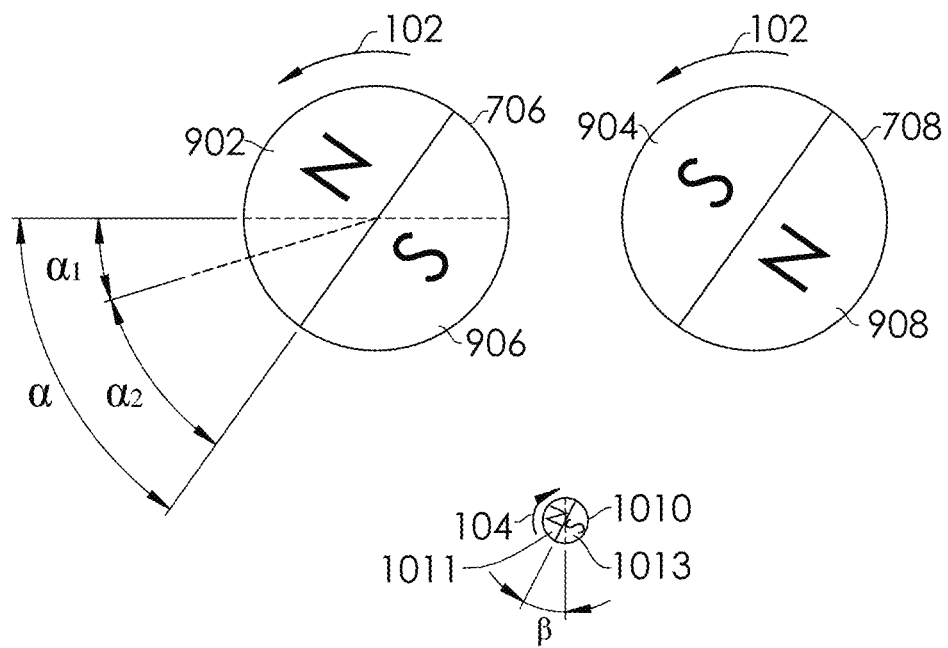
FIG. 13B illustrates magnetic coupling between external magnets of one embodiment an external adjustment device and the internal permanent magnet.

FIGS. 13A through 13D illustrate a variance of magnetic couplings between external magnets 706, 708 and the internal permanent magnet 1010 during an adjustment procedure. FIG. 13A shows a zero torque condition, which may exist, for example, prior to initiating the rotation of the external magnets 706, 708, or at the very start of the operation of the external adjustment device 700. As shown, the north pole 902 of external magnet 706 is pointing in the positive y-direction and the south pole 906 of external magnet 706 is pointing in the negative y-direction, while the south pole 904 of the external magnet 708 is pointing in the positive y-direction and the north pole 908 of the external magnet 708 is pointing in the negative y-direction. The north pole 1011 of the internal permanent magnet 1010 is attracted to the south pole 906 of the external magnet 706 and thus is held in substantially the negative x-direction, and the south pole 1013 of the internal permanent magnet 1010 is attracted to the north pole 908 of the external magnet 708 and thus is held in the positive x direction. All magnets 706, 708, 1010 are in a balanced state and are not fighting each other. As the external adjustment device 700 is operated so that the external magnets 706, 708 begin to turn (as shown in FIG. 13B), it is often the case that there is a nominal resistance torque on the mechanism that is rotatably holding the internal permanent magnet 1010. For example, friction on pins or axles, or friction between the lead screw and the nut of the distraction mechanism. In this particular explanation, it is assumed that external adjustment device either has a single external magnet 706, or has two or more external magnets 706, 708 that rotate synchronously with one another (though other embodiments are possible), and so the reference will currently be made only to the external magnet 706 for simplicity's sake. As external magnet 706 is turned in a first rotational direction 102, up until a first angle $\alpha_1$, it has not yet applied a large enough applied torque $\tau_A$ on the internal permanent magnet 1010 to cause it to initiate rotation in a second opposite rotational direction 104. For example, when the applied torque $\tau_A$ is less than the static threshold resistance torque $\tau_{ST}$ of the internal permanent magnet 1010. However, when angle $\alpha_1$ is exceeded, the applied torque $\tau_A$ becomes greater than the static threshold torque $\tau_{ST}$ of the internal permanent magnet 1010, and thus the rotation of the internal permanent magnet 1010 in the second rotational direction 104 begins, and continues while the external magnet 706 rotates through angle $\alpha_2$. Thus, when the external magnet 706 reaches angle $\alpha$ ($\alpha=\alpha_1+\alpha_2$), the internal permanent magnet 1010 has rotated an angle $\beta$, wherein angle $\beta$ is less than angle $\alpha$. Angle $\beta$ is less than or equal to angle $\alpha_2$. Angle $\beta$ is less than angle $\alpha_2$ in cases where the dynamic resistance torque $\tau_{DR}$ increases as the internal permanent magnet 1010 rotates through angle $\beta$.

Figure 13C:
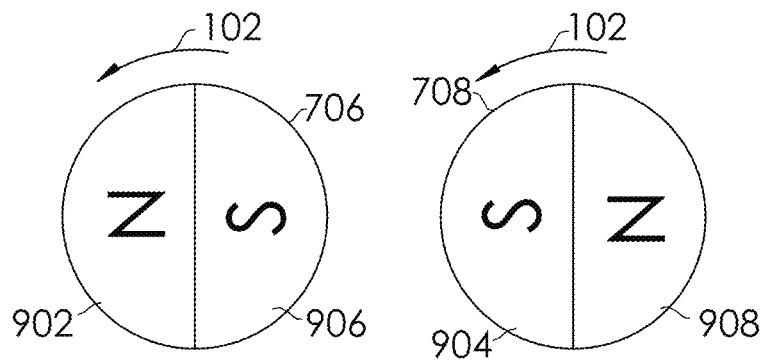
FIG. 13C illustrates continued rotation with increasing coupling torque between external magnets of one embodiment of an external adjustment device and the internal permanent magnet.
Figure 13D:
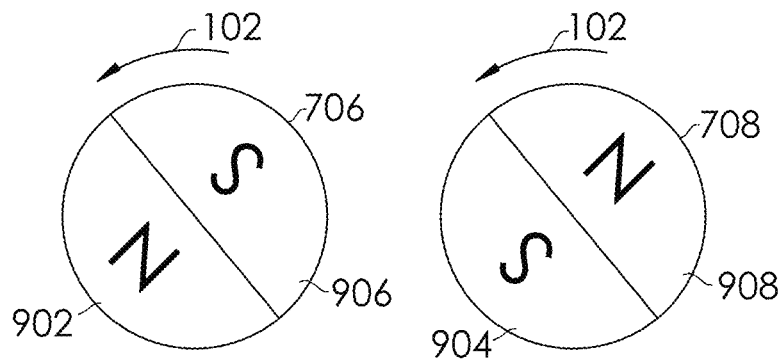
FIG. 13D illustrates slippage between external magnets of one embodiment of an external adjustment device and the internal permanent magnet.

FIG. 13C illustrates the orientation of the magnets 706, 708, 1010 after additional rotation has occurred, and as the dynamic resistance torque $\tau_{DR}$ has increased. This typically occurs as the distraction force of the distraction device 1000 increases, because of increasing friction within the mechanisms of the distraction device 1000, and can occur during the first rotation, or after several rotations. Thus, as seen in FIG. 13C, internal permanent magnet 1010 has rotated a smaller additional amount than the external magnet 706. The term phase lag is used to describe the difference in rotational orientation between the external magnet 706 and the internal permanent magnet 1010. As the dynamic resistance torque $\tau_{DR}$ increases, the phase lag increases. The phase lag between the north pole 902 of the external magnet 706 and north pole 1011 of the internal permanent magnet 1010 in the zero torque condition illustrated in FIG. 13A would be defined as 90°. However, for the purposes of the embodiments of the present invention, phase lag is defined as being 0° at the zero torque condition of FIG. 13A. Regardless of the method chosen to define phase lag, the important factor is the change in the phase lag over time (or over the number of rotations). As the dynamic resistance torque $\tau_{DR}$ increases even further, a point is reached wherein the dynamic resistance torque $\tau_{DR}$ becomes higher than the applied torque $\tau_A$. This creates a slip condition (or stall condition) wherein the engaged poles of the external magnet(s) and the internal permanent magnet slip past each other, or lose their magnetic engagement. Thus the external magnets 706, 708 of the external adjustment device 700 are no longer able to cause the internal permanent magnet 1010 to rotate. Just prior to slippage the phase lag can be as much as 90°. At the point of slippage, as the poles slip over each other, the internal permanent magnet 1010 typically suddenly and quickly rotates backwards in rotational direction 102 (opposite the rotational direction 104 that it had been turning) at some angle less than a full turn. This is shown in FIG. 13D.

Figure 14:
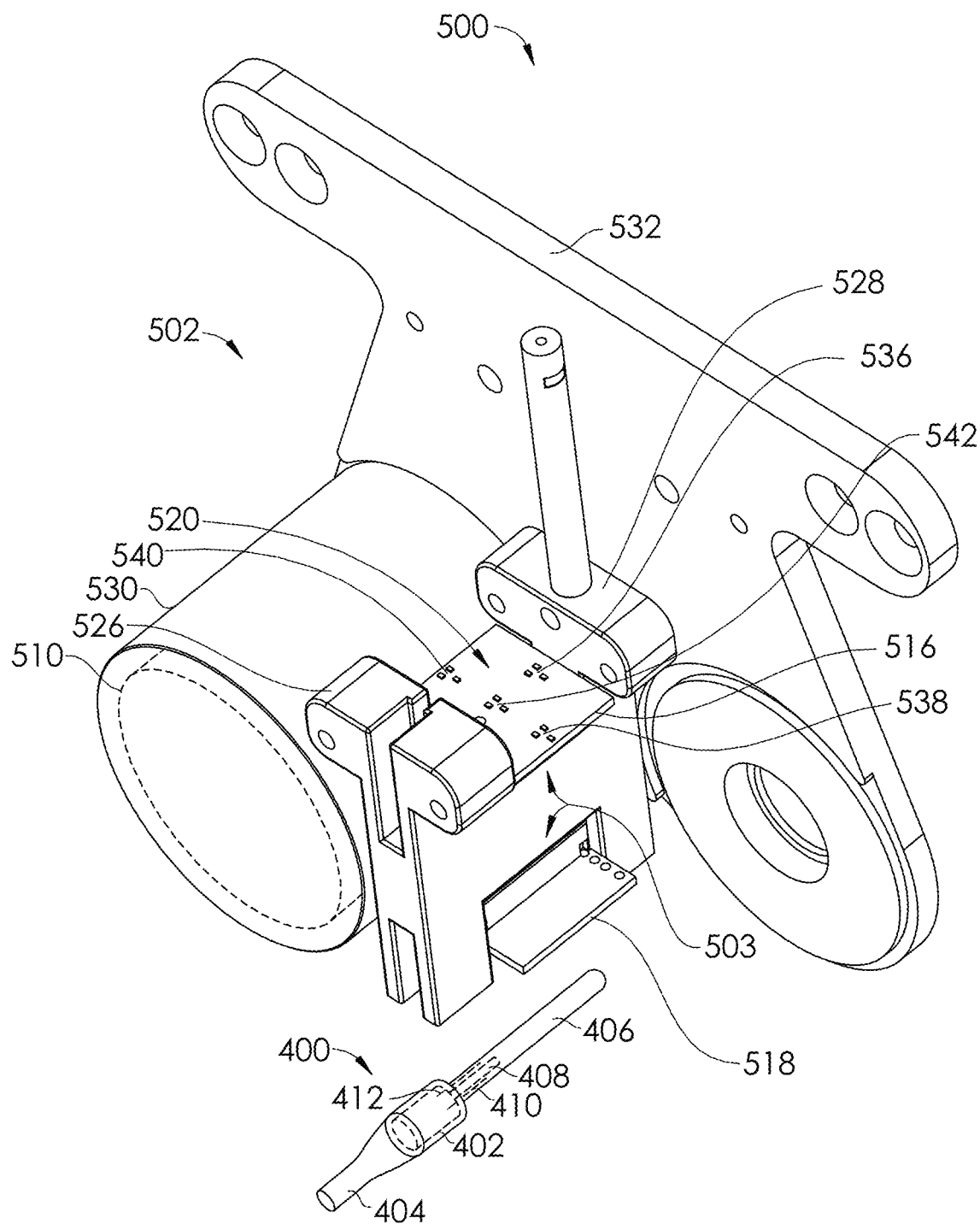
FIG. 14 is an internal view of one embodiment of an external adjustment device having an array of magnetic sensors.

An intelligent adjustment system 500 is illustrated in FIG. 14, and comprises an external adjustment device 502 having a magnetic sensor array 503 which is configured to adjust an adjustable medical device 400 comprising a first portion 404 and a second portion 406, adjustable in relation to the first portion 404. The adjustable medical device 400 is non-invasively adjustable, and contains a rotatable permanent magnet 402, for example a radially-poled cylindrical permanent magnet. The adjustable medical implant 400 is configured to apply an adjustable force within the body. The permanent magnet 402 may be rotationally coupled to a lead screw 408 which is configured to engage with a female thread 410 within the second portion 406, such that the rotation of the permanent magnet 402 causes the rotation of the lead screw 408 within the female thread 410, thus moving the first portion 404 and the second portion 406 longitudinally with respect to each other. The permanent magnet 402 may be non-invasively rotated by applying a torque with one or more external magnets 510 (or 511 of FIG. 16) of the external adjustment device 502. The adjustable medical device 400 is configured for implantation within a patient, and as depicted, is further configured so that the first portion 404 may be coupled to the patient at a first location and the second portion 406 may be coupled to the patient at a second location. In some embodiments, the adjustable medical device 400 may be non-invasively adjusted to increase a distraction force between the first location and the second location. In some embodiments, the adjustable medical device 400 may be non-invasively adjusted to decrease a distraction force between the first location and the second location. In some embodiments, the adjustable medical device 400 may be non-invasively adjusted to increase a compression force between the first location and the second location. In some embodiments, the adjustable medical device 400 may be non-invasively adjusted to decrease a compression force between the first location and the second location. In some embodiments, the adjustable medical device 400 may be non-invasively adjusted to perform two or more of these functions. Alternatively, the adjustable medical device may be a restriction device, configured to be adjusted to increase or decrease a diameter. For example, a diameter that at least partially restricts a body conduit, such as a blood vessel, a gastrointestinal tract or a urinary tract. In an embodiment of this nature, the movement of the first portion 406 in relation to the second portion 406 may increase or decrease traction or tension on a cable or tension member, which in turn causes the restriction (or increase, as the case may be) in diameter of the restriction device.

The magnetic sensor array 503 may comprise two circuit boards 516, 518, for example printed circuit boards (PCBs). The first circuit board 516 may be located in opposition to the second circuit board 518. For example, the first circuit board 516 may be located above and generally parallel to the second circuit board 518. Each circuit board 516, 518 may have a subarray 520 of magnetic sensors 536, 538, 540, 542, for example, Hall effect sensors. A second external magnet 511 (FIG. 16) or even more external magnets may be disposed on the external adjustment device 502. In FIG. 14, a second external magnet 511 has been removed to show detail of the magnetic sensor array 503. Standoff blocks 526, 528 may be disposed on the external adjustment device 502 to hold the first and second circuit boards 516, 518 in place. The standoff blocks 526, 528 may be movable in one or more directions to allow fine adjustment of multiple dimensions of each circuit board 516, 518, as needed, to tune the magnetic sensor array 503. The one or more external magnets 510 are rotatably secured to a base 532, and may be covered with a stationary cylindrical magnet cover 530. It may be desired to rotatably secure the one or more external magnets 510 to the base well enough so that they do not vibrate or rattle, thereby advantageously increasing the signal to noise ratio of the magnetic sensors and the overall effectiveness of the sensor array 503.

Figure 15:
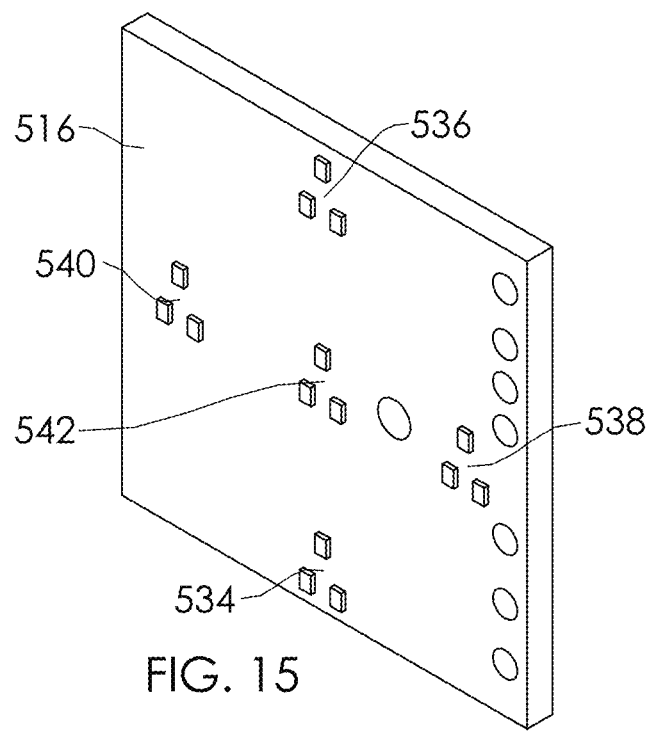
FIG. 15 is a circuit board containing magnetic sensors.

The circuit boards 516, 518 may be substantially identical to each other, or may be mirror images of each other. FIG. 15 shows circuit board 516 in more detail. Five Hall effect sensors (HES) include a forward HES 534, a back HES 536, a left HES 538, a right HES 540, and a middle HES 542. In FIG. 14 circuit board 516 is shown having the effect sensors 534, 536, 538, 540, 542 extending upward, while the circuit board 518 is shown having its Hall effect sensors extending downward (not visible in FIG. 14). In some embodiments, it may be advantageous to have the HES of circuit board 518 extending downward to minimize the distance between the Hall effect sensors and the permanent magnet 402. In some embodiments, circuit board 518 may thus have a mirror image to circuit board 516, so that the left HES 538 of circuit board 516 is directly above the left HES of circuit board 518, etc. However, if the Hall effect sensor used for the left HES is identical to the Hall effect sensor used for the right HES, and the same for forward HES and back HES, the same circuit board may be used for both circuit boards 516, 518, thus reducing manufacturing costs. It is envisioned that printed circuit boards (PCBs) would be used to allow conductive tracks for connections to a voltage source (for example, +5 Volts) for each Hall effect sensor.

In some embodiments, the Hall effect sensors 534, 536, 538, 540, 542 comprise linear Hall effect sensors. The configuration of the circuit boards 516, 518 (i.e., one above the other) aids their use in differential mode, as will be described in regard to FIG. 17. Because the middle HES 542, in both circuit boards 516, 518, is the furthest of the Hall effect sensors from the external magnets 510, 511, it can be less prone to saturation. Therefore, in such embodiments, a more sensitive Hall effect sensor may be used as the middle HES 542. For example, an A1324, produced by Allegro Microsystems LLC, Irvine, Calif., USA, which has a sensitivity of between about 4.75 and about 5.25 millivolts per Gauss (mV/G), or more particularly 5.0 mV/G, may be used. For the other Hall effect sensors (e.g., 534, 536, 538, 540), which are located closer to the external magnets 510, 511 and more likely to be saturated, a less sensitive Hall effect sensor may be used. For example, an A1302, also produced by Allegro Microsystems LLC, Irvine, Calif., USA, with a sensitivity of about 1.3 mV/G may be used.

Figure 16:
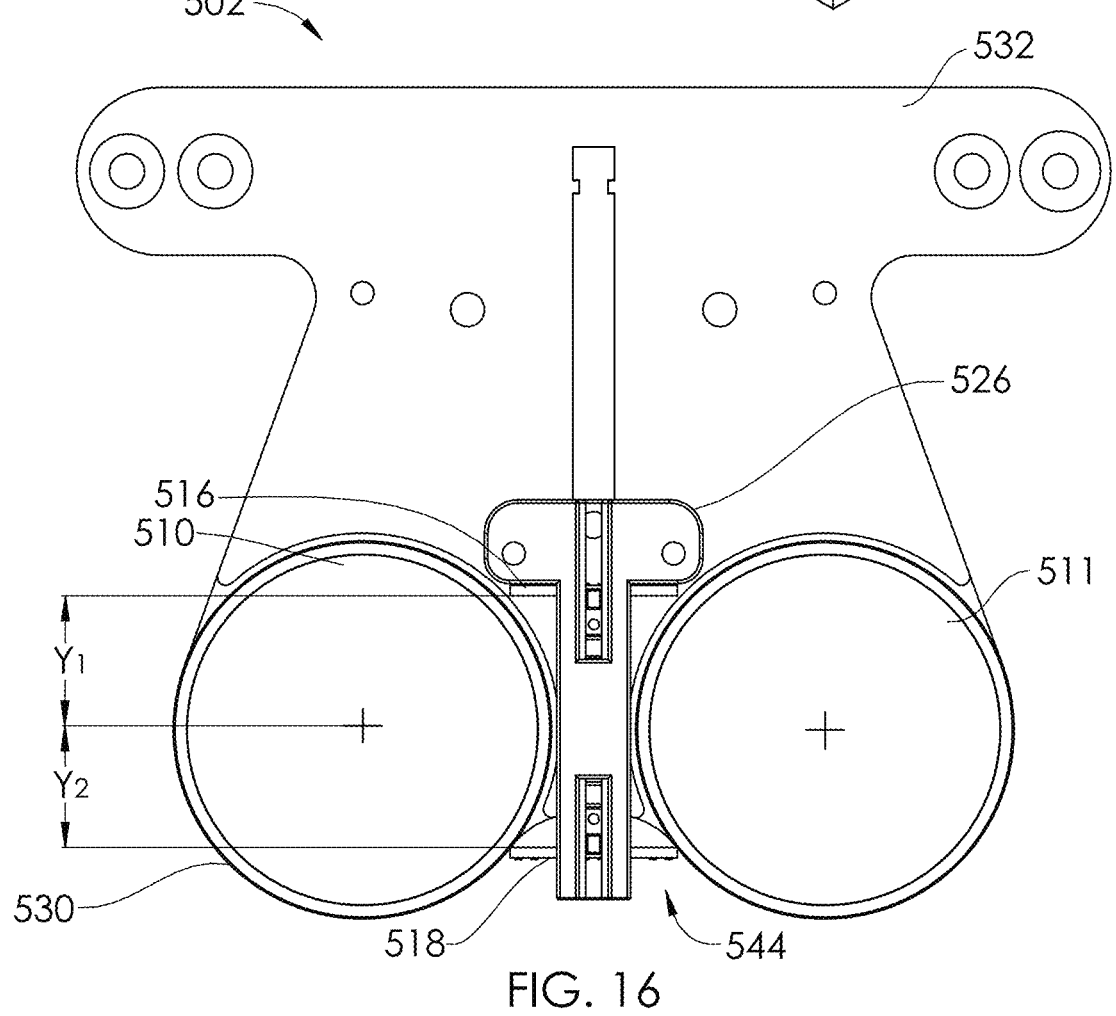
FIG. 16 is a front view of one embodiment of an external adjustment device having an array of magnetic sensors.

Turning to FIG. 16, the orientation of each circuit board 516, 518 is shown in relation to the centers of each external magnet 510, 511. An exemplary arrangement comprises external magnets 510, 511 having diameters between about 2.54 cm (1.0 inches) and 8.89 cm (3.5 inches), and more particularly between about 2.54 cm (1.0 inches) and 6.35cm (2.5 inches). The length of the external magnets 510, 511 may be between about 3.81 cm (1.5 inches) and 12.7 cm (5.0 inches), or between about 3.81 cm (1.5 inches) and 7.62 cm (3.0 inches). In a particular embodiment, the external magnets have a diameter of about 3.81 cm (1.5 inches) and a length of about 5.08 cm (2.0 inches), and are made from a rare earth material, such as Neodymium-Iron-Boron, for example using a grade greater higher N42, greater than N45, greater than N50, or about N52. Returning to FIG. 14, exemplary sizes for the permanent magnet 402 may include a diameter between about 6.35 mm (0.25 inches) and 8.89 mm (0.35 inches), between about 6.85 mm (0.27 inches) and 8.13 mm (0.32 inches), or about 7.11 mm (0.28 inches). The permanent magnet 402 may have a length of between about 1.27 cm (0.50 inches) and 3.81 cm (1.50 inches), between about 1.77 cm (0.70 inches) and 3.18 cm (1.25 inches), or about 1.85 cm (0.73 inches), or about 2.54 cm (1.00 inches). In a particular embodiment, the permanent magnet 402 may be made from a rare earth material, such as Neodymium-Iron-Boron, for example using a grade greater higher N42, greater than N45, greater than N50, or about N52.

Turning again to FIG. 16, circuit board 516 (also called upper circuit board) may be located a distance $Y_1$ from the center of the external magnets 510, 511 of about 15 mm to 32 mm, or about 21 mm. Circuit board 518 (also called lower circuit board) may be located a distance $Y_2$ from the center of the external magnets 510, 511 of about 17 mm to 35 mm, or about 26 mm. The external adjustment device 502 may include a depression 544 between the two external magnets 510, 511 to allow skin and/or fat to move into the depression when the external adjustment device is pressed down on the patient, thereby allowing the external magnets 510, 511 to be placed as close as possible to the permanent magnet 402. In some embodiments of external adjustment devices 502 having two external magnets 510, 511, the central axes of the two external magnets 510, 511 may be separated from each other by between about 50 mm and 100 mm, between about 55 mm and 80 mm, or about 70 mm.

Figure 17:
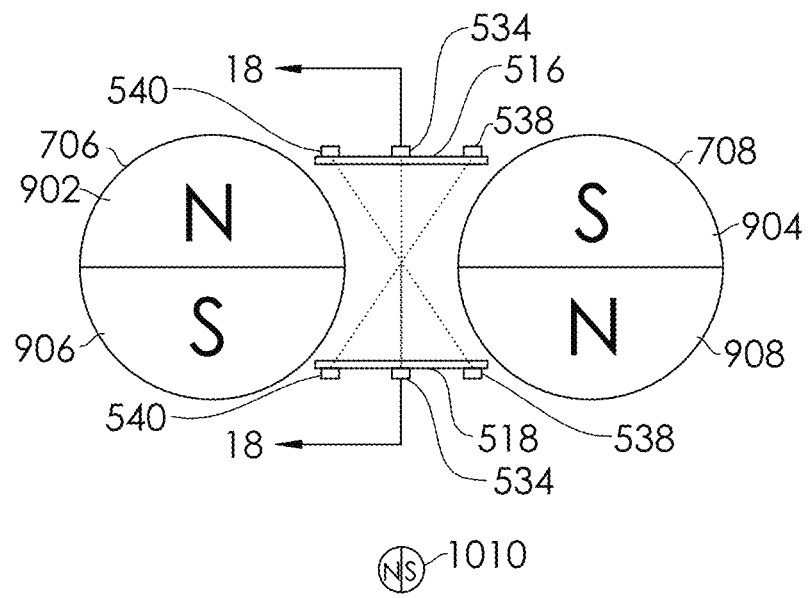
FIG. 17 is a front view of an arrangement of magnetic sensors in relation to external magnets of one embodiment of an external adjustment device and an internal permanent magnet.
Figure 18:
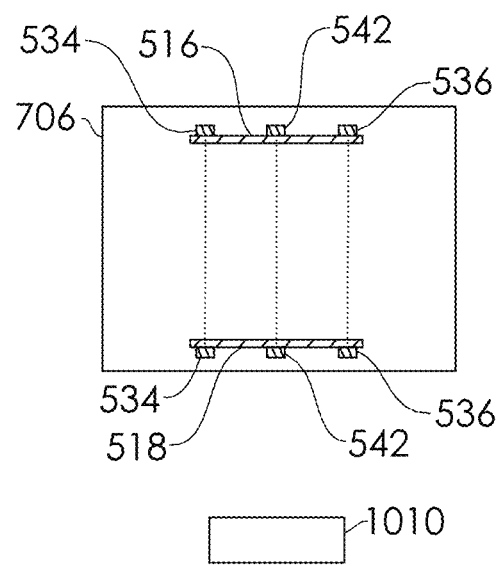
FIG. 18 is a sectional view of the arrangement of magnetic sensors of FIG. 17 taken along line 18.

In FIG. 17 a front view of the external adjustment device 502 (of FIGS. 14 & 16) shows the pairs of Hall effect sensors that are coupled to the same differential amplifier. The left HES 538 of circuit board 516 is paired with the right HES 540 of circuit board 518. The left HES 538 of circuit board 518 is paired with the right HES 540 of circuit board 516. In FIG. 18, the forward HES 534 of circuit board 516 is paired with the forward HES 534 of circuit board 518. The middle HES 542 of circuit board 516 is paired with the middle HES 542 of circuit board 518. And, the back HES 536 of circuit board 516 is paired with the back HES 536 of circuit board 518. Dotted lines have been drawn in in both FIGS. 17 and 18 to better illustrate the pairings.

Figure 19:
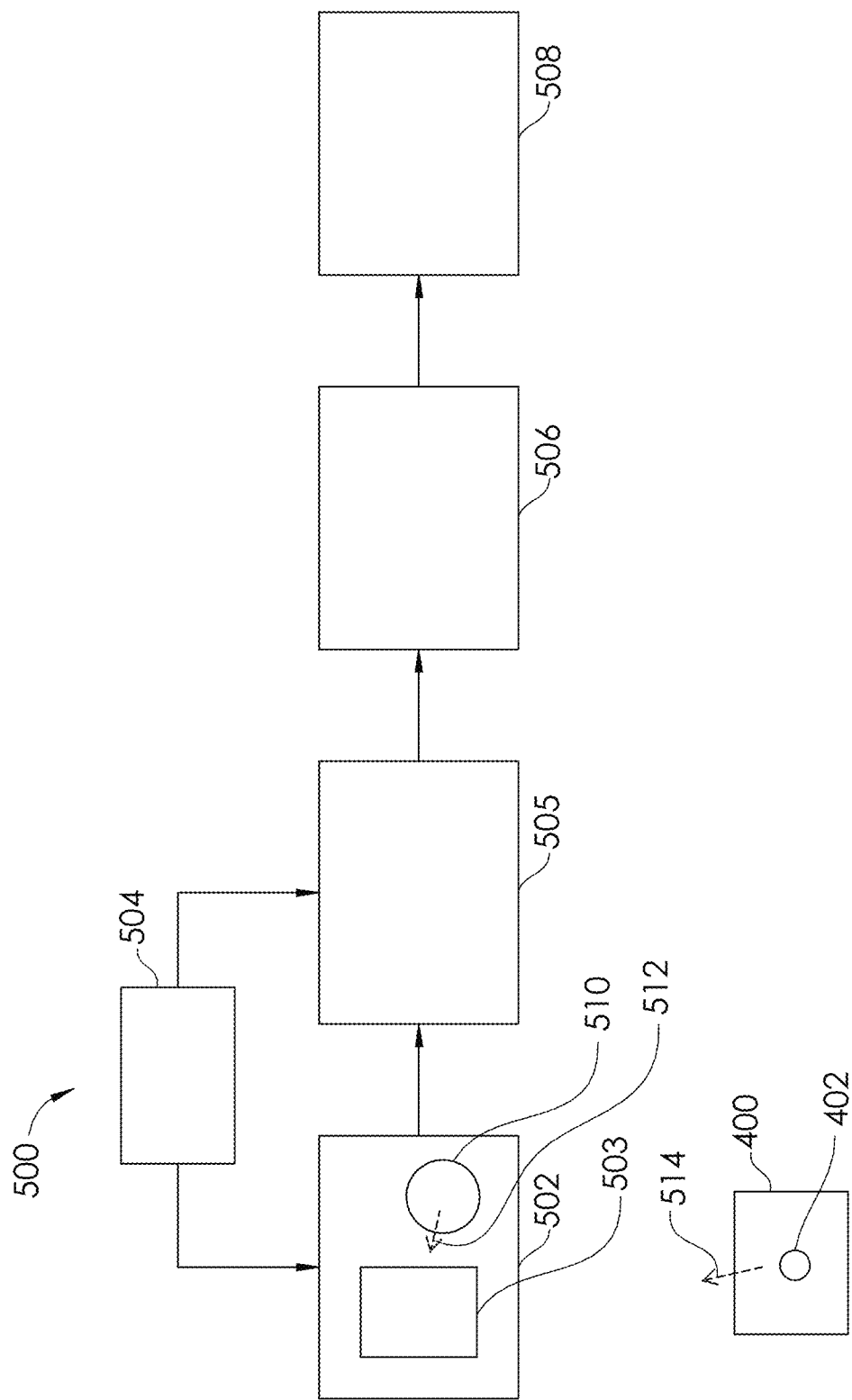
FIG. 19 is a diagram of one embodiment of an external adjustment device of a system for adjusting an adjustable implant
Figure 33:
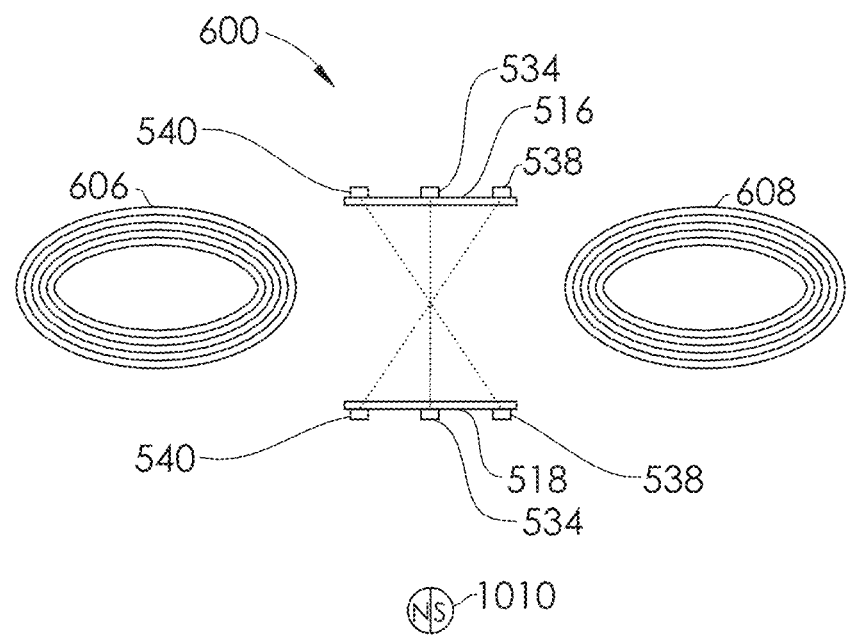
FIG. 33 is a front view of an arrangement of magnetic sensors in relation to one or more external electromagnets of one embodiment of an external adjustment device and an internal permanent magnet.

In FIG. 19, an external adjustment device 502 having a sensor array 503 and having at least one external magnet 510 configured for rotation is powered by a power supply 504. This power supply 504 (or a separate power supply) powers differential amplifiers 505, to which the Hall effect sensors (534, 536, 538, 540, 542 of FIGS. 17 and 18) are coupled. The at least one external magnet 510 of the external adjustment device 502 is rotated (e.g., by a motor 840 of FIG. 4) and magnetically couples to the permanent magnet 402 of the adjustable medical device 400. The coupling between the at least one external magnet 510 and the permanent magnet 402 may have variable coupling and torque characteristics (e.g., increasing dynamic resistance torque $\tau_{DR}$) which cause a varying magnetic field represented by components (i.e., vectors) 512 and 514. It should be mentioned that it is still within the scope of the present invention that embodiments could be constructed so that the one or more rotatable external magnet(s) 510, 511 are one or more electromagnets, creating rotatable magnetic fields comparable to, for example, those created by two rotatable permanent magnets. FIG. 33 illustrates an external adjustment device 600 comprising two electromagnets 606, 608 for creating rotatable magnetic fields. The external adjustment device 600 is otherwise similar to the external adjustment device 502 of FIGS. 14-19. Returning to FIG. 19, a processor 506 (for example a microprocessor) processes signals from the differential amplifiers 505, and the resulting information is displayed on a user interface 508.

Figure 20:
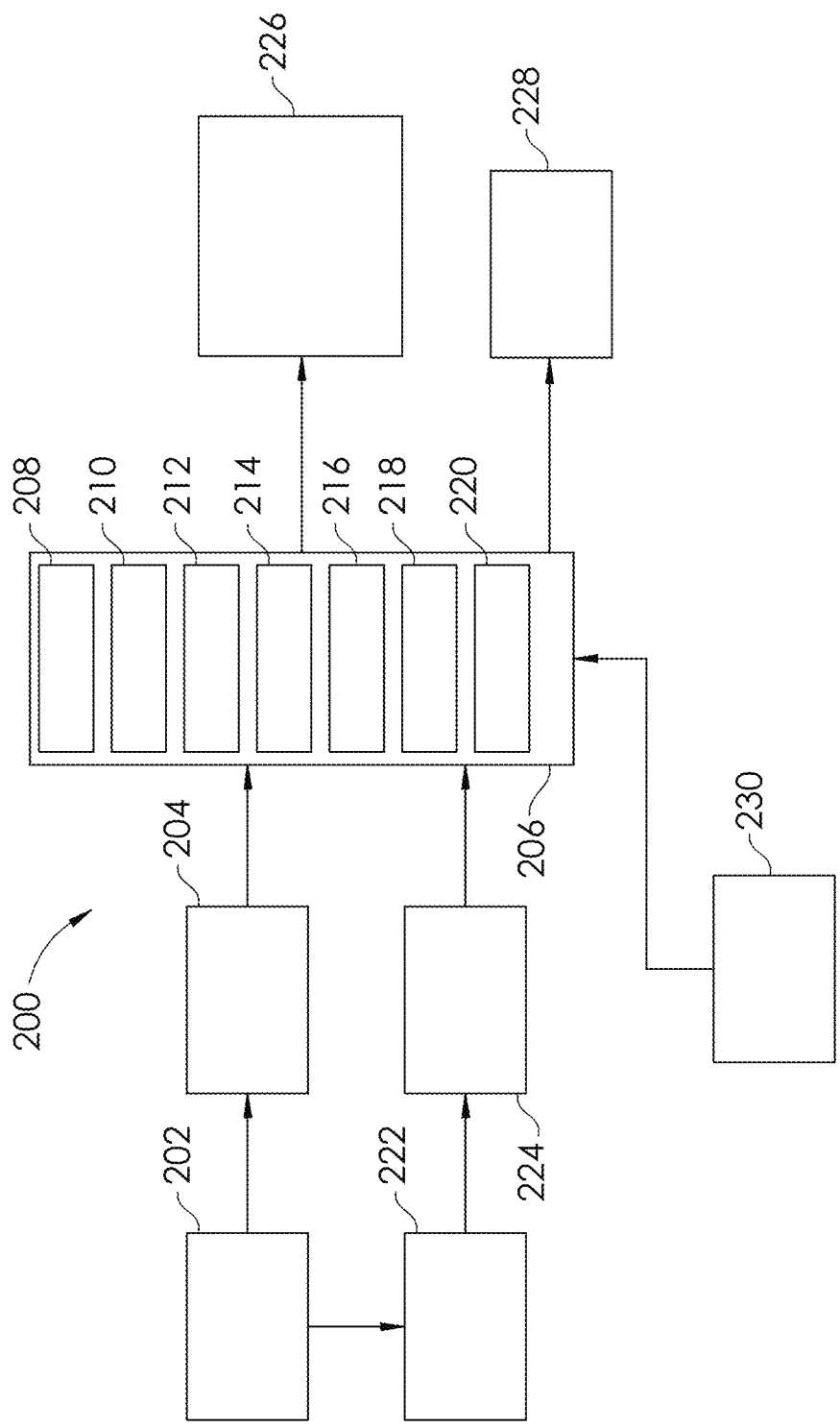
FIG. 20 is a diagram of the logic sequence for one embodiment of an external adjustment device of a system for adjusting an adjustable implant.

FIG. 20 illustrates the system logic 200 within an intelligent adjustment system, (e.g., 500 of FIG. 14) that allows it to take signals received by the sensor array 503 and determine or estimate: 1) the general proximity of the external magnets 706, 708, 510, 511 of the external adjustment device 700,502 to the internal permanent magnet 1010, 402 of the distraction device 1000, 400, 2) a distance between the external adjustment device 700,502 and the distraction device 1000, 400, particularly the distance between the external magnets 706, 708, 510, 511 of the external adjustment device 700, 502 and the internal permanent magnet 1010, 402 of the distraction device 1000, 400, 3) the estimated distraction length of the distraction device 1000, 400, and 4) the distraction force. Data is acquired, in continuous mode in some embodiments, and, for example, at a sampling rate of 1,000 Hz. In step 202 differential inputs from the middle HES 542, left HES 538, and right HES 540 are analyzed, with the maximum and minimum values (voltages) of each complete rotation cycle, thus in step 204, identifying the amplitude of the waveform of the middle HES 542. This amplitude will be used during several subsequent functions programming 206 steps. In step 208, rotational detection is performed. For example, in one embodiment, if the amplitude of the waveform is smaller than 4.2 Volts, then the permanent magnet 1010, 402 of the distraction device 1000, 400 is determined to be rotationally stationary. In step 210, the general proximity of the external adjustment device 700, 502 to the permanent magnet 1010, 402 of the distraction device 1000, 400 is determined. For example a yes or no determination of whether the external adjustment device 700, 502 is close enough to the permanent magnet 1010, 402 to allow operation of the external adjustment device 700, 502. In one embodiment, the data acquisition array is analyzed and if the first and last elements (i.e., all of the values measured in the data acquisition array) are smaller than 0.5 Volts, then the peak of the waveform produced by the Hall effect sensors is complete for being processed. If the amplitude of the waveform is larger than 9.2 Volts, the external adjustment device 700, 502 is acceptably close to the permanent magnet 1010, 402 of the distraction device 1000, 400 to warrant continued adjustment, without aborting.

Figure 22:
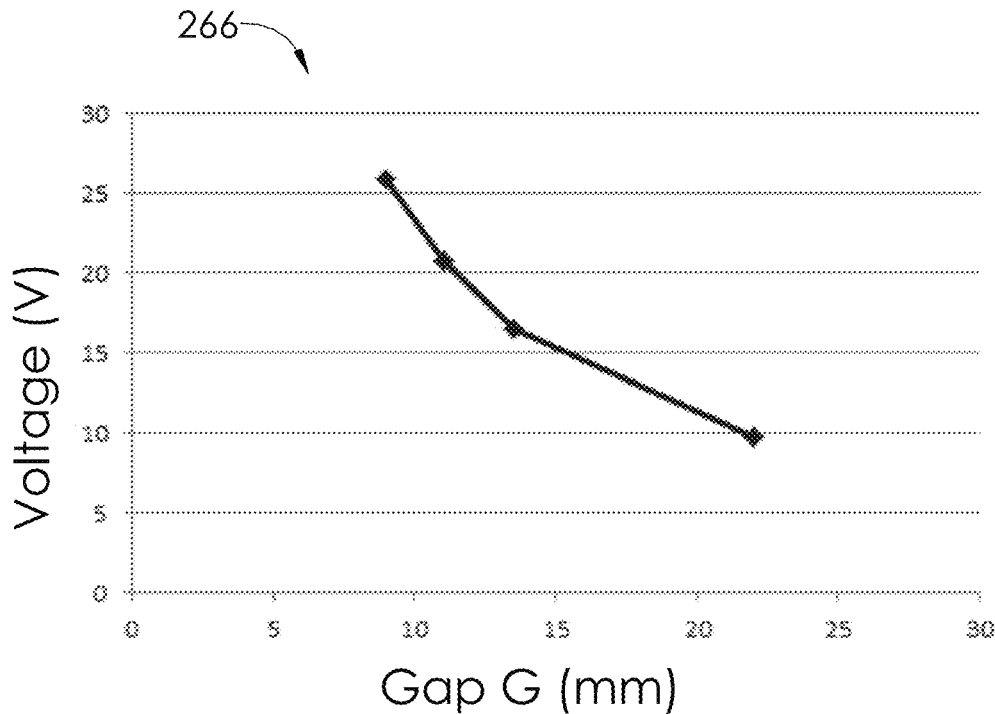
FIG. 22 is a graph of voltage over a series of gap distances.

In step 212, an estimation is done of the actual distance between the external adjustment device 700, 502 and the distraction device 1000, 400 (or between the external magnets 706, 708, 510, 511 and the permanent magnet 1010, 402). Empirical data and curve fit data are used to estimate this distance (gap G). For example, for one particular embodiment. FIG. 22 illustrates a graph 266 of empirical data obtained of voltage (V) for a series of gaps G. A curve fit generated the equation:

$$V = 286.71 \times G^{-1.095}$$

where V is voltage in Volts, and G is gap G in millimeters.

Figure 23:
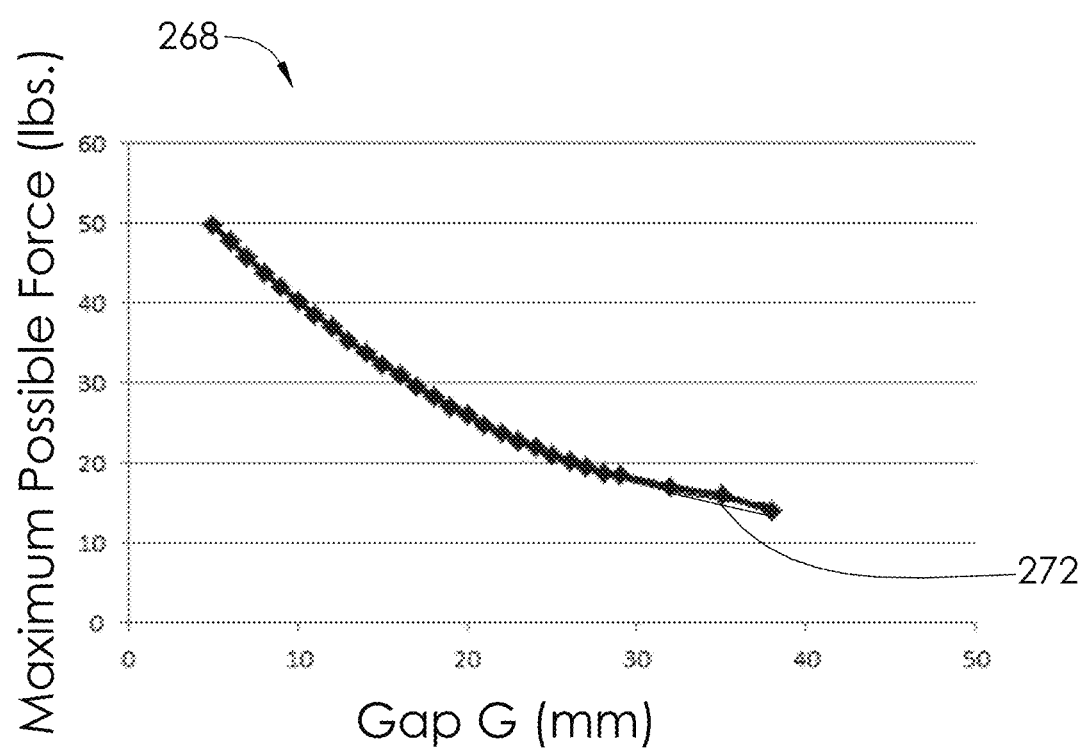
FIG. 23 is a graph of maximum possible distraction force over a series of gap distances.

Returning to FIG. 20, in step 214 the maximum distraction force at the current distance (gap G) is estimated based on empirical data and curve fit data. For example, for one particular embodiment, FIG. 23 illustrates a graph 268 of maximum possible force in pounds (lbs.) for a series of gaps G. A curve fit 272 generated the equation:

$$F = 0.0298 \times G^2 - 2.3262 \times G + 60.591$$

where F is Force in pounds (lbs.), and G is gap G in millimeters

Figure 24:
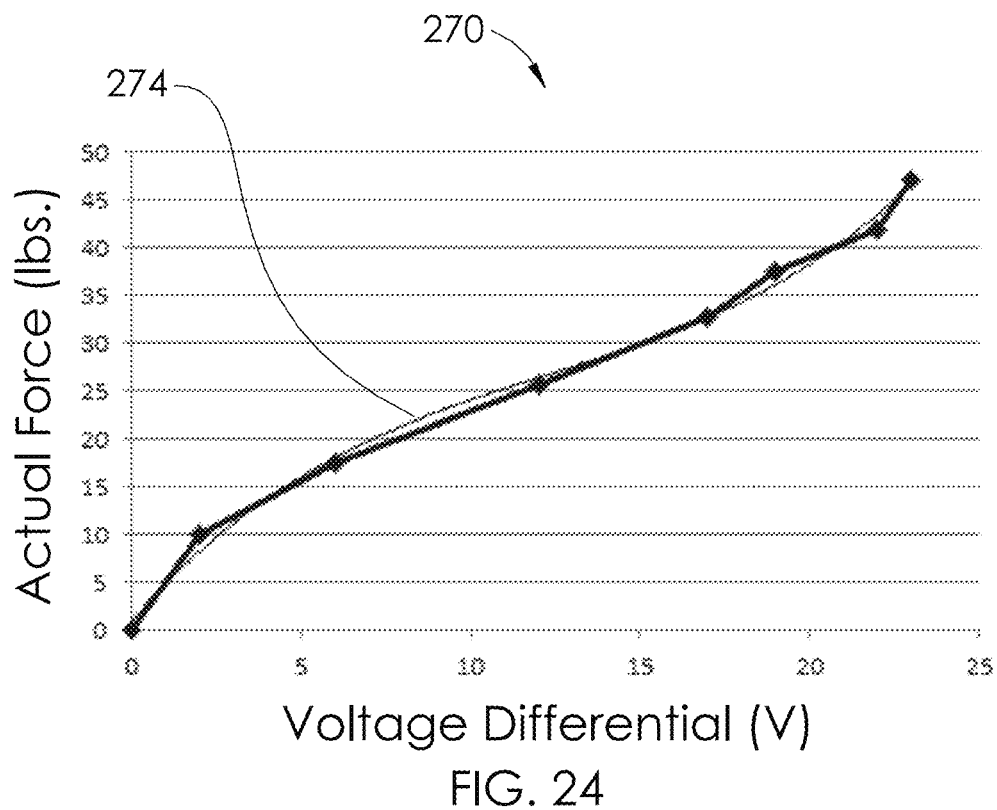
FIG. 24 is a graph of actual force for several voltage differentials.

Returning to FIG. 20, in step 216 a real time estimate of distraction force is performed based on empirical data and curve fit data. For example, for one particular embodiment, FIG. 24 illustrates a graph 270 of estimated or actual distraction force in pounds (lbs.) over a range of voltage differentials. A curve fit 274 generated the equation:

$$F = 0.006 \times V_d^3 - 0.2168 \times V_d^2 + 3.8129 \times V_3 + 1.1936$$

where F if Force in pounds (lbs.), and $V_d$ is differential voltage in Volts.

Figure 25:
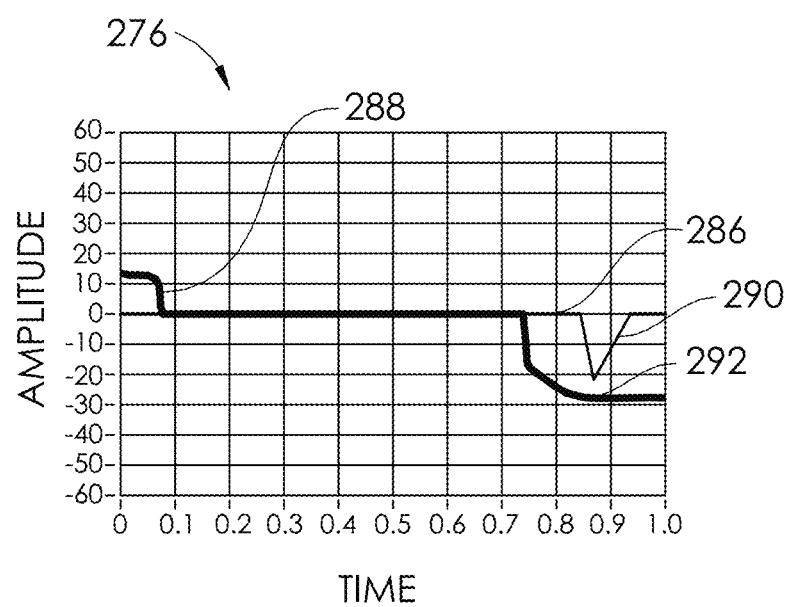
FIG. 25 is a graph of differential voltages of pairs of magnetic sensors.

Returning to FIG. 20, a button may be pushed on a user interface 226, whenever a value for this force is desired, or it may be set to continually update. In step 218, slippage between the external magnets 706, 708, 510, 511 and the permanent magnet 1010, 402 is detected. First, in step 222, the differential input between the left and right HES 538, 540 is acquired, and the maximum and minimum values obtained. Then, in step 224, stall detection logic is run. In one embodiment, if the ratio between the maximum and minimum values of the waveform between two periods is larger than 0.77 Volts during a valid waveform period, and if it happens two times in a row, the slippage is detected (for example, between the left HES 538 of circuit board 516 and the right HES 540 of circuit board 518 and/or between the right HES 40 of circuit board 516 and the left HES 538 of circuit board 518). In one particular embodiment, if the current amplitude is 1.16 times (or more) larger than the previous current amplitude (or 1.16 times or more smaller), slippage is detected. In one embodiment, if the difference between the maximum index and the minimum index is smaller than 12 Volts, slippage is detected. If a stall is detected by the left and right HES 538, 540, slippage is detected. If slippage is detected, an alarm 228 may be sounded or lit. FIG. 25 illustrates a graph 276 of two differential voltages over time in an embodiment of the present invention. Differential voltage 286 (thin line) between the middle HES pair 542 of circuit board 516 and 542 of circuit board 518 may be used to calculate many of the parameters. The triangular perturbation 290 is typically located within the cycle of the differential voltage 286. Changes in the amplitude of the triangular perturbation may represent, for example, slippage or may represent the changes in coupling torque. Differential voltage 288 (thick line) between side pairs (for example, between the left HES 538 of circuit board 516 and the right HES 540 of circuit board 518) is used for confirmation of magnetic slippage. Perturbation 292 is typically located within the cycle of the differential voltage 288. Changes in the amplitude of the perturbation 292 may occur during magnetic slippage.

Returning to FIG. 20, in step 230, when a real time torque value is requested (for example, but pushing a button on the user interface 226), the voltage or amplitude of the waveform is recorded. In step 220 the rotation cycles are counted (this occurs continuously). The distraction length is also counted. For example, in one embodiment, 0.32 mm of linear distraction occurs for every rotation of the internal permanent magnet 1010, 402. In another embodiment, 0.005 mm of linear distraction occurs for every rotation of the internal permanent magnet 1010, 402. The number of rotations may be the number of rotations of the internal permanent magnet 1010, 402 or a fraction or multiple of the number of rotations of the internal permanent magnet 1010, 402 (i.e., "rotations" can be a non-integer number and can be less than 1 or greater than 1). For example, in a distraction device 1000, 400 having a gear module 412 (FIG. 14) between the internal permanent magnet 1010, 402 and the lead screw 408, it may be desired to count the number of rotations of the internal permanent magnet 1010, 402 divided by the gear reduction. For example in a gear reduction of 64:1 wherein the lead screw 408 rotates at a number of rotations per unit time that is 1/64 times that of the internal permanent magnet 1010, 402, the number counted by the system 500 may be the number of rotations of the internal permanent magnet 1010, 402 divided by 64.

In addition to the functions described that are possible with the magnetic sensor array 503, it is possible to use the magnetic sensor array 503 in place of the Hall effect sensors 924, 926, 928, 930, 932, 934, 936, 938 of the embodiments described in relation with FIGS. 7-10B in order to track rotation of the external magnet(s) 706, 708, 510, 511.

Figure 21:
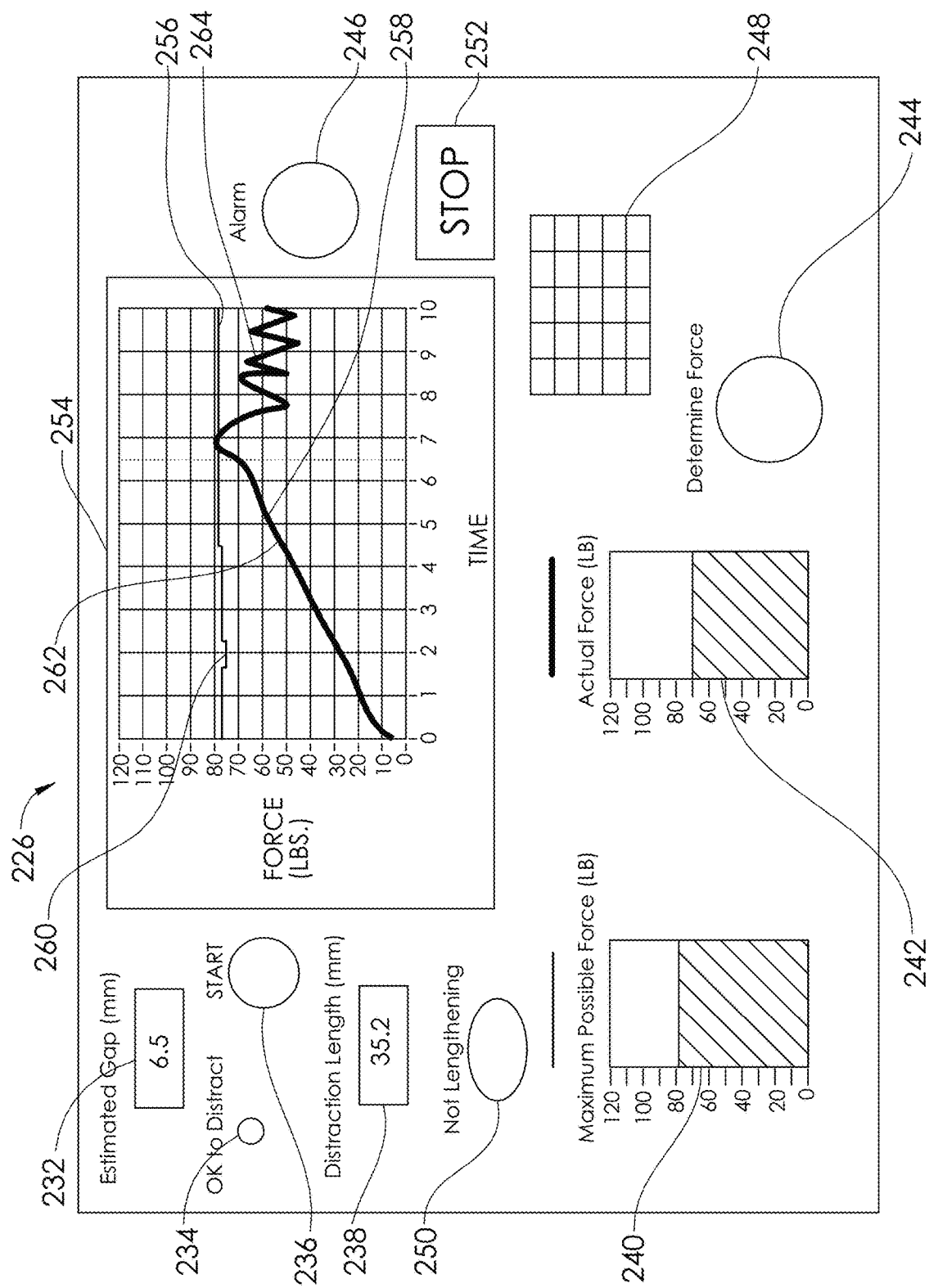
FIG. 21 is a user interface for one embodiment of an external adjustment device of a system for adjusting an adjustable implant.

One embodiment of a user interface 226 for conveying information to the user and receiving inputs from the user is illustrated in FIG. 21. The user interface 226 may comprise a graphic user interface (GUI) and may include a display and control buttons, or one or more touchscreens. The user interface may include an estimated gap display 232, which tells the user the approximate distance (gap G) between the external adjustment device 700, 502 and the distraction device 1000, 400, or between the external magnets 706, 708, 510, 511 of the external adjustment device 700, 502 and the internal permanent magnet 1010, 402 of the distraction device 1000, 400. If this gap G is small enough, an "OK to distract" indicator 234 may light up, vibrate, or sound, depending on whether it is a visual (e.g., LED), tactile, or audio indicator. At this point, the user may initiate distraction/retraction of the distraction device 1000, 400 by pressing a "Start" button 236 of the external adjustment device 700, 502. Alternatively, neither the "OK to distract" indicator 234 nor the "Start" button 236 may appear on the user interface 226 until the gap G is determined to be within an acceptable level, and only then the "Start" button 236 will be displayed on the user interface 226. For example, in one embodiment, an acceptable gap G is a distance below which a coupling may be generated between the external magnets 706, 708, 510, 510 of the external adjustment device 700, 502 and the internal permanent magnet 1010, 402 of the distraction device 1000, 400 sufficient to generate a significant distraction force (e.g., enough to distract bones, joints or tissue). In some embodiments, this may be a gap G of 51 mm or less. In other embodiments, this may be a gap G of 25 mm or less. In other embodiments, this may be a gap of 12 mm or less. In some embodiments, the significant distraction force to distract bones, joints, or tissue may be 1 pound or greater. In other embodiments, it may be 20 pounds or greater. In other embodiments, it may be 50 pounds or greater. In some embodiments, there may be an additional indicator if the gap G is too small. For example, if the gap is 1 mm or less, the system 500 may be set to not function, for example, in order to protect components of body tissue from forces or torques that are too large. This feature may function based on data such as that from FIG. 22. A maximum possible force display 240 may indicate the expected maximum possible force at the current condition (i.e., gap G), either graphically as shown, or with the display of a number, for example, from the data such as that of FIG. 23.

If the "Start" button 236 is pressed and the external adjustment device 700, 502 begins to distract the distraction device 1000, 400, the system 500 will begin counting the revolutions of the internal permanent magnet 1010, 402 and determining the estimated distraction length as described. This may be displayed on the distraction length display 238. An estimated force or actual force display 242 may show the current distraction force (or compression force or other force). This may be updated at any range of update rates. Alternatively, it may be updated only when the user presses a "Determine Force" button 244. If slippage between the magnets 510, 511 and internal permanent magnet 402 or between magnets 706, 708 and internal permanent magnet 1010 is detected, a "Not Lengthening" indicator 250 may light up, vibrate, or sound, depending on whether it is a visual (e.g., LED), tactile, or audio indicator. If at any time any significant event occurs for which user should be notified, an alarm 246 may light up, vibrate, or sound, depending on whether it is a visual (e.g., LED), tactile or audio indicator. Such events may include reaching too high of a force, or reaching the limit of the distraction device 1000, 400, such as its maximum or minimum length. A data input module 248 may be used to input data, for example the starting distraction length of the distraction device 1000, 400, the model of the distraction device, and/or any relevant patient demographic data. At any point during the operation of the system 500, the user may press a "Stop" button 252 to stop all activity. A graph 254 may be included on the user interface 226, for example showing the maximum possible force 256 and the actual force 258 over time. Shifts 260 of the maximum possible force 256 over time may be caused by the gap G changing due to the user applying more or less pressure on the external adjustment device 700, 502. The graph of the actual distraction force 258 may include a ramp up 262, as the distraction device 1000, 400 first moves without significant resistance, and then begins to encounter the resistance caused by tissue or bone. In may also include slippage jumps 264, as the applied torque $\tau_A$ on the internal permanent magnet 1010, 402 increases a little, and then quickly drops as slippage occurs, subsequently being caught and slightly increased by the next pole of the external magnet 706.

The system 500 may have limits that shut down the system if the voltage values demonstrate that the device is being used improperly. Reference above to external magnets 706, 708 may be considered to also reference external magnets 510, 511 where appropriate, and vice versa. For example, if a patient were to turn the external adjustment device 502 backwards, and/or to run the external magnets 510, 511 in an incorrect direction. This is also true for internal permanent magnets 1010 and 402, distraction device 1000 and adjustable device 400, and external adjustment devices 700, 502.

Figure 26:
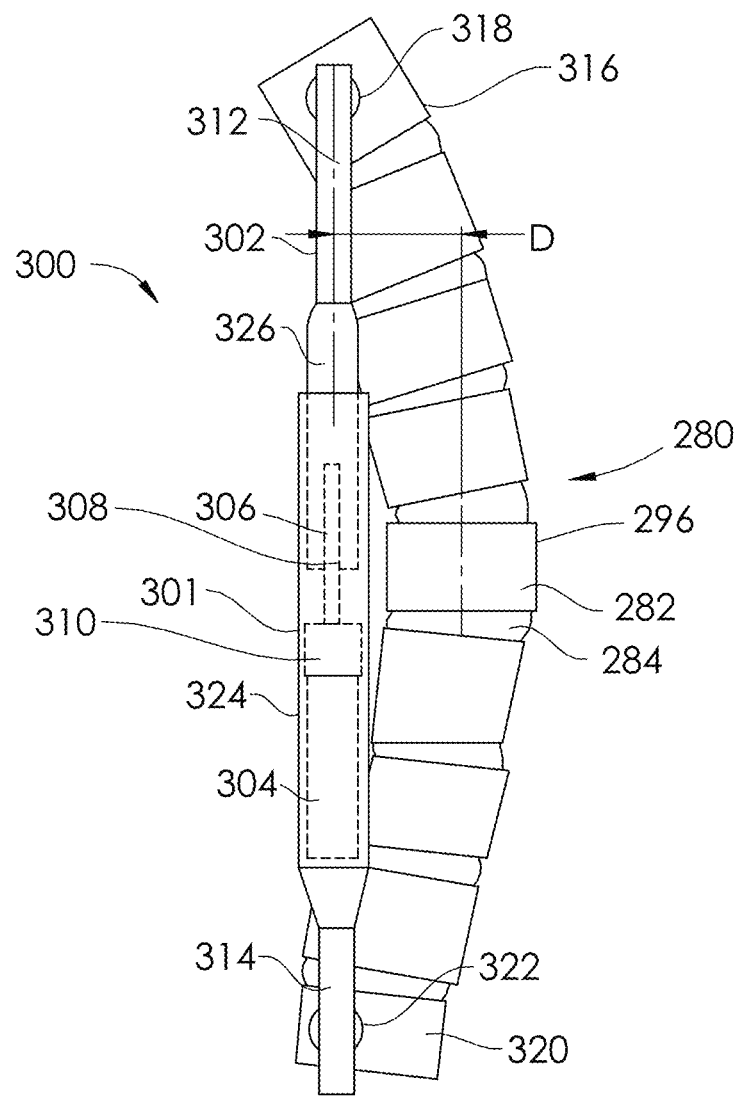
FIG. 26 illustrates an embodiment of an adjustable implant for adjusting length of or force on a spine.

Several embodiments of adjustable implants configured for use with the system 500 are illustrated in FIGS. 26-32. The adjustable spinal implant 300 of FIG. 26, is secured to a spine 280 having vertebrae 282 and intervertebral discs 284. A first end 312 is secured to a portion of the spine 280, for example, to a first vertebra 316 with a pedicle screw 318. A second end 314 is secured to a portion of the spine 280, for example, to a second vertebra 320 with a pedicle screw 322. Alternatively, hooks, wires or other anchoring systems may be used to secure the adjustable spinal implant 300 to the spine 280. Many different portions of the vertebrae may be used to secure the adjustable spine implant 300. For example, the pedicle, the spinous process, the transverse process(es), the lamina, and the vertebral body, for example in an anteriorly placed adjustable spinal implant 300. The adjustable spinal implant 300 may alternatively be secured at either or both ends to ribs, or ilium. The adjustable spinal implant 300 comprises a first portion 301 and a second portion 302. The first portion 301 includes a hollow housing 324 and the second portion 302 includes a rod 326 which is axially extendable in both directions, and which is telescopically contained within the hollow housing 324. A permanent magnet 304 is contained within the hollow housing 324, and is configured for rotation. The permanent magnet 304 is coupled to a lead screw 306 via an intermediate gear module 310. The gear module 310 may be eliminated in some embodiments, with the permanent magnet 304 directly connected to the lead screw 306. In either embodiment, rotation of the permanent magnet 304 (for example, including by application of an externally applied moving magnetic field of an external adjustment device 700, 502) causes rotation of the lead screw 306 (either at the same rotational velocity or at a different rotational velocity, depending on the gearing used). The lead screw 306 is threadingly engaged with a female thread 308, disposed within the rod 326. Certain embodiments of the adjustable spinal implant 300 may be used for distraction of the spine 280 or compression of the spine 280. Certain embodiments of the adjustable spinal implant 300 may be used to correct the spine of a patient with spinal deformity, for example due to scoliosis, hyper (or hypo) kyphosis, or hyper (or hypo) lordosis. Certain embodiments of the adjustable spinal implant 300 may be used to distract a spine, in order to open the spinal canal which may have been causing the patient pain. Certain embodiments of the adjustable spinal implant 300 may be used for adjustable dynamic stabilization of the spine, for control of the range of motion. Certain embodiments of the adjustable spinal implant 300 may be used to correct spondylolisthesis. Certain embodiments of the adjustable spinal implant 300 may be used to stabilize the spine during fusion, allowing for controlled load sharing, or selectable unloading of the spine. The adjustable spinal implant 300 may be configured in certain embodiments as an adjustable artificial disc, or to adjust vertebral body height. In treatment of early onset scoliosis, the adjustable spinal implant 300 is secured to the spine 280 of a patient, over the scoliotic curve 296, and is lengthened intermittently by the system 500. In order to obtain the desired growth rate of the spine, a specific force may be determined which is most effective for that patient. Or, an overall average force (for example 20 pounds) may be determined to be effective as a force target during lengthenings (distraction procedures). The system 500 allows the operator to determine whether the target force is reached, and can also protect against too large of a force being placed on the spine 280. In FIG. 26, a distance D is shown between the center of the spinal adjustment device 300 and the spine 280 at the apex vertebra 282. This may be, for example, measured from an X-ray image. The target force may be derived from a target "unbending" moment, defined as:

$$M_U = D \times F_T$$

where $M_U$ is the target unbending moment, D is the distance D, and $F_T$ is the target force.

Figure 27:
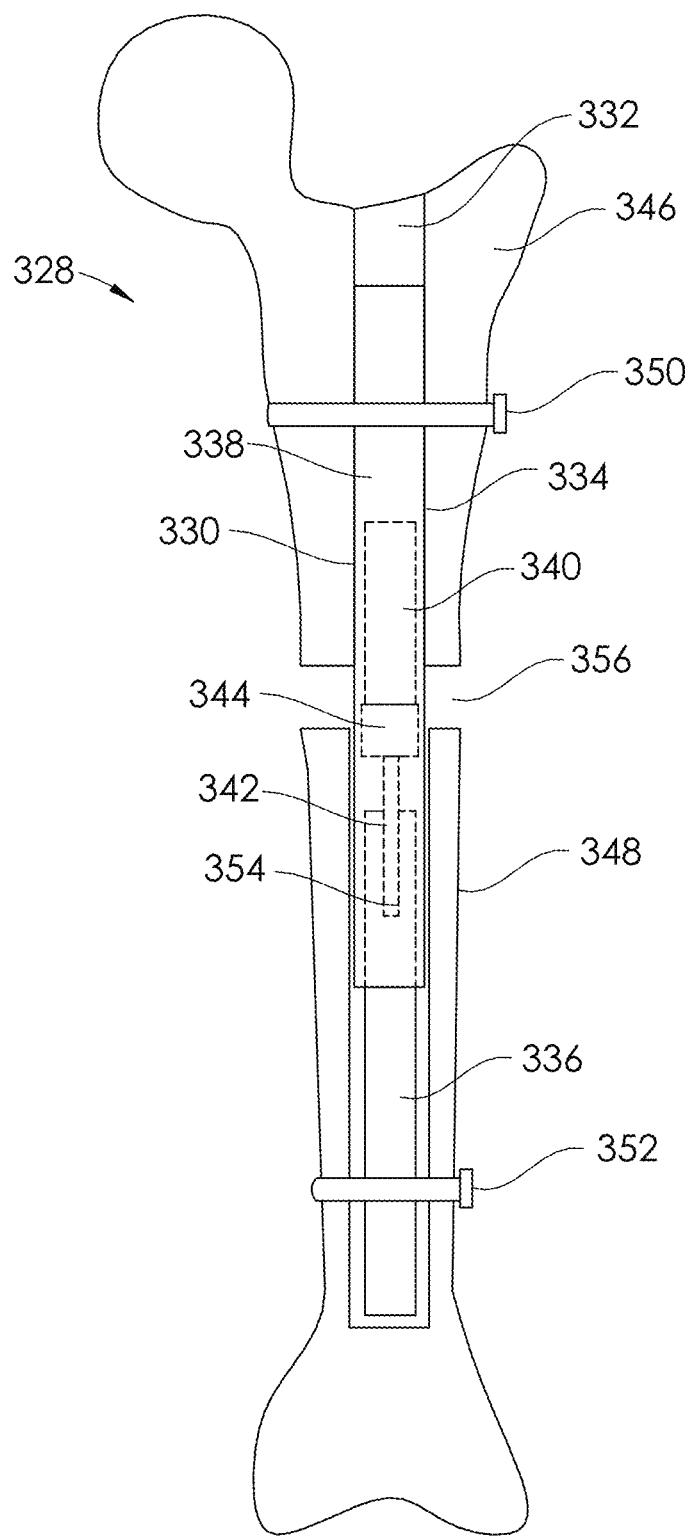
FIG. 27 is an embodiment of an adjustable implant for adjusting the distance or force between sections of bone.

FIG. 27 illustrates a bone 328 with an adjustable intramedullary implant 330 placed within the medullary canal 332. In this particular case, the bone 328 is a femur, though a variety of other bones are contemplated, including, but not limited to the tibia and humerus. The adjustable intramedullary implant 330 includes a first portion 334 having a cavity 338 and a second portion 336, telescopically disposed within the first portion 334. Within the cavity 338 of the first portion 334 is a rotatable permanent magnet 340, which is rotationally coupled to a lead screw 342, first example, via a gear module 344. The first portion 334 is secured to a first section 346 of the bone 328, for example, using a bone screw 350. The second portion 336 is secured to a second section 348 of the bone 328, for example, using a bone screw 352. Rotation of the permanent magnet 340 (for example, by application of an externally applied moving magnetic field of an external adjustment device 700, 502) causes rotation of the lead screw 342 within a female thread 354 that is disposed in the second portion 336, and moves the first portion 334 and the second portion 336 either together or apart. In limb lengthening applications, it may be desired to increase the length of the bone 328, by creating an osteotomy 356, and then gradually distracting the two bone sections 346, 348 away from each other. A rate of approximately one millimeter per day has been shown to be effective in growing the length of the bone, with minimal non-unions or early consolidations. Stretching of the surrounding soft tissue may cause the patient significant pain. By use of the system 500, the patient or physician may determine a relationship between the patient's pain threshold and the force measured by the system 500. In future lengthenings, the force may be measured, and the pain threshold force avoided. In certain applications (e.g., trauma, problematic limb lengthening), it may be desired to place a controlled compression force between the two bone sections 346, 348, in order to form a callus, to induce controlled bone growth, or simply to induce healing, if no limb lengthening is required. System 500 may be used to place a controlled compression on the space between the two bone sections 346, 348.

Figure 28:
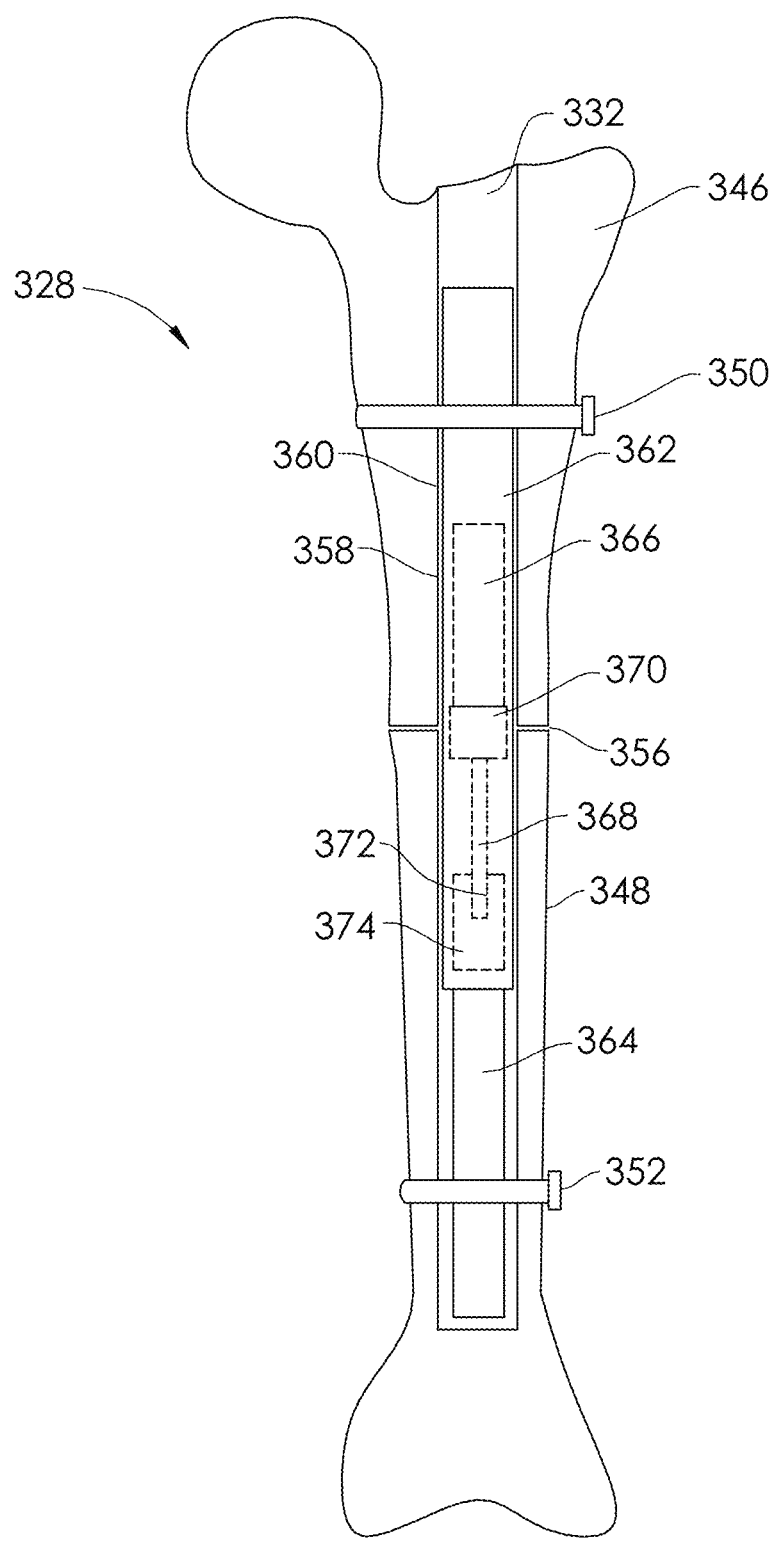
FIG. 28 is an embodiment of an adjustable implant for adjusting a rotational angle or torque between sections of bone.

A bone 328 is illustrated in FIG. 28 with an adjustable intramedullary implant 358 placed within the medullary canal 332. In this particular case, the bone 328 is a femur, though a variety of other bones are contemplated, including, but not limited to the tibia and humerus. The adjustable intramedullary implant 358 includes a first portion 360 having a cavity 362 and a second portion 364, rotationally disposed within the first portion 360. Within the cavity 362 of the first portion 360 is a rotatable permanent magnet 366, which is rotationally coupled to a lead screw 368, first example, via a gear module 370. The first portion 360 is secured to a first section 346 of the bone 328, for example, using a bone screw 350. The second portion 364 is secured to a second section 348 of the bone 328, for example, using a bone screw 352. Rotation of the permanent magnet 366 (for example, by application of an externally applied moving magnetic field of an external adjustment device 700, 502) causes rotation of the lead screw 368 within a female thread 372 that is disposed in a rotation module 374, and moves the first portion 360 and the second portion 364 rotationally with respect to each other. The rotation module 374 may make use of embodiments disclosed in U.S. Pat. No. 8,852,187. In bone rotational deformity applications, it may be desired to change the orientation between the first portion 346 and the second portion 348 of the bone 328, by creating an osteotomy 356, and then gradually rotating the bone sections 346, 348 with respect to each other. Stretching of the surrounding soft tissue may cause the patient significant pain. By use of the system 500, the patient or physician may determine a relationship between the patient's pain threshold and the force measured by the system 500. In future rotations, the force may be measured, and the pain threshold force avoided.

A knee joint 376 is illustrated in FIGS. 29 and 30, and comprises a femur 328, a tibia 394, and a fibula 384. Certain patients having osteoarthritis of the knee joint 376 may be eligible for implants configured to non-invasively adjust the angle of a wedge osteotomy 388 made in the tibia 394, which divides the tibia 394 into a first portion 390 and a second portion 392. Two such implants include an adjustable intramedullary implant 386 (FIG. 29) and an adjustable plate implant 420 (FIG. 30). The adjustable intramedullary implant 386 includes a first portion 396 which is secured to the first portion 390 of the tibia 394 using one or more bone screws 378, 380 and a second portion 398 which is secured to the second portion 392 of the tibia 394 using one or more bone screws 382. A permanent magnet 381 within the adjustable intramedullary implant 386 is rotationally coupled to a lead screw 383, which in turn engages female threads 385 of the second portion 398. In a particular embodiment, the bone screw 378 passes through the adjustable intramedullary implant 386 at a pivoting interface 387. As the angle of the osteotomy 388 is increased with one or more non-invasive adjustments, the bone screw 378 is able to pivot in relation to the adjustable intramedullary implant 386, while still holding the adjustable intramedullary implant 386 securely to the bone of the tibia 394. A rate of between about 0.5 mm and 2.5 mm per day may be effective in growing the angle of the bone, with minimal non-unions or early consolidation. Stretching of the surrounding soft tissue may cause the patient significant pain. By use of the system 500, the patient or physician may determine a relationship between the patient's pain threshold and the force measured by the system 500. In future lengthenings, the force may be measured, and the pain threshold force avoided.

The adjustable plate implant 420 (FIG. 30) includes a first portion 422 having a first plate 438, which is secured externally to the first portion 390 of the tibia 394 using one or more bone screws 426, 428 and a second portion 424 having a second plate 440, which is secured externally to the second portion 392 of the tibia 394 using one or more bone screws 430. A permanent magnet 432 within the adjustable plate implant 420 is rotationally coupled to a lead screw 434, which in turn engages female threads 436 of the second portion 424. Stretching of the surrounding soft tissue may cause the patient significant pain. By use of the system 500, the patient or physician determine a relationship between the patient's pain threshold and the force measured by the system 500. In future lengthenings, the force may be measured, and the pain threshold force avoided.

Figure 31:
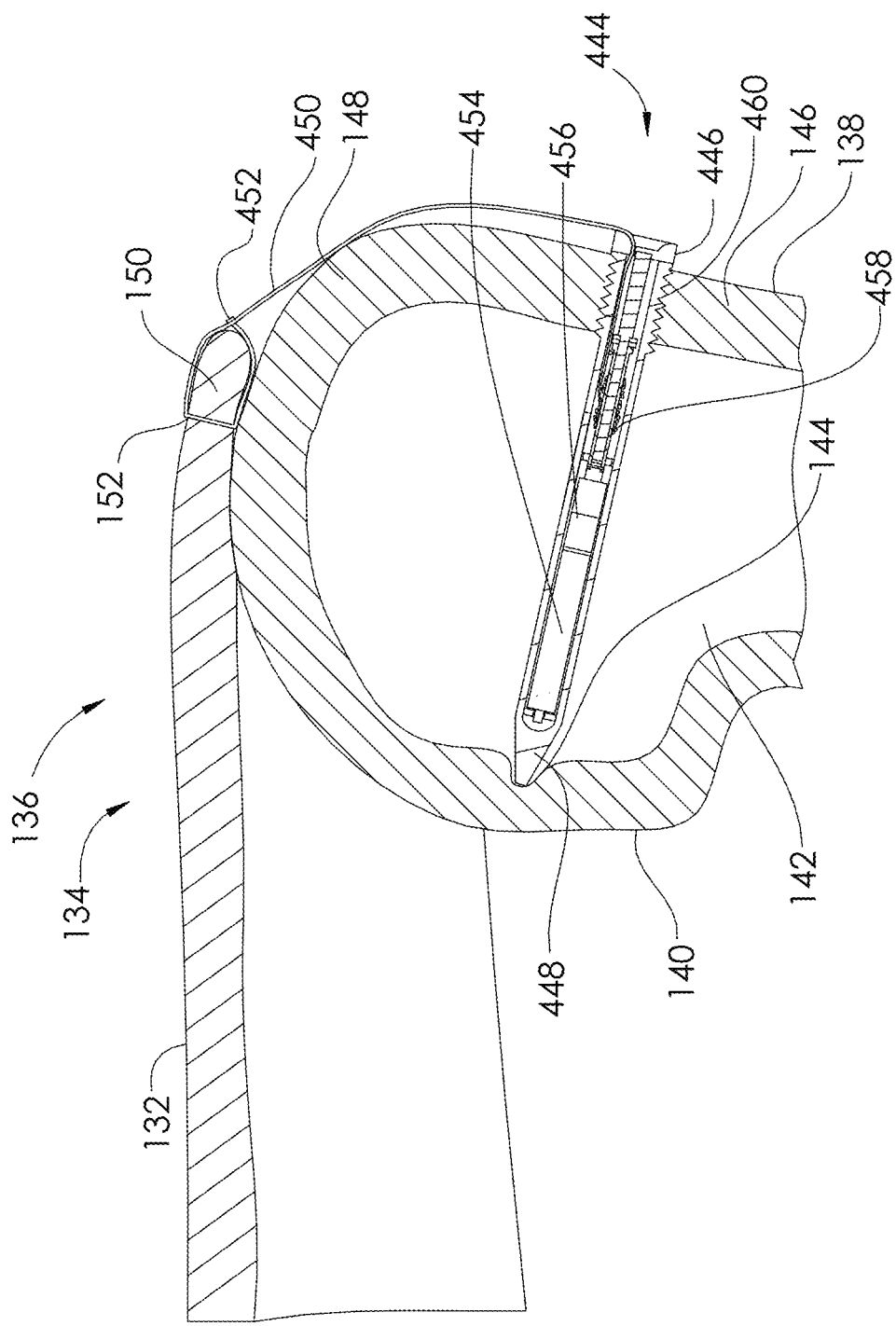
FIG. 31 is an embodiment of an adjustable implant for adjusting a location or force (tension) on body tissue.

An adjustable suture anchor 444 is illustrated in FIG. 31. Though the embodiment is shown in a rotator cuff 134 of a shoulder joint 136, the adjustable suture anchor 444 also has application in anterior cruciate ligament (ACL) repair, or any other soft tissue to bone attachment in which securement tension is an factor. The adjustable suture anchor 444 comprises a first end 446 and a second end 448 that is configured to insert into the head 140 of a humerus 138 through cortical bone 146 and cancellous bone 142. Threads 460 at the first end 446 are secured to the cortical bone 146 and the second end 448 may additionally be inserted into a pocket 144 for further stabilization. Suture 450 is wound around a spool 458 within the adjustable suture anchor 444, extends out of the adjustable suture anchor 444, and is attached to a tendon 150 of a muscle 132 through a puncture 152 by one or more knots 452, for example, at the greater tubercle 148 of the humerus 138. A permanent magnet 454 is rotatably held within the adjustable suture anchor 444 and is rotatably coupled to the spool 458, for example via a gear module 456. It may be desirable during and/or after surgery, to keep a muscle secured to a bone at a very specific range of tensions, so that healing is maximized and range of motion is optimized. Using the system 500, the force may be measured, adjusted accordingly, at surgery, immediately after surgery, and during the healing period in the weeks after surgery).

Figure 32:
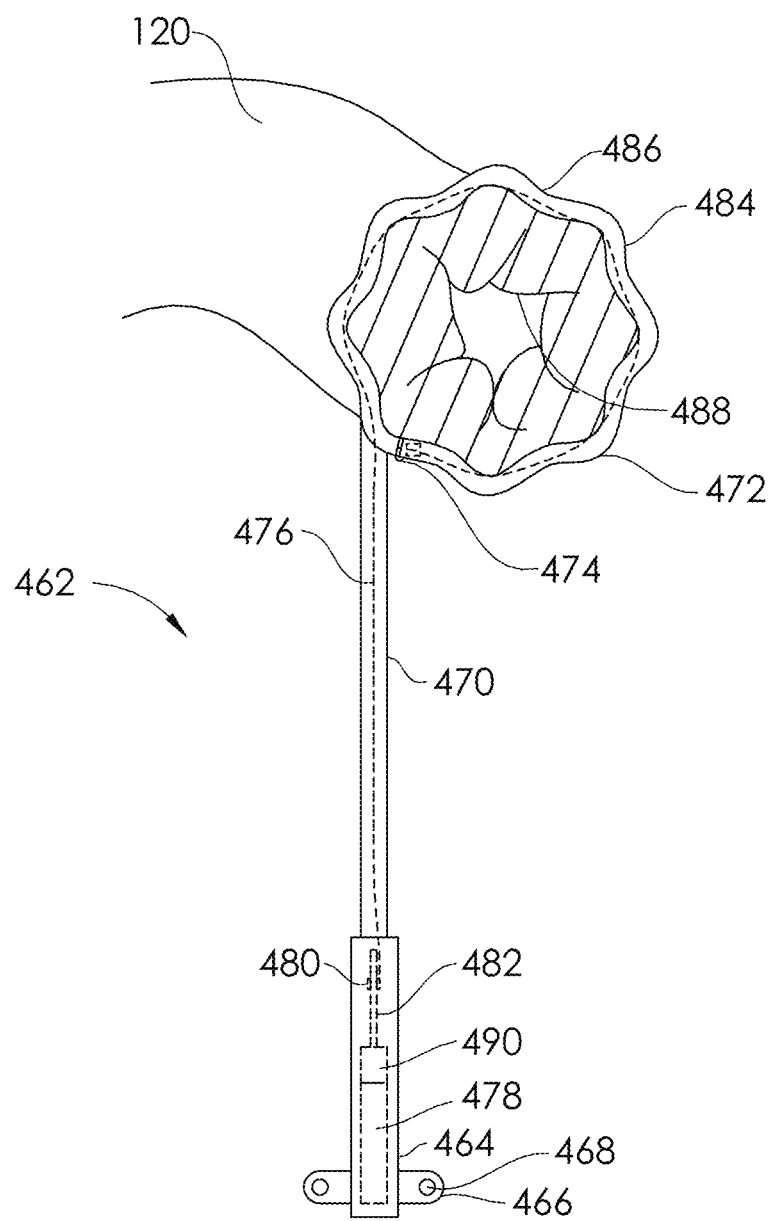
FIG. 32 is an embodiment of an adjustable implant for adjusting restriction on a duct of the body.

FIG. 32 illustrates an adjustable restriction device 462 having an adjustable ring 472 which is configured to be secured around a body duct 120 and closed with a closure or snap 474. The adjustable restriction device 462 may be implanted in a laparoscopic surgery. A housing 464 having suture tabs 466 is secured to the patient, for example, by suturing though holes 468 in the suture tabs 466 to the patient's tissue, such as fascia of abdominal muscle. Within the housing 464 is a magnet 478 which is rotationally coupled to a lead screw 482. A nut 480 threadingly engages with the lead screw 482 and is also engaged with a tensile line 476, which may comprise wire, for example Nitinol wire. The tensile line 476 passes through a protective sheath 470 and passes around the interior of a flexible jacket 484 that makes up the adjustable ring 472. The flexible jacket 484 may be constructed of silicone, and may have a wavy shape 486, that aids in its ability to constrict to a smaller diameter. The duct 120 is shown in cross-section at the edge of the adjustable ring 472, in order to show the restricted interior 488 of the duct 120. Certain gastrointestinal ducts including the stomach, esophagus, and small intestine may be adjustably restricted. Sphincters such as the anal and urethral sphincters may also be adjustably restricted. Blood vessels such as the pulmonary artery may also be adjustably restricted. During adjustment of the adjustable restriction device 462, an external adjustment device 700, 502 is placed in proximity to the patient and the magnet 478 is non-invasively rotated. The rotation of the magnet 478 rotates the lead screw 482, which, depending on the direction of rotation, either pulls the nut 480 toward the magnet 478 or pushes the nut away from the magnet 478, thereby either increasing restriction or releasing restriction, respectively. Because restricted ducts may have complex geometries, their effective size is hard to characterize, even using three-dimensional imaging modalities, such as CT or MRI. The force of constriction on the duct may be a more accurate way of estimating the effective restriction. For example, a stomach is restricted with a tangential force (akin to the tension on the tensile line 476) on the order of one pound. With a fine lead screw having about 80 threads per inch, a fine adjustment of the nut 480, and thus of the adjustable ring may be made. By including a gear module 490 between the magnet 478 and the lead screw 482, and even more precise adjustment may be made. By use of the system 500, the force may be measured, during adjustment, so that an "ideal restriction" may be returned to after changes occur in the patient (tissue growth, deformation, etc.).

Figure 34:
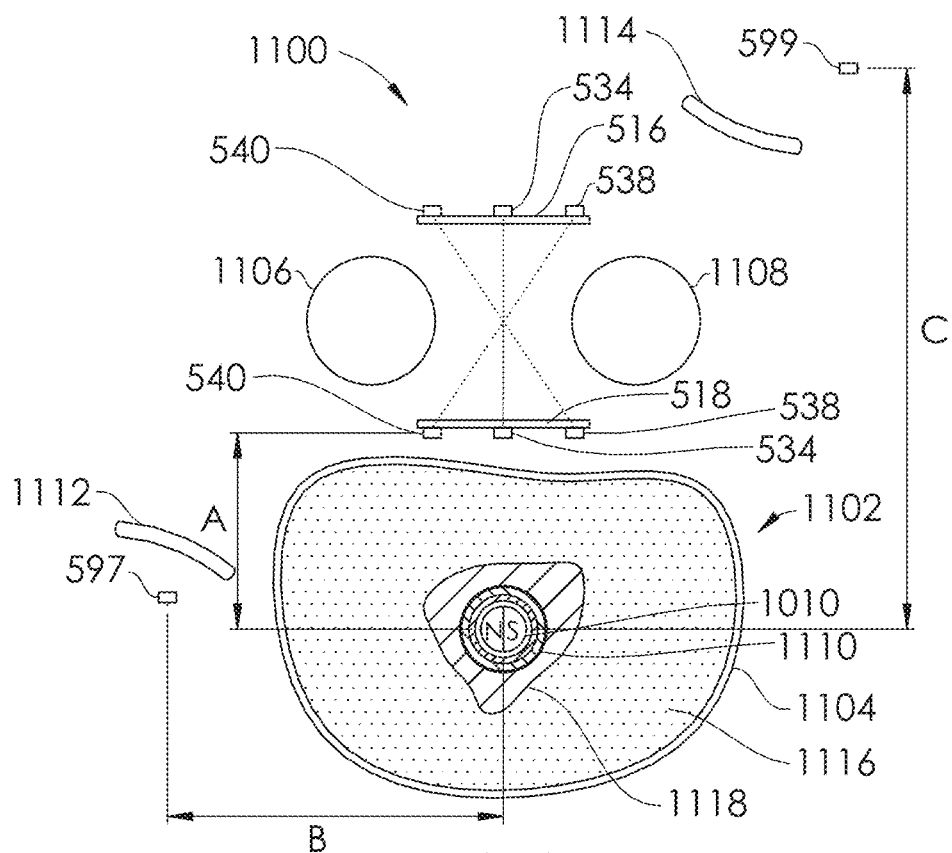
FIG. 34 is a partial sectional view of an array of magnetic sensors in relation to external magnets of one embodiment of an external adjustment device and an internal permanent magnet.

FIG. 34 illustrates an external adjustment device 1100 having one or more magnets 1106, 1108 which may comprise permanent magnets or electromagnets, as described in other embodiments herein. In some applications, one or more of the Hall effect sensors 534, 538, 540 may experience an undesired amount of saturation. An upper leg portion 1102 having a bone 1118 extending within muscle/fat 1116 and skin 1104 is shown in FIG. 34. An implant 1110, such as a limb lengthening implant, having a magnet 1010 is placed within the medullary canal of the bone 1118. In large upper leg portions 1102, for example in patients having a large amount of muscle or fat 1116, the distance "A" between the magnet 1010 and the Hall effect sensors 534, 538, 540 decreases the signal the magnet 1010 can impart on the Hall effect sensors 534, 538, 540 thus increasing the relative effect the one or more magnets 1106, 1108 have on the Hall effect sensors 534, 538, 540. The external adjustment device 1100 includes one or more Hall effect sensors 597, 599 spaced from the one or more magnets 1106, 1108. The one or more Hall effect sensors 597, 599 may be electrically coupled to the external adjustment device 1100 directly or remotely. In some embodiments, the one or more Hall effect sensors 597,599 may be mechanically attached to the external adjustment device 1100, or may be attachable to the body of the patient, for example to the upper leg portion 1102. Distances B and C may each range between about 5 cm and 15 cm, between about 7 cm and 11 cm, or between about 8 cm and 10 cm. In some embodiments, one or both of the Hall effect sensors 597, 599 may include a shield 1112, 1114 , such as a plate. The shield may comprise iron or MuMETAL®, (Magnetic Shield Corporation, Bensenville, Ill., USA). The shield may be shaped or oriented in a manner such that it is not between the particular Hall effect sensor 597, 599 and the magnet 1010, but is between the particular Hall effect sensor 597, 599 and the one or more magnets 1106, 1108. The Hall effect sensors 597, 599 may each be used to acquire a differential voltage, as described in relation to the other Hall effect sensors 534, 538, 540. Larger distances between that the Hall effect sensors 597, 599 and the one or more magnets 1106, 1108 can advantageously minimize the amount of saturation due to the magnets 1106, 1108. Additionally, the shield 1112, 1114 can significantly minimize the amount of saturation.

While embodiments have been shown and described, various modifications may be made without departing from the scope of the inventive concepts disclosed herein. The invention(s), therefore, should not be limited, except to the following claims, and their equivalents.

What is claimed is:

1. A remote control, comprising:
    one or more rotatable magnets coupled to a handle;
    a motor disposed in the handle, the motor operably coupled to the one or more rotatable magnets and configured to rotate the one or more rotatable magnets to transmit a rotating magnetic field to a medical implant having a rotatable permanent magnet wherein rotation of the permanent magnet changes a dimension of the medical implant;
    a first circuit board having an array of magnetic sensors and a second circuit board having an array of magnetic sensors, the first circuit board being disposed above the second circuit board, the second circuit board being located between the one or more rotatable magnets and the rotatable permanent magnet of the medical implant, with the first circuit board and second circuit board configured to receive information corresponding to changing magnetic field characteristics caused by the rotation of the rotatable permanent magnet of the medical implant, and configured to determine one or more of a force generated by the medical implant and a change in dimension of the medical implant; and
    a user interface configured to report to a user at least one of the force generated on the rotatable permanent magnet and an amount of change of the dimension of the medical implant,
    wherein at least two sensors of the array of magnetic sensors of the first circuit board have differing sensitivities relative to each other, and
    wherein at least two sensors of the array of magnetic sensors of the second circuit board have differing sensitivities relative to each other.

2. The remote control as in claim 1, wherein the user interface further comprises one or more displays configured to display an indicator of an amount of adjustment of the medical implant, in response to the rotating magnetic field.

3. The remote control as in claim 2, wherein the indicator of the amount of the adjustment comprises an indicator of a number of revolutions performed by the rotatable permanent magnet of the medical implant in response to the rotating magnetic field.

4. The remote control as in claim 2, wherein the one or more displays further comprise an indicator for indicating that the rotatable permanent magnet of the medical implant is not achieving a predetermined threshold of responsiveness to the rotating magnetic field.

5. The remote control as in claim 1, wherein when force is applied to the medical implant, the force is calculated by a processor based upon a measurement of the responsiveness of the medical implant to the rotating magnetic field.

6. The remote control as in claim 5, wherein the first circuit board comprising a Hall effect sensor array.

7. The remote control as in claim 6, wherein the first circuit board contains at least five Hall effect sensors, and wherein the second circuit board contains at least five Hall effect sensors.

8. The remote control as in claim 7, wherein an amount of force generated by the medical implant is determined at least in part from one or more voltage differentials between at least two of the five Hall effect sensors of the first circuit board and at least two of the five Hall effect sensors of the second circuit board.

9. The remote control as in claim 8, wherein when force is applied to the medical implant, the amount of force applied upon the medical implant is determined by the processor based at least in part on empirical data and curve fit data.

10. The remote control of claim 7, comprising at least one differential amplifier to acquire a differential voltage between at least two of the Hall effect sensors.

11. The remote control of claim 10, wherein the processor receives the input differential voltage data from the at least one differential amplifier and calculates one or more of: a binary proximity indication of the remote control relative to the medical implant; a distance between the remote control and the medical implant; a change in dimension of the medical implant in response to the magnetic field; and the maximum possible force applied upon the medical implant.

12. The remote control as in claim 1, wherein the amount of change of the dimension comprises a change in an axial dimension of at least a portion of the medical implant.

13. A remote control comprising:
    one or more rotatable magnets coupled to a handle;
    a motor disposed in the handle, the motor operably coupled to the one or more rotatable magnets and configured to rotate the one or more rotatable magnets to transmit a rotating magnetic field to a medical implant having a rotatable permanent magnet wherein rotation of the permanent magnet changes a dimension of the medical implant;
    a first circuit board having an array of magnetic sensors and a second circuit board having an array of Hall effect sensors, the first circuit board being disposed above the second circuit board, the second circuit board being located between the one or more rotatable magnets and the rotatable permanent magnet of the medical implant, with the first circuit board and second circuit board configured to receive information corresponding to changing magnetic field characteristics caused by the rotation of the rotatable permanent magnet of the medical implant, and configured to determine one or more of a force generated by the medical implant and a change in dimension of the medical implant; and a user interface configured to report to a user at least one of the force generated on the rotatable permanent magnet and an amount of change of the dimension of the medical implant, wherein at least two sensors of the array of Hall effect sensors of the first circuit board have differing sensitivities relative to each other, and wherein at least two sensors of the array of Hall effect sensors of the second circuit board have differing sensitivities relative to each other.

14. The remote control as in claim 13, wherein the amount of change in dimension comprises a change in an axial dimension of at least a portion of the medical implant.

15. The remote control as in claim 13, wherein the first circuit board contains at least five Hall effect sensors, and wherein the second circuit board contains at least five Hall effect sensors.

16. The remote control as in claim 15, wherein the amount of force generated by the medical implant is determined at least in part from one or more voltage differentials between at least two of the five Hall effect sensors of the first circuit board and at least two of the five Hall effect sensors of the second circuit board.

17. The remote control as in claim 16, wherein when force is applied to the medical implant, the amount of force applied upon the medical implant is determined by the processor based at least in part on empirical data and curve fit data.

18. A remote control comprising:

one or more rotatable magnets coupled to a handle;

a motor disposed in the handle, the motor operably coupled to the one or more rotatable magnets and configured to rotate the one or more rotatable magnets to transmit a rotating magnetic field to a medical implant having a rotatable permanent magnet wherein rotation of the rotatable permanent magnet changes a dimension of the medical implant;

a first circuit board having an array of magnetic sensors and a second circuit board having an array of magnetic sensors, the second circuit board being located between the one or more rotatable magnets and the rotatable permanent magnet of the medical implant, with the first circuit board and second circuit board configured to receive information corresponding to changing magnetic field characteristics caused by the rotation of the rotatable permanent magnet of the medical implant, and configured to determine one or more of a force generated by the medical implant and a change in dimension of the medical implant; and a user interface configured to report to a user at least one of the force generated on the rotatable permanent magnet and an amount of change of the dimension of the medical implant, wherein at least two sensors of the array of magnetic sensors of the first circuit board have differing sensitivities relative to each other, and wherein at least two sensors of the array of magnetic sensors of the second circuit board have differing sensitivities relative to each other.

* * * * *